United States Patent
Shachar et al.

(10) Patent No.: US 11,156,542 B2
(45) Date of Patent: Oct. 26, 2021

(54) SURFACE ACOUSTIC WAVE BIOSENSOR EMPLOYING AN ANALOG FRONT END AND DNA ENCODED LIBRARIES TO IMPROVED LIMIT OF DETECTION (LOD) WITH EXEMPLARY APPARATUS OF THE SAME

(71) Applicant: Sensor Kinesis Corporation, Los Angeles, CA (US)

(72) Inventors: Yehoshua Shachar, Santa Monica, CA (US); Roger Kornberg, Atherton, CA (US)

(73) Assignee: Autonomous Medical Devices Inc., Santa Monica, CA (US)

( * ) Notice: Subject to any disclaimer, the term of this patent is extended or adjusted under 35 U.S.C. 154(b) by 240 days.

(21) Appl. No.: 16/325,291

(22) PCT Filed: Aug. 22, 2017

(86) PCT No.: PCT/US2017/048055
§ 371 (c)(1),
(2) Date: Feb. 13, 2019

(87) PCT Pub. No.: WO2018/057201
PCT Pub. Date: Mar. 29, 2018

(65) Prior Publication Data
US 2019/0170631 A1 Jun. 6, 2019

Related U.S. Application Data

(60) Provisional application No. 62/397,233, filed on Sep. 20, 2016.

(51) Int. Cl.
| | | |
|---|---|---|
| *G01N 15/06* | (2006.01) | |
| *G01N 29/22* | (2006.01) | |
| *G01N 29/34* | (2006.01) | |
| *B81C 1/00* | (2006.01) | |
| *G01N 29/036* | (2006.01) | |
| *G01N 29/02* | (2006.01) | |
| *C12N 15/10* | (2006.01) | |
| *G01N 33/53* | (2006.01) | |
| *G01N 15/00* | (2006.01) | |

(52) U.S. Cl.
CPC ..... *G01N 15/0606* (2013.01); *B81C 1/00206* (2013.01); *C12N 15/1037* (2013.01); *G01N 29/022* (2013.01); *G01N 29/036* (2013.01); *G01N 29/222* (2013.01); *G01N 29/348* (2013.01); *G01N 33/5306* (2013.01); *B81B 2201/0214* (2013.01); *B81C 2201/0149* (2013.01); *G01N 2015/0065* (2013.01); *G01N 2291/0255* (2013.01); *G01N 2291/0256* (2013.01); *G01N 2291/0423* (2013.01)

(58) Field of Classification Search
None
See application file for complete search history.

(56) References Cited

U.S. PATENT DOCUMENTS

| | | | |
|---|---|---|---|
| 7,762,124 B2 * | 7/2010 | Okaguchi | G01N 29/022 73/61.49 |
| 8,156,814 B2 * | 4/2012 | Okaguchi | G01N 29/022 73/657 |
| 9,608,547 B2 * | 3/2017 | Ding | B07C 5/3427 |
| 9,821,310 B2 * | 11/2017 | Guldiken | B01L 3/502761 |
| 10,136,816 B2 * | 11/2018 | Bernstein | G16H 40/67 |
| 10,938,371 B2 * | 3/2021 | Nakamura | H03H 9/02834 |
| 2004/0078219 A1 | 4/2004 | Kaylor | |
| 2011/0213225 A1 * | 9/2011 | Bernstein | A61B 5/0017 600/309 |
| 2012/0282264 A1 | 11/2012 | Mascola | |
| 2016/0238553 A1 | 8/2016 | Shachar | |
| 2018/0334697 A1 * | 11/2018 | Shachar | A61L 29/16 |

FOREIGN PATENT DOCUMENTS

EP 2726873 1/2013

OTHER PUBLICATIONS

Puiu, Enhanced Sensitive Love Wave Surface Acoustic Wave Sensor Designed for Immunoassay Formats, Sensors 2015, 15, 10511-10225.
Gao, A Method for the Generation of Combinatorial Antibody Libraries using piX Phage Display, PNAS, Oct. 1, 2012, vol. 99, No. 20, 12612-12616.
Powell, Modelling of Layered Surface Acoustic Wave Resonators for Liquid Media Sensing Applications, School of Electric and Computer Engineering Science, Engineering and Technology Portfolio, RMIT University, May 2006, p. 74.

* cited by examiner

*Primary Examiner* — Ann Y Lam
(74) *Attorney, Agent, or Firm* — Marcus C. Dawes; Daniel L. Dawes

(57) ABSTRACT

A surface acoustic wave (SAW) performs a rapid, label-free detection of biological species. Biosensing and detection of multiple analytes multiplexed by an array of sensing lanes is configured to enable bio-amplification using engineered DNA encoded libraries as the probe through a phage display procedure to enhance specificity, capture statistics for the detection, screening and analyzing of the analyte in vitro. A biochemical formulation minimizes the limit of detection (LOD) at a threshold magnitude on the order of a femtomolar concentration. Additional enhancement of the apparatus is achieved by use of an analog front end to amplify biochemical events.

17 Claims, 42 Drawing Sheets

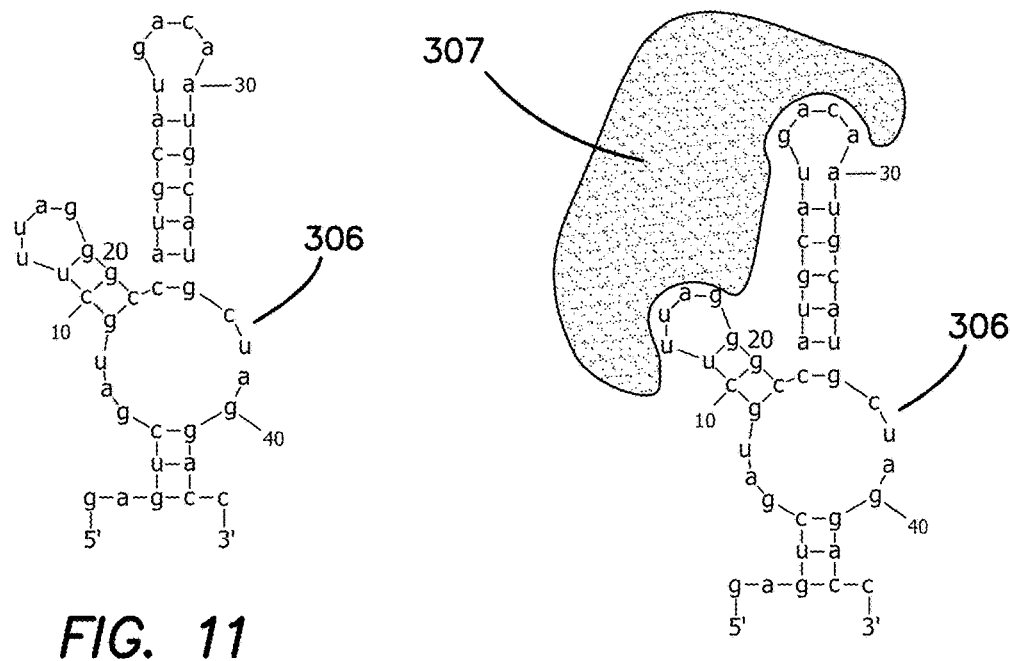
FIG. 11
FIG. 11A
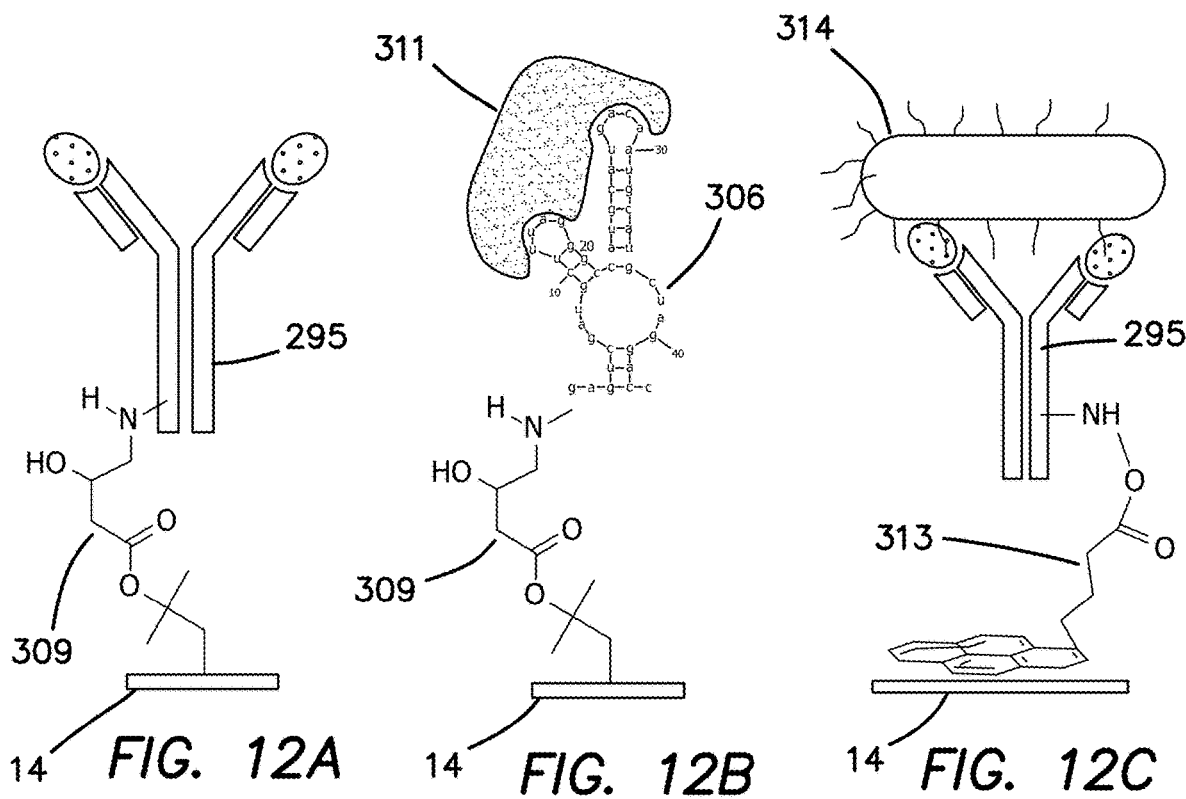
FIG. 12A
FIG. 12B
FIG. 12C

SURFACE ACOUSTIC WAVE BIOSENSOR EMPLOYING AN ANALOG FRONT END AND DNA ENCODED LIBRARIES TO IMPROVED LIMIT OF DETECTION (LOD) WITH EXEMPLARY APPARATUS OF THE SAME

BACKGROUND OF THE INVENTION

Field of the Invention

The invention relates to the field of biosensing employing a surface acoustic wave (SAW), where the principle of operation is based on rapid, label-free detection of biological species. More particularly, the invention is directed to biosensing and detection of multiple analytes multiplexed by an arrays of sensing lane(s) configured to enable bio-amplification using engineered DNA encoded libraries as a probe while employing a phage display procedure to enhance specificity, capture statistics for the detection, screening and analysis of the analyte in vitro. A biochemical enhancement minimizes the limit of detection (LOD) at a threshold magnitude at femtomolar concentrations. Additional enhancement of the apparatus is realized using an analog front end (AFE) to amplify the biochemical events.

Prior Art

"High-Frequency Shear-Horizontal Surface Acoustic Wave Sensor" U.S. Pat. No. 8,436,509 May 7, 2013, and "Carbon Nanotube BioFET with a Local Amplifier in a System Array for Analysis of Biomarkers and Method of Analysis of Same", U.S. patent application Ser. No. 12/581,758 filed Oct. 19, 2009, are hereby incorporated by reference in their entirety.

Brenner S, Lerner R A (June 1992). "Encoded combinatorial chemistry". Proc. Natl. Acad. Sci. U.S.A. 89 (12): 5381-3 is a foundational disclosure relevant to the biochemical enhancement utilized in the illustrated embodiments.

BACKGROUND TO THE INVENTION

In the fields of analytical and physical chemistry, medical diagnostics and biotechnology there is an increasing demand of highly selective and sensitive analytical techniques which optimally allow a real-time label-free monitoring with easy to use, reliable, miniaturized and low cost devices. Biosensors meet many of the above features, which have led them to gain a place in the analytical bench top as alternative or complementary methods for routine classical analysis. Different sensing technologies are being used for biosensors. Categorized by the transducer mechanism, optical and acoustic wave sensing technologies have emerged as very promising biosensors technologies. Optical sensing represents the most of the technology currently used in biosensors applications. Among others, surface plasmon resonance (SPR) is probably one of the better-known label-free optical techniques, but its high cost is the main shortcoming of this method.

Acoustic wave devices represent a cost-effective alternative to these advanced optical approaches, since they combine their direct detection (label-free), simplicity in handling, real-time monitoring, and good sensitivity and selectivity. Such capabilities are achieved with a reduced cost and above all considerations, is the ability of such apparatus to be used in the field without the necessary technical know-how.

The principle challenge of the use of acoustic techniques, which remain to be resolved, is: Improvement of sensitivity with the objective of reducing the limit of detection (LOD), Synchronous detection of multi-analyte present in a complex assay, (high-throughput screening systems), and integration of such capabilities in a portable, lower cost and field deployable biosensor.

The most obvious parameter defining the resolution and accuracy of the proposed sensor is its inherent limit of detection (LOD), which can be measured and defined as; the smallest detectable concentration of a certain substance or the lowest detectable molecular mass of a certain concentration of molecules, or the lowest detectable affinity of a chemical reaction or for surface-based sensors, or the lowest detectable surface mass density. We therefore employ the definition of the smallest detectable surface mass as the focus. This definition is set, due to the physical nature of employing a surface acoustic wave platform to measure mass accumulation over the sensing lane due to conjugation-dependence on a specific biological probe, this physical attribute entails that mass and only mass addition is the measured (independent) variable in a complex acousto-mechanical set of parameters.

The dependency on the transducer design with the aim of improving the LOD is the central chemical/engineering task. Other parameters like the smallest detectable concentration, is highly depended on factors which are independent from the transducer design, including the functionalization of surface chemistry, linker affinity, type of antibody specificity, use of fragmented antibody, spacer molecule and antibody orientation, measures such as spacer-molecules density and compaction geometry of probes or the microfluidic chamber hydrostatic flow, are some of the primary ingredients which contribute to the LOD resolution. However, other parameters besides the sensitivity measure, are also equally important: The required sample volume is crucial if many substances or many different concentrations are measured like in high-throughput screening or, where sample volume is available in very limited amounts or the transducer ability to resolve cases, where the analyte concentration is so high relative to the sensing lane capacity, resulting in early saturation and therefore the apparatus reports an unrepresentative value relative to the analyte's true concentration in the assay.

Therefore, there is a need for an apparatus that can optimize the complex parametric exchange noted above and provide a multiplexing with multi-variable analytes, where parallel measurements are performed without significantly increasing the equipment size and its cost of fabrication. It needs to be a portable device and its analytical data is comparable to clinical standards such as PCR.

The so-called gravimetric technique, based on the change in the resonance frequency experimented by the resonator due to a mass attached on the sensor surface, has opened a great deal of applications in bio-chemical sensing in both gas and liquid media.

Traditionally, the most commonly used acoustic wave biosensor is based on quartz crystal microbalance (QCM) devices. Love Wave (LW) acoustic sensors have attracted a great deal of attention in the scientific community during the last two decades, due to its reported high sensitivity in liquid media compared to traditional QCM-based sensors. In electrodynamics, Love waves are horizontally-polarized surface waves. The Love wave is a result of the interference of many shear waves (S-waves) guided by an elastic layer, the piezoelectric layer governed by Helmholtz equation $\nabla^2 A + k^2 A = 0$, where $\nabla^2$ is the Laplacian, k is the wave number, and A is the amplitude. The S waves are the result of the electrical impulse due to polarization of the piezoelectric substrate resulting in stress-strain relationship in an isotropic solid, thereby reducing the measured variable to mass change due to hybridization between the analyte and its specific probe.

Nevertheless, there are still some issues to be refined, clarified and/or improved about this assumption, as the accuracy of the sensor as a sensitive mass balance apparatus, is directly related to the apparatus ability to resolve a molecular mass in the order of $10^{-15}$ moles per volume of analyte within the microfluidic chamber, typically in the order of 0.15-1.5 ml of a samples size.

This challenge of confining the sheer horizontal waves (SH) generated by the surface acoustic wave (SAW), enables a resolution for detecting analyte with minimal LOD (femtomolar concentration. This effort of optimization is set along the sensor design of the crystal resonator formed out of $LiTaO_3$, where the characteristic S-waves are isotropic within the liquid medium and the frequency domain is set within the band of 300 MHz-400 MHz and that selection of the frequency-generator is suited to achieve the desired resolution.

SH SAW devices are able to operate at higher frequencies than traditional QCMs; typical operation frequencies are between 80-400 MHz; higher frequencies lead in principle to higher sensitivity because the acoustic wave penetration depth into the adjacent media is reduced. However, the increase in the operation frequency also results in an increased noise level, thus restricting the LOD. The LOD determines the minimum surface mass that can be detected. In this sense, the optimization of the read out and characterization system for these high frequency devices is one of the key aspect for improving the LOD. The carful design of the analog front end of the proposed biosensor, addresses the inherent conflict of higher frequency-higher resolution with the relative SNR increase of the read-out, by gating the gain and suppressing the parasitic noise.

Another aspect of SAW technology is the optimization of the fluidics chamber to meet the LOD's threshold, especially the cell hydrodynamic flow characteristics. This element of the system level design impact on reduction of noise, due to flow disturbance such as fluid rotation about the chamber axis and, vortices ("secondary flows"), due to swirling-motion with high local velocity often caused by separation, or sudden enlargement in surface area in which the analyte is entered to the microfluidic chamber. The above hydrostatic considerations contributes to the ability of the apparatus in resolving LOD of the order necessary in meeting the objective of femtomolar concentration limits.

The analysis and interpretation of the results obtained with surface acoustic wave biosensor must resolve and detect the analyte in question at a concentration of $10^{-15}$ moles per liter. Since the acoustic signal presents a mixed contribution of changes in the mass and the viscoelasticity of the adsorbed layers (due to interactions of the biomolecules), a deliberate effort is to set and identify the conditions of which the transduction mechanism in SH SAW sensors must be identified, where the aim is a femtomolar limit of detection. However, the inherent complexity of the sensor fabrication and trade-off between resolution and sensitivity leads to a design of suboptimal performance of the device, unless the variables comprising such complexity and its exchanged parameters, are defined with a careful trade off studies assessed relative to reduction of LOD concentration per volume.

Prior Art Review

U.S. Pat. No. 8,436,509 titled "High-Frequency Shear-Horizontal Surface Acoustic Wave Sensor" describes a Love Wave sensor, which uses a single-phase unidirectional interdigital transducer (IDT) on a piezoelectric substrate for leaky surface acoustic wave generation. The IDT design minimizes propagation losses, bulk wave interferences, provides a linear phase response, and eliminates the need for impedance matching. As an example, a high frequency (~300-400 MHz) surface acoustic wave (SAW) transducer enables efficient excitation of shear-horizontal Waves on 36° Y-cut lithium tantalate (LTO) giving a highly linear phase response (2.8° P-P). The sensor has the ability to detect at the $pg/mm^2$ level and can perform multi-analyte detection in real time. The sensor used, for rapid autonomous detection of pathogenic microorganisms and bioagents as field deployable platforms.

Surface Acoustic Wave Biosensing method where measured output of biological species with high mass and viscous sensitivity and with a minimal need for additional reagents, label free is presented. Minimizing the use of reagents is desirable for field deployable chemical and biodetection systems. The transduction mechanism for SH SAW sensors is based on propagating waves with a shear horizontal (SH) polarization along the propagation direction.

As shown by the above description and its implementation, there are still limitations, which need to be solved in the case of a sheer horizontal surface acoustic wave biosensor with respect to the problem of optimizing the chemical-scaffolding of the biological probe, while combining such advances with novel use of a $LiTaO_3$ crystal with its 36° Y-cut X-propagation wave.

The bioagents acting as a probe (for the conjugating antibody/analyte) are configured to improve capture rate statistics, increase specificity, and reduce signal-to-noise ratios (SNR) by the careful tailoring of the chemical recipe, surface functionalization, as well as the electronics in which a small biological signal is to be separated from its noisy environment, this is the task where the use of an analog front end (AFE) is intended to solve and it is described below. An improved signal is obtained with a chemical recipe of fragmented antibody and spacer molecules, which amplify and preserve the native signal without distortion. Signal fidelity, improved specificity and statistical capture-rate above that achieved in the prior art is presented.

The prior art as illustrated by the '509 patent above describes a microfabricated biological sensor based on an acoustic device that combines a biologically active interface, which binds biological species (i.e., analytes) from an environment with a physical transducer that generates an electrical output proportional to the amount of bound analyte. A commonly used acoustic device for biological sensing includes leaky surface acoustic wave (LSAW) sensors that rely on the electrical excitation of a shear-horizontal surface acoustic wave on a piezoelectric substrate. Typically, a wave is established on a surface and the collection of analyte mass on the surface influences the propagation of the surface wave. In particular, these analyte-induced changes which in turn are sensed as variations in the velocity-time constant ($\tau$) and amplitude ($\lambda$) of the surface wave.

The use of shear horizontal (SH) polarization minimizes attenuation of the surface acoustic wave into viscous media permitting detection in liquids, and an integrated microfluidic and its SAW interdigitated electrodes which are optimized to the sensing range are aspects of focus below.

Love Wave sensors comprise a piezoelectric substrate that primarily excites SH waves, which are subsequently confined by a thin guiding layer. In general, if the layer material loads the substrate (i.e., the shear velocity in the layer is smaller than in the substrate), the SH bulk mode will become a surface mode having a single, transverse component of displacement confined within a few wavelengths of the surface. In particular, at high frequencies, such that the wavelength is less than the layer thickness, a surface Love Wave can be concentrated in the thin waveguide layer. Therefore, the waveguide layer is crucial to achieve high sensitivity by having a low shear velocity compared to the substrate.

For biodetection, the waveguide layer can also provide a mechanism for stable chemical attachment through covalent linkage of antibodies, DNA, or other biomolecules to achieve the required selectivity. Waveguide materials such as polymers, silicon dioxide ($SiO_2$), are used in the illustrated embodiments below.

However, piezoelectric substrates that support such leaky surface acoustic Waves, such as Love Waves, require advanced transducer designs to avoid excitation of undesired modes. Unlike Rayleigh Wave devices, where a true surface wave exists in the absence of dispersion, LSAW transducers require that bulk waves are suppressed and that intra-device acoustic reflections are minimized. Existing bidirectional transducers have major drawbacks in this regard, since waves are launched in both the forward and backward directions and are complicated by bulk wave generation. Above about 100 MHz, the phase is highly non-linear and other modes interfere with the main SH sensing mode. Although edge reflections from backward traveling waves can be easily suppressed on substrates that support Rayleigh Waves, by use of absorbers, this is not possible on substrates that support leaky waves. Moreover, since surface-skimming bulk waves (SSBW) propagate with a velocity very close to the leaky or shear horizontal mode on piezoelectric substrates, such as 36° YX lithium tantalate, the design of the transducer is highly critical to the excitation of the proper mode, especially at high frequencies. The design is further complicated by the fact that the electrode metal thickness determines the degree of propagation loss for leaky waves on lithium tantalate crystal.

Therefore, a need exists for a SH surface acoustic wave (Love Wave) sensor having a high-frequency interdigital transducer that provides low insertion loss and high out of band rejection, while suppressing bulk wave excitation at the stop band to enable high sensitivity detection of biological and chemical analytes in a fluid.

SUMMARY OF THE INVENTION

The illustrated embodiments are based on the view that in structural biology understanding of a biological process is primordially a study of the mechanism and function of chemical attributes in which the components of molecules must on the one hand be perfectly rigid in order to have a defined shape, much like the parts of a machine, to execute their function, while at the same time and at appropriate times they are capable of bending, so that they can adopt multiple states of organization as appropriate for their function. But the underlying principle is one of rigidity and a precise definition in much the same manner as one would envisage a piece of combustion engine.

The amplification of small biological signals are represented by an electrical equivalent creates a class of analytical machines for the study of biochemical processes.

Two areas of such approach to bio-amplification are presented, an improved capture statistics of conjugation between the target analye and its specific probe while employing a DNA encoded libraries, to engineer a an improved antibody with molecular affinity, multi-epitopes and optimized directionality. A phage display in combinatorial libraries is employed as a method to achieve improved specificity and reduction of the limit of detection (LOD). The signal fidelity obtained by the use of high-density compaction and directional orientation of the biochemical sensing probe undergoes a conformational transaction where the biochemical events are electrically represented. A careful implementation of an electronic scheme uses an analog front end (AFE) to achieve the electrical representation. Both techniques of bioamplification and electronic transduction of the small biological events achieve a low level of detection with limits set at femtomolar concentration of $10^{-15}$ (LOD) molecules per volume.

One feature of the illustrated embodiments is the ability to amplify the native biological signal of detection between the functionalized surface of the sensing lane and its target analyte without the customary technique of polymerase chain reaction (PCR), and to further provide means for electronic amplification as well as biological amplification of a label-free analyte/antibody conjugation by means, such as described by the use of encoded DNA libraries, to form an effective probe as well as an equivalent signal with electronic amplifier, defined by use of an analog front end (AFE).

To answer the challenges posed above, this application is centered on the ability of the biosensing apparatus to enable two distinct complementary methods by which a reduction of LOD is possible: 1) bio-amplification by the use of encoded DNA libraries to generate a potent probe with high specificity and improved statistical capture rate, achieved by the use of phage display in combinatorial libraries and 2) electronic amplification of small biological signals with the use of a analog front end (AFE) where electronic means is used to amplify the biological signal with an improved signal to noise ratio (SNR), spurious-free dynamic range (SFDR), which is the strength ratio of the fundamental signal to the strongest spurious signal in the output and dynamic range (DR) which enable the sensing platform to resolve linearly few orders of magnitudes of measured variables.

Both techniques; bioamplification and electronic amplification, used in improving the minimal LOD's parameter on the sensor platform, are detailed by the application and noted by its figures and accompanying descriptions.

The fabrication process of the transducer, such as self assembled monolayer (SAM) "head groups" such as: thiol, silanes or phosphonates on gold and assembled together on the substrate, while the tail groups assemble far from the substrate with a directionality suitable for increase statistical capture and where areas of close-packed molecules nucleate and grow until the surface of the substrate in a single monolayer. We employ a mix of the functionalized group (—OH, —NH2, —COO), with spacer molecules (a ternary surface monolayer, comprised of co-assembled thiolated capture probes), to eliminate the phenomenon of monatomic vacancy islands. We discuss features of the apparatus such as substrate materials, sizes of interdigitated sensing electrodes, structured packaging of antibodies, compaction of probe ratio to surface area and consistent functionalization of the sensing lanes, which contribute to LOD and ways to optimized such effects.

The illustrated embodiments include hand-held, portable, guided lithium tantalate ($LiTaO_3$) surface acoustic wave biosensors to be used as antibody-based biosensors for pathogens and protein biomarkers. In one embodiment, a derivative of the SAW biosensor is used for rapid nucleic acids analysis by combining a SAW biosensor with electrochemical detection strategy for nucleic acid analysis. This biosensor technology provides a versatile medical tool capable of rapidly screening samples of biological fluid for biomarkers associated with many forms of pathogenic infection, cancer, and genetic disorders. Since many life-threatening forms of infectious diseases, cancers and genetic disorders require long term management of therapy, this system can play a vital role in optimizing treatment regimens at minimal time and cost.

Biosensors are analytical devices that combine biological recognition with a physical or chemical transduction event. The recorded bimolecular interactions are transformed by the use of a novel analog front end (AFE) into digital signals, which are interpreted by a computing device or a smart device such as smart phone. This embodiment allows real-time or near real-time analysis. Reduced time of analysis is critical when it could lead to reduced times for the administration of treatments.

Biosensors can be separated into two groups, direct and indirect. If a label must be used in order to make a measurement, the technique is considered an indirect method. In contrast, if no labels were required, the sensor would be considered a direct sensor. As an example, the biosensor directly measures the change in mass loading on piezoelectric material. Therefore, this method is considered a direct (label-free) measurement. Surface acoustic wave (SAW) biosensors are among a limited number of direct biosensing techniques that are currently available. The sensitivity measure of these assays is dependent on the substrate used, the temperature, and the quality of the targeting molecules used. The biosensor includes a functionalized sensor surface where the analyte is recognized and bound. A transducer converts the binding event into an electrical signal, which is processed or analyzed and then communicated to the biosensor output. The biosensor uses either a covalently immobilized protein or single-stranded nucleic acid sequence immobilized on a gold surface employing alkyl thiol linkers.

A monolithic SAW biosensor system fabricated on a lithium tantalite substrate ($LiTaO_3$) typically utilizes the strategies based on binding of the pathogen to an antibody, nucleic acid, bacteriophage or protein agglutinant for conducting real-time or near real-time detection of pathogen, disease biomarkers and coupled with a electrochemical system for rapid nucleic acid analysis. The SAW biosensors are specifically configured for the detection of completely microbial pathogens, protein biomarkers and nucleic acid in a biological matrix. The SAW biosensors provide relevant information for example to patients who are likely to respond to a given therapy, as well as biomarkers that have the ability to measure a patient's response to therapy. In one embodiment, the use of such measures is necessary for personalizing the drug treatment for each patient. The SAW devices provide preventative information with respect to rapid, point-of-care detection of biological contaminations or infection.

One example of the use of this invention is in the field of food safety or monitoring food quality before food items are consumed.

Interdigitated gold acoustic wave biosensors on lithium tantalite substrates are platforms ideally suited as label-free biosensors for aqueous-based samples. This technology is a portable, rapid and sensitive detection system, primarily in the telecommunications industry. Recent advancements in the technology, has allowed for the creation guided shear surface acoustic wave (SAW) devices that can operate in liquid environments. These devices can be functionalized through immobilization of antibodies or antibody fragments to target biomarkers, which will dramatically enhance the use of such systems over previous generation of SAW devices. Enhanced surface chemistry techniques along with methods of attaching antibody fragments that bind specifically to biomarkers for various diseases are disclosed in this application.

When performing studies with SAW biosensing in liquid environments for the detection of microbes, eukaryotic cells, protein biomarkers or nucleic acid sequences, there is a strong loss of longitudinal bulk modes such as Raleigh surface waves and most Lamb-wave modes. Surface waves with displacements normal to the surface generate compressional waves, which dissipate wave energy in the liquid. For this reason, acoustic waves that have the particle displacement parallel to the device surface, normal to the wave propagation direction is employed by this application. These waves, which are referred to as shear-horizontal (SH) waves, propagate without coupling acoustic energy into the liquid. In particular, Love-Waves are SH waves that propagate in a thin guiding layer on SH-SAW devices. If a no-slip boundary condition is assumed at the sensing surface, a thin layer of liquid becomes entrained with a shear movement at the surface for viscous liquids. This viscous loading affects the Love-Wave in two ways. First, the entrainment results in mass loading of the wave-guiding layer, resulting in changes to the wave number. Second, the wave is damped due to viscous losses in the liquid. To reduce aqueous effects, the guiding layer is shielded in gold to prevent electrical loading of the IDTs. Love-Waves are SH and are confined to the thin layer between the wave-guides with the requirement that the shear velocity in this guiding layer (the velocity in the material forming the wave-guides) is less than the shear velocity in the piezoelectric substrate. For this reason, the waveguide is a significant structure for proper Love mode operation as mass-sensitive biosensors.

SAW sensors are well known to offer high surface-mass detection sensitivity for chemical sensing. It is possible to measure mass sensitivities from surface loading in the 1-100 $ng/cm^2$ range. The traditional configuration of SAW devices involves a chemically functionalized area that immobilizes a targeted species with a selective surface coating. The attachment of the targeted species perturbs a propagating surface acoustic wave that is generated by the interdigitated (IDT) e.g. gold (Au) electrode or aluminum (Al). The system also uses a reference lane, which uses an antibody that is not specific to the target. This reference lane is used to account for non-specific binding on the sensing area. The acoustic wave is detected by a second set of IDT located downstream from the first set of IDT. If the targeted species is present, then the propagating wave will be perturbed in such a way to cause a shift in the phase, frequency or amplitude, relative to wave that propagated across the reference electrode. These miniature biosensors are configured in an array format where multiple delay lines are scanned in parallel for a single target, but the device could also be operated in series to scan for multiple biomarkers for different diseases. Operating a SAW array allows rapid, point-of-care diagnostic using small portable devices. The use of miniature monolithic SAW sensor arrays allows on-chip signal processing, and allows the chips to be fully integrated into a larger system and easily packaged.

Temperature compensation is inherent to this system since the SAW's reference and the sensing channels are on the same substrate and therefore experience the same temperature fluctuations. Therefore, the controller automatically sets any adjustment to the phase due to temperature fluctuations. The determination of the phase shift is detected by using a circuitry, which identifies phase shift proportional to the mass loading due to hybridization of the analyte to its specific antibody, (a mass loading change, alter the frequency and amplitude in the isotropic liquid media). The phase detector extracts the difference in phase between the resonance frequency from the reference and the resonance frequency of the delay line being probed. The resulting phase shift is then calibrated for changes in the mass loading of the surface. This process cancels out any temperature dependence. Measurements in all channels are differential measurements relative to the reference lane. Both the reference and the delay lanes experience the same changes since the reference and sensing lanes are both subjected simultaneously to the buffer as well as the analyte in question. Hence, the reference lanes act as a built-in control and the output is the result of a differential signal between the sensing lane and the reference lane throughout the measurement. This feature of the preferred embodiment provides the system with a built-in standard as the relative frequency shift depends only on the hybridization, or mass loading, on the sensing lane relative to the reference lane (which is functionalized with a non-specific antibody). Hence, relative frequency or amplitude shift is the only measure for defining the performance of the sensor, as the major advantage of the novel SAW biosensor is in its invariance to an absolute calibration standard.

Antibody-based coated SAW biosensors permit the rapid and sensitive analysis of a range of pathogens and their associated toxins. The presence of bacterial pathogens, fungus and viral particles, which are ubiquitous in our environment, Therefore, monitoring for the presence of microorganisms is essential in maintaining proper health. This is especially true for short shelf-life foods, where mass-based piezoelectric biosensors operating on the principle that a change in the mass, resulting from the molecular interactions between a targeting molecule and the target can be determined. For example, mass changes result in alterations in the resonance frequency of a Lithium tantalite crystal. These piezoelectric immune-sensors are affordable and disposable options for pathogen detection of biohazard.

Outbreaks of food-borne and water-borne pathogens remain a major cause of disease and mortality throughout the world. The rapid detection of these pathogenic microorganisms is necessary for the prevention of public health epidemics. The quantitative identification of microorganisms has become one of the key points in areas of biodefense and food safety. To date, the detection and identification of pathogens rely primarily on classic microbiology methods of culturing. In such cases, the technician is required to go through a series of handling steps. There are several rapid methods that are now also used in microbiology that utilize enzyme-linked immunosorbent assays (ELISA) or polymerase chain reaction (PCR) assays. These methods are laborious and time consuming. These methods are also not able to deliver real-time analysis or point-of-care analysis. The use of portable biosensors to rapidly identify pathogens in food and water offers several advantages over the other rapid methods.

The prior art as noted by Branch el at demonstrated the detection of the endospores from the gram negative bacterial specie Bacillus thuringiensis, (Biosensors and Bioelectronics 19 (2004) 849-859) a simulant of Bacillus anthracis. Bacillus anthracis is the causative agent for anthrax, a potentially fatal bacterial infection that has been used as a bioterrorist agent. A LiTaO$_3$ Love-wave biosensor was used to demonstrate a detection level of 1 ng/cm$^2$ when using a polyimide guided layer and bovine serum albumin (BSA) as the blocking agent. The detection of such low levels of anthrax simulants revealed the ability to detect clinically relevant doses of Bacillus antracis endospores. Larson et al (Journal of Clinical Microbiology p. 1685-1691 June 2013 Volume 51 Number 6) used a similar device to detect both HIV and Ebola viruses at clinically relevant doses. All three devices used antibodies conjugated to a SiO$_2$ layer on a LiTaO$_3$ substrate. In preliminary experiments, the SAW proved capable of detecting concentrations spanning three orders of magnitude, with an estimated limit of detection (LOD) of 74 cells. While the cell mass is not a true concentration, the use of an accurate standard curve will allow the rapid correlation to a potential threat concentration. In other studies, SAW biosensors have been used to detect Ebola virus as a potential point-of-care diagnostic tool.

Polyclonal, monoclonal and recombinant antibodies have frequently been selected for a wide variety of applications including biomarker detection. Their production involves the exploitation of the immune system of a host organism to produce antibody against the targeted specie. Typically, a host organism is immunized with cells or inactivated microorganisms. Polyclonal antibodies are typically raised in larger mammals. The antibodies are widely used in immunosensor assays for pathogens. However, the inherent nature of polyclonal antibody is to bind different epitopes on a single target. In cases where this is undesirable, monoclonal or recombinant antibodies are used. Monoclonal antibodies are often generated through the use of hybridomas technology and murine hosts. The bone marrow, primary lymph nodes and spleen are selected as a source of antibody-producing B cells, which are harvested and fused to immortal myeloma cells. The resulting hybrid cells (hybridomas) secrete full-length antibodies that are directed towards a single epitope. Recombinant antibodies are generated with a phage display technology and the biopanning of antibody reporters against a target of interest. Three types of libraries may be used as sources of antibody pools: synthetic, naïve and immune.

The attachment of active recognition molecules, such as antibodies, at high-density to the transducer surface is one of the most critical steps in biosensor development to achieve an LOD at a concentration $10^{15}$ level. The proper strategies for attachment of an antibody fragment, such as Fab or single domain region, depend on the substrate. The SiO$_2$ coated LiTaO$_3$ SAW devices employ APTES for a covalent immobilization of antibody fragments. Often, biosensors employ protein immobilization strategies are randomly adsorbed on the surface (SAM). In the illustrated embodiments, either APTES for antibody attachments or gold-thiol chemistry for nucleic acid immobilization is used.

Love-wave sensors have been used where the antigens were known to have low molecular weights so that their diffusion times to the surface are estimated to be a few seconds. In whole microbial cell detection, the cell sizes can be up to a few microns in diameter (assuming a sphere or cylindrical cell). In the regime where large cells in the range from 0.5-5 µm are captured, the diffusion time may require capture times up to tens of minutes. Moreover, larger particles can settle due to gravimetric settling. Despite these difficulties, whole cell detection has several distinct advantages including: minimal sample preparation and the antigen site do not need to be known as long as antibodies are available.

The formation of organosilane-based thin films provides a simple means to incorporate chemically well-defined functional groups on glass-type surfaces. Variations in either the terminal groups or structure of organosilanes have greatly extended the utility of SAW devices by presenting specific chemical groups and altering the physical properties of SAW devices and extending these devices to many new applications. The sensing area is incorporated into the waveguides by the construction of the integrated microfluidic chamber. For example, the amino-terminated organic thin films treated with silane agent 3-aminopropyltriethoxysilane (APTES) on a silica dioxide waveguide in a SAW device allows further chemical derivatizations of surface amino groups leading to the introduction of: N-hydroxysuccinimide (NHS) esters, hydrazide and maleimide esters Silica-based substrates containing these grafted chemical groups have been frequently adopted for site-controlled immobilization of biomolecules such as antibodies, during the fabrication of immunoassay-based biosensors.

APTES is often used to form covalent bonds between proteins such as antibodies and insoluble support with very little leakage of proteins from the surface. The construction of layered organized systems has attracted considerable attention due to its ability to attach targeting molecules in biosensors, this application describe a method and its chemical recipes to improve surface adhesion, surface compaction of the antibodies as well as direct self assembled monolayers of spacer molecule to enable the sensing surface with closed compaction of fragmented antibodies on the sensing lane to avoid false negative or false positive results due to contamination of nonspecific attraction to the sensing lane.

In one embodiment the diagnosis for life-threatening diseases such as cancers, generally require a biopsy to be performed. This is, however, a highly invasive procedure. Often this analysis is followed by proteomics and genomics studies that require the use of sophisticated instruments and highly trained personnel for data analysis. As an alternative, physiological changes that occur during illnesses can be analyzed making use of noninvasive procedures. The diagnosis of lung cancer is one such area where the illness can be identified by analyzing the exhaled breath of patients for volatile organic compounds. These molecules include hydrocarbons such as hexane, methylpentane and a number of benzene derivatives.

In one other embodiment, the application addresses the problem of how to reliably measure the degree and time sequencing of a plurality of biomarkers in an aqueous media in real time, where the degree and time sequencing of the plurality of biomarkers in a live cell is mimicked and resolved. This problem is solved by providing an array of SAW cells while employing functionalized sensing lanes, whereby the specific probe, be it antibody, an antigen, a protein, a receptor, an aptamer, a peptide, a DNA strand, or an enzyme are set in a matrix array, incorporating multiple antibodies for the purpose of cross validation and increased reliability of the resultant sensor outputs. A peptide is a linear organic polymer consisting of a large number of amino-acid residues bonded together in a chain, forming part of (or the whole of) a protein molecule. Antibodies and all proteins are formed as a class of peptides. A polypeptide is a chain of amino acids. One end of the change is the N-terminal (amino terminal) and the other end is the C-terminal (carboxyl terminal). Amino acids bond together with peptide bonds in order to form the polypeptide.

The SAW cells are paired as sensor and reference cells in an array, which is coupled through an analog signal processing and computational front end circuitry, and where a digital back end circuit controls the frequency sweep cycling of the array, the data storage and data processing of the cell phase shift magnitude. A phase space density matrix of the plurality of biomarkers can thus be generated from which the diffusion equation of the corresponding underlying cellular biological activities of the corresponding plurality of biomarkers can be solved and statistical counting of hybridization of protein and analyte in real time is achieved.

The binding of these two molecules, antibody-antigen (Ab+Ag), modulates the threshold voltage of a circuit, while changing the frequency and/or amplitude of the circuit. The sensing area is further characterized by a substrate, which enhances the affinity between the antibody molecules and the analytes.

The combined array of SAW units integrally forming a fluid cell is configured to direct the flow the analyte samples onto the active surfaces of a plurality of SAW cells. The array of parallel SAW cells with its sensing area act as bias represented by the phase shift, which is proportional to the mass loading on the surface.

In one embodiment, the SAW biosensor is fitted with an analog front-end (AFE) circuitry enables an analog computational module to measure the sensory output(s) continuously over the time and frequency domains, further enabling detection, analysis, and data-storage which in turn further enables reporting of biomarker hybridization measurements. Moreover, this configuration of the SAW detector array accurately measures a quantifiable rate of change of the analyte/molecules in vitro, providing real time-mimicry of the cellular biomarker(s) hybridization's kinetics, a feature of the invention which enable the apparatus to measure the time constant ($\tau$).

The apparatus and method is further generalized to enable the construction of an analog biological computing device. The embodiment is directed to chemical biosensors with an architecture where each cell of the sensor's array, is formed as a SH SAW and where the sensing area is fabricated as is shown in the embodiments of this application. The cellular network of SAW transducers is further integrated to form an analog computational apparatus by the use of the SAW array within the micro-fluidic-chamber.

The illustrated embodiment of this application shows that the conjugated biomolecules can be detected by the use of a SAW array coupled with an analog interface unit in a manner that efficiently and markedly improves the current art of counting and identifying the sequencing of stochastic biological events, and where the need to identify the timing and location, including statistical measures of hybridization, is essential in uncovering the nature and specificity of cascading effects of protein sequences (including the uncovering of apparent statistical causal correlations.

The illustrated embodiment employs the data generated by measurements conducted on sample protein and reported by "Carbon Nanotube BioFET with a Local Amplifier in a System Array for Analysis of Biomarkers and Method of Analysis of Same", U.S. patent application Ser. No. 12/581, 758 filed Oct. 19, 2009 which is incorporated in its entirety. For example detection of the protein such as $VEGF_{165}$, demonstrates the effective use of the apparatus and its method of detection, including calculating as well as reporting of the results of hybridization in a manner that is not previously observed.

The disclosed process employs a sensor molecule (the probe-analyte antibody combination), as the biasing element attached to the functionalized surface of the SAW, where the sensing area geometry and its charge surrounding the channel of the SAW is changed due to hybridization. This change in charge causes a change in frequency ($\Delta f_0$) of the SAW channel, which shifts the register within the analog front-end circuitry. When the SAW biosensor is biased in the sub-threshold region, (a critical parameter dependent on the geometry and metric of the sensing area design and its LOD), a linear change in the frequency ($\Delta f_0$) due to hybridization of the target molecule results in a corresponding phase shift proportional to mass loading in the sensing area.

In one embodiment, the cellular array of SH SAW's signal output(s) is processed by the analog circuitry and a digital processing unit. The analog computation is significantly more efficient in its use of resources than deterministic digital computation. The disclosed method and apparatus enable counting and recording of the underlying stochastic non-linear events and measurement of biological process which follows the hybridization of the analyte to its target probe and provide information on the sequencing of the biological evolution of the assay, for example, counting how many $VEGF_{165}$-biomarker are available in the sample, by further defining the time constant of hybridization, hence mimicking the diffusion model of protein cascade, the apparatus with its analogue computational machinery is able of mimicking the Boltzmann exponential laws of thermodynamics and by similar logarithmic electrochemical potentials occurring during the biological process of hybridization.

The tracking and mimicking of biological processes is centered on the use of an improved SH SAW cell unit, in which a biosensor of this type combined with circuit operators summing, subtracting, integrating and differentiating the outputs available from the array of the SAW matrix using an analog computation unit, will increase the information content of the measurement(s) by providing the information on the bio-kinetics and other dynamical parameters which are essential in understanding biological process.

In one embodiment, the biosensor (SH SAW) includes a local source follower amplifier to capture low magnitude biological signals in a circuit that measures the hybridization counts. This parameter is used by the apparatus in order to account for the time constant, $$\frac{d\tau}{\tau} = \sum_{i=1}^{n} \gamma_{yi} d\gamma_i,$$

computed by the analog front end thereby enabling a predictive tool acting in parallel by the analog front end and its computational module. The use of the time constant and the coefficient as described formally use the data gathered during the hybridization between the analyte and its antibody while accounting for the "kinetic hits" of the molecule-ensemble-hybridization. A femtomolar threshold setting of the SAW biosensor electronic detection employed by the apparatus, using sample and holds (S/H) measurement at e.g. 10 kHz scan rate thereby using such scan rate in determining the rate of change. The arithmetical unit within the apparatus then compute the time constant $$\left[\frac{d\tau}{\tau}\right]$$

and its derivative while following the detection of label-free processes and where such mass loading on the sensing lane can be estimated by the algorithmic computation module of the apparatus. This embodiment of the apparatus provides a predictable tool to estimate the hybridization curve and further act as a control measure for the comparison of the results obtained by incorporating the individual data points with the results obtained from a least square fitting (LSF) algorithm. This arithmetical process provides for additional validation between the experimental data and the predictive data generated through the process of kinetic time constant analysis.

In one embodiment, the device is realized by forming a matrix array of SAWs acting as parallel detecting' sensors which forms the electrical configuration of adding the parallel hybridization, this feature of the invention allows a realization of a low cost, portable biosensor apparatus as a fully integrated device for detecting, measuring and computing the relevant parameters in an array form.

The present disclosure is directed to a biosensor in the form of an SH SAW cell array and, more particularly, includes a plurality of outputs (phase shift) from an array of an integrated platform of SAWs. It is fabricated using solid state techniques in conjunction with a sensing lane and reference lane operated in a differential mode and where an oligonucleotide element, such as aptamers (oligonucleotide ligands that are selected for high-affinity binding to molecular targets), or alternatively an improved antibody described by the use of a half antibody which provides a mass loading differentiation due to the hybridization on the surface of the sensing area (the delay associated with its respective phase shift relative to hybridization of the analyte and its sensing probe.

In one embodiment of this application the apparatus supports a diagnostic measure, namely to emulate the kinetic growth rate of the sensor hybridization as a function of its analyte level sensed in the SAW sensing area chamber (effective geometry), while measuring the binding rate of the analyte molecules onto the sensing plate. The ability to mimic the vectorial trends of a biomarker(s) binding rate of analyte(s) molecules (biomarkers) is simulated by the equivalent circuit of the apparatus, and further provides an effective tool for recoding biological sequences, thereby enabling a means for reproducing the sequence of which specific analyte within the assay is hybridized while providing the dynamic of conjugation based on the ability of the resident microcontroller to sample and hold (SH) the respective measured output(s). The SAW phase shift or amplitude change mass loading reports are added by the computational apparatus load, which in turn calculate thereby providing an accurate measure for the state of the system in question.

In one embodiment, the SAW cell(s) within the array detect the presence of the biomarker molecules by the use of a mechanism based on an electrochemical binding of an aptamer/antibody suitable to bind to such an analyte, while the reference lane is differentially scanned synchronously with a nonspecific antibody or probe with a similar molecular weight. The antibody basic structure and its molecular weight plays an important role in the accuracy consideration of the SH SAW biosensor as its electrical equivalent of the sensing output is configured as a differential mode phase shift. The basic structural unit of most mammalian antibodies is a glycoprotein with MW ~150,000 Daltons comprising four polypeptide chains—two light chains and two heavy chains, which are connected by disulfide bonds. Each light chain has a molecular weight of ~25,000 Daltons and is composed of two domains, one variable domain (VL) and one constant domain (CL). There are two types of light chains, lambda ($\lambda$) and kappa ($\kappa$). In humans, 60% of the light chains are $\kappa$, and 40% are $\lambda$, whereas in mice, 95% of the light chains are κ and only 5% are λ. A single antibody molecule contains either κ light chains or λ light chains, but never both. The proposed functionalization of the sensor is set to account for the relative molecular weight of the specific probe on the sensing lane and its reference lane to account for their relative magnitude of the nonspecific antibody at the reference lane and the specific antibody at the sensing lane. The biosensor electrical equivalent signal is the result of a differential output between the sensing lane and the reference lane measured as a phase shift or amplitude change due to the added mass due to hybridization on the sensing lane while the reference lane is stable and unchanged.

There are five antibody classes—IgG, IgA, IgM, IgE and IgD—which are distinguished by their heavy chains γ, α, μ, ε and δ, respectively.

In one embodiment of this application, we employ an example of a biomarkers used by the SAW sensing lane(s). The example employed is a demonstration of the SH SAW biosensor in providing a readily available indication for variety of pathogens, viruses, bacteria, protein, cell, DNA, RNA and small molecules without the customary laboratory settings where expensive equipment and trained personnel are necessary in order to perform the diagnostic tasks of identifying, analyzing and reporting of such biological organic or inorganic chemical compounds present within an assay. The application employs one of the known antibody classes in its reference lane where non-hybridizing events provide a stable reference in a differential mode output to identify the phase shift or amplitude change due to the hybridization, and where the device provides for continuous sampling of the hybridization timestamp and phase shift to record the kinetics of mass accumulation over the sensor. This feature of the invention enables the computational unit residing within the apparatus to compute the curve prior to saturation and provide an indication of the mass loading rate of change which can be estimated using algorithmic technique of predicting the exponential based on time constant (τ). This predictive tool provides additional modality of corroboration in parallel to the system response whereby in cases where the analyte quantity is large, and saturation occurs rapidly, the algorithmic predictive tool residing within the apparatus eliminates the problem associated with premature saturation of the sensing lane due to the amount of antibodies packed over the surface.

An electronic circuit and algorithm enable an effective arithmetical procedure to be performed as two distinct electrical measurements in parallel (in a background mode), by measuring time constant T, which further enables prediction of the outcome of the SAW biosensing apparatus in cases of saturation of the sensing lane.

An oscillator generate the appropriate waveform, which travels and excites the surface acoustic, i.e. the transduction from electric energy to mechanical energy (in the form of SAWs piezoelectric materials). The apparatus employs an additional algorithm to measure the rise and fall of the RC network due to hybridization of the analyte and its respective antibody.

The process of this measurement is first to identify the starting and final values of the hybridization based on the threshold value set (as an equivalent quantity of the capacitive change versus time). The starting value is set as "zero" by the circuit, prior to the injection of the analyte into the microfluidic chamber; that is, whatever quantity the reactive component is holding constant.

For the SAW biosensor, the time is defined as "initial value of the calculated variable" and it is equal to the hybridization minimum capacitive change i.e. the limit of detection of the SAW threshold, (LOD). This quantity is noted in the apparatus as the $V_0$ voltage.

When the hybridization starts, a digital "switch" in a circuit mimics the detecting voltage change where it is "closed" or "opened", based on a set voltage change (proportional to concentration of the analyte, e.g. LOD of femtomolar magnitude, equivalent to a capacitor value in microfarads).

The reactive component that drives the circuit attempts to maintain that quantity $V_0$-$V_1$ at the same level as it was before the switch transition, so that value is used as the "starting" value.

The final value is the value of the capacitive loading $C_i$, which is the quantity that represents the total span of the event from rise to fall time, or otherwise described as the delta change of the capacitive value that is asymptotically constant compared with its previously measured value. This can be determined by analyzing a capacitive circuit as though the capacitive change is a maximum for the period measured by the detector, [$\Delta C = C_i - C_{i+1}$] is approximately equal to zero between to and The next step is to calculate the time constant of the circuit: the amount of time it takes voltage value to change approximately 63 percent from their starting values to their final values in a transient situation. In a series RC circuit, the time constant is equal to the total resistance in ohms multiplied by the total capacitance in farads. In this case, the time constant is expressed in units of seconds and symbolized by the Greek letter "tau" (τ)=RC The "rise" and "fall" of circuit values such as voltage in response to a transient is, as mentioned before, asymptotic. Being so, the values begin to rapidly change soon after the transient and settle down over time. If plotted on a graph, the approach to the final values of voltage and current form exponential curves.

As stated before, one time constant is the amount of time it takes for any of these values to change about 63 percent from their starting values to their (ultimate) final values. For every time constant, these values move (approximately) 63 percent closer to their eventual goal. The mathematical formula for determining the precise percentage is:

$$\text{percentage of change} = \left(1 - \frac{1}{e^{-t/\tau}}\right).$$

Where e, stands for Euler is constant, which is approximately 2.7182818. derived from calculus technique, mathematically analyzing the asymptotic approach of the circuit values. After one time constant's worth of time, the percentage of change from starting value to final value is:

$$\left(1 - \frac{1}{e^1}\right) \times 100\% = 63.212\%,$$

$$\left(1 - \frac{1}{e^2}\right) \times 100\% = 86.386\%,$$

$$\left(1 - \frac{1}{e^{10}}\right) \times 100\% = 99.995\%$$

The process of measurement and calculation is repeated during the entire time the SAW biosensor is active in detecting, recording and analyzing the biological payload within the microfluidic chamber 139, and the more time that passes since the transient application of voltage from the SAW biosensor 34, the larger the value of the denominator in the fraction, which makes for a smaller value for the whole fraction, which makes for a grand total (1 minus the fraction) approaching 1, or 100 percent.

The expression of change is equal to:

$$(\text{Final} - \text{Start}) \cdot \left(1 - \frac{1}{e^{-t/\tau}}\right).$$

Where "Final" is the calculated variable of hybridization after the comparator residing at the microcontroller indicates that the $\Delta C$ is approaching a small variation of capacitive change (in microfarads). The Initial value of the calculated variable is set at the initial startup of the system and prior to any change in capacitive loading on the circuit. e, is equal to (2.7182818), t, is the time in seconds and $\tau$, is the calculated time constant.

FIGS. 10 and 10A are graphic depictions with an exponential decay of the RC network representing a typical hybridization of analyte with its antibody, where circuit 121 switches "off" and "on" its output 106 (phase shift Measurement step), using its saturation detection circuit 911 to measure the time constant $\tau$. This procedure is a depiction of the SAW biosensor output 48 where the RF driver 96 (oscillator) circuit with its electronic detector 911 and its resident microcontroller 901, measure and analyze the square-wave output from the function generator, the peak-to-peak voltage to at least X volts and as noted by the position of the waveform.

The process of analyzing the time constant T is calculated by the arithmetical module 300 and data strings are presented to the microcontroller. The process is graphically shown in FIG. 7A.

Time constant measurement provides the apparatus 1 and 34 a measure for computing the exponential curve and predicting its nature to solve the problem of saturation due to a boundary condition's case associated with an event, where the amount of antibodies on the sensing lane 129, is insufficient to account for a massive quantity of the analyte present in the sample.

By the use of Saturation Detection step and the time constant measurements, the system and its algorithm are enabled with the information to predict the final value present within the sample analyte, thereby predicting the outcome based on the time constant and its coefficient of expansion $\gamma_{yi} d\gamma_i$. Employing the Maclaurin series expansion $$\frac{d\tau}{\tau} = \sum_{i=1}^{n} \gamma_{yi} d\gamma_i,$$

the algorithm computes the time constant ratio $$\frac{d\tau}{\tau}$$

in the expression, while the system reduces its derivative to its coefficient value $\gamma_{yi}$, thereby enabling the a measure of the rate of change (its derivative) and by such use of the coefficient the arithmetical computation module generates the predicted outcome's curve. The apparatus and its sensing mechanism as a parallel method to improve detection of label-free processes and further to enable a mass loading estimate of sensing lane by the algorithmic computation module of the apparatus use this process.

In one embodiment, we employ the example of near real time, label free detection of a vascular endothelial growth factor, (VEGF$_{165}$) which plays a critical role during normal angiogenesis and in the pathological angiogenesis that occurs in a number of diseases, including cancer, angiogenesis is a hallmark of wound healing, the menstrual cycle, cancer, and various ischemic and inflammatory diseases. Vascular endothelial growth factor (VEGF) is an inducer of angiogenesis and lymph-angiogenesis, because it is a highly specific mitogen for endothelial cells. Signal transduction involves binding to tyrosine kinase receptors and results in endothelial cell proliferation, migration, and new vessel formation. The application of the SH SAW biosensor in diagnostics enables detection of how modulation of VEGF expression creates new therapeutic possibilities and describes recent developments in this field.

Initial attempts to block VEGF by using a sensory apparatus are limited by the complexity and length of processing times associated with the current art. The use of the apparatus to detect the humanized monoclonal antibody bevacizumab (Avastin, Genentech/Roche), and two kinase inhibitors sorafenib (Nexavar; Bayer) and sunitinib (Sutent, Pfizer) which target the VEGF receptor (VEGFR) tyrosine kinases, is essential, since such steps are beginning to show promise in human cancer patients, including the ability to optimize VEGF blockade. Therefore, a portable in vitro or in-vivo device that accurately provides real-time feedback on VEGF levels is able to regulate, attenuate or modify the intake of anti-angiogenic-agents is needed for any finely tuned anti-angiogenesis therapy.

The illustrated embodiment is capable of measuring VEGF levels by emulating the process where VEGF molecules binds to an immobilized VEGF aptamer antibody within a known time domain, providing an appropriate feedback based on the VEGF level in any regulated diagnostic and/or therapeutic procedure where such a measure is used for treating malignancy.

In one other embodiment, we employ interactions between VEGF protein and their receptors as the respective binding of the aptamers or antibody and the VEGF receptor within the controlled conditions in the apparatus microfluidic chamber, and demonstrate the effective use of such embodiment and its usefulness relative to the prior art. Details of signaling events and their biological outcome are concisely illustrated by simulating the binding rate of the for example a VEGF molecule-binding to the aptamer or its antibody present in the apparatus' chamber; hence, such a parallel process of detecting as well as counting of such biological processes, provides the necessary quantitative trends and concentration values in the equivalent circuit of the apparatus.

The application, describe the method of the proposed VEGF SH SAW biodetection, using the improvements made in technique and equipment for fabricating miniature devices such as; the geometry of the SAW and its ancillary analog front-end or its hybrid digital module, and consequently, the improvements in silicon fabrication and high-precision micro-electromechanical systems (MEMS), which enable such apparatus. Specifically, the application is directed to the novel and improves bio chemical conjugation techniques defined by detail description of the embodiment described in this application as "Functionalization of SH SAW-sensing Lane".

In another embodiment, the SAW cell fabrication technique employs an electrical polarity seeding, to naturally attract the intrinsically negative electric charge of, for example, vascular endothelial growth factor (VEGF) molecules, while further modulating the threshold voltage of the circuit. This and many other examples used throughout this application are employed as illustrations of the preferred embodiments, but one familiar with the art of analytic chemistry and electronics can find other suitable examples to illustrate the method presented.

In another embodiment, the electrical polarity can be modulated to attract and then release the VEGF molecules to prevent a buildup of ionic molecules on the sensor surface (the layering of spacer molecules and closed compaction of fragmented antibodies on the sensing lane to avoid false negative or false positive results due to contamination of nonspecific attraction to the sensing lane, hence altering the mass loading of the sensor) while preventing sedimentation and nonspecific bindings of ionic residue within the buffer solution, thereby enabling a continuous flow of biological fluids flowing through the SAW microfluidic chamber.

In another embodiment, the SAW IDT is fabricated with a preferably p-doped Si substrate to enhance the affinity between the e.g. VEGF molecules and the antibody or aptamers causing the change in the impedance (due to capacitance loading) of the circuit containing the SAW cell array. The array is configured to provide an unobstructed flow of the VEGF samples on the active surface of the sensing lane, due to its use of flow's geometry layout.

In one embodiment, the device is formed, as an array of parallel IDT's, which act as integrated individual counter-electrodes. The device is further equipped with a computational apparatus to render the sensory outputs over the time domain, resulting in detection of the analytic data of specific hybridization with its time stamps. This feature arises from the signal fidelity provided by connecting the electrical output(s) of the SH SWA to a source follower amplifier configuration. The apparatus is further integrated with A/D converter, resulting in a computation device based on a sampling algorithm for reporting on the statistical slices of time-domain activity as well as frequency domain changes resulting from the hybridization kinetics.

In another embodiment, the device can provide an accurately measured and quantifiable rate of change of VEGF molecules in-vivo and enables for example an improved diagnosis of tumor markers. As a result of such information (VEGF level and vectorial trends), the device with its auxiliary circuit improves the diagnostic capability of the medical staff in providing an early detection of minute changes of a quantifiable biomarkers within the blood, hence improving the odds of therapeutic outcome by providing base statistics, without the lengthy and expensive labeling techniques known in the art as enzyme-linked immunosorbent assay (ELISA).

In one embodiment of the proposed SH SAW biosensor, the immobilized binding group is located in one or more areas on the surface of a sensing lanes whose locations on the membrane, sizes and area immobilization densities are designed to maximize the observed frequency and/or amplitude shifts in the target analyte binding and to maximize the discrimination between all combinations of specific and non-specific binding. This discrimination may take three forms: (a) change in resonant frequency of the effective area formed on the sensing vs. reference lanes with the immobilized chemical linker, (b) appearance or disappearance of a higher order harmonic shift, or (c) change in amplitude decay rates, a process detected by the analog front end of the proposed apparatus. In such a biosensor (a unit cell comprised of a SAW is alternatively be loaded with plurality of antibodies/antigens), a single array of SAW units may be comprised of a plurality of individually addressable elements for actuation and for sensing purposes, as well as comparative measurement relative to timing and density of processes occurring within the cells. This technique permits the specific measure of the sequencing order(s) of selected modes and enables simultaneous actuation of an alarm circuit or like devices. The principles of measuring biological cascading effects (of multiple proteins within the analyte), is essential parameter in uncovering the interdependence of causal statistics in the relation between the different biological species simultaneously available in the analyte.

In one embodiment, a simple and robust, as well as reversible method is provided which can reliably detect in one operation an analyte molecule.

An object of the illustrated embodiment is achieved according to at least one embodiment by binding of specified analytes in a sequence of method steps by using the SAW cell.

In at least one embodiment, measurement is carried out in each case after the antibody is bound to circulating analytes, and its electrical value is counted in the time domain, stored, and reported.

At least one device for monitoring and controlling the hybridization of, for example, VEGF molecules over the matrix array positions of the sensing lane and one device for controlling the rate of liquid flow in the associated detection device are present in the embodiment of the proposed apparatus. For this purpose, the sensor lane is connected to a microfluidic system.

Various embodiments relating to signal amplification methods for multiple biological assays is employed by the invention. In one of the preferred embodiments, the SAW cell or its array is electrically connected to a source follower amplifier (SFA) where the amplification of a low-level signal is augmented. In another embodiment, the signal amplification is inherently biological in nature where the substrate of the sensor formed out of silica dioxide ($SiO_2$) is functionalized with a dense packing of the antibodies. The signal amplification is further enhanced by the use of linker group formed on gold nanoparticle(s) GNP-Au. The nanoparticle-based nanostructures produce an elaborate label-free mass sensing device.

The biological target complexes are tagged by a seed substance GNP-Au on the a surface-enhanced substrate, such that organic or in organic aptamers or antibody, cell, DNA, RNA, virus or bacteria, protein or small molecule are tagged and provide a multi-epitope, thereby increasing the capture statistics by an order of magnitude. The process of layering the functionalized GNP with its engineered probes follows the procedure described by this application. The target complexes then bind the capture reagents with its antibody. The SH SAW due to its added mass, which is represented by an increase phase shift or amplitude change, then senses the hybridized complex. This application employs the method of signal amplification by employing electrical techniques known in the art as well as its novel engineered probes due to its use of encoded DNA encoded sequences to increase the native biological signal thereby reducing the LOD to a femtomolar concentration.

Accordingly, in one embodiment, a biological target complex including a target analyte associated with a first specific binding member is provided. The target complex further includes a second specific binding member that binds to the first specific binding member forming a target complex. The second specific binding member includes a seed particle suitable for catalyzing the formation of a surface-enhanced aptamer or antibody such as a VEGF. Subsequently, the complex substrate can be activated by means of the electronic circuit to provide the necessary change in impedance, frequency shift, and amplitude change in a differential mode.

In one aspect, the invention includes a SH SAW sensor apparatus emulating a binding event between a ligand and ligand-binding agent. The apparatus has a SAW surface composed of chemical linker suitable for the targeted molecule(s), and two-subunit heterodimer complexes carried on the surface. The complexes are composed of a first and second, preferably oppositely charged-peptides that together form α-helical coiled-coil heterodimer. The first peptide is attached to the SAW surface, and a ligand is covalently attached to the second peptide, accessible for binding by a ligand-binding agent. The SAW sensing lane (array) detects binding of an anti-ligand agent to the ligand and the signal is enhanced by the electronic circuit such as a source follower amplifier.

In one general embodiment, the SAW surface includes a monolayer composed of chemical chains anchored at their proximal ends to the SAW surface, and having free distal ends defining an exposed monolayer surface. The heterodimer complexes in this embodiment are preferably embedded in the monolayer with chemical linker as shown by the SAW functionalization methods, where in one illustrated option an epoxide nucleophilic substitution chemistry is employed and where amino-modified aptamer can be covalently linked to the poly (glycidyl methacrylate) (PGMA), or an alternate process of functionalization of the active surface is achieved using pyrene through π-π interactions, where a non-covalent functionalization of the active surface can be achieved using pyrene and pyrene derivatives. Many other variations, such as covalent immobilization of antibodies to carboxyl groups through amide linkage can be used and are described by the figures and their accompanying descriptions. All the above methods of functionalization of the sensing lane(s) of the SAW biosensor are illustrations for use by the apparatus, to improve the LOD to set a minimal limit at a femtomolar concentration level. The functionalized linker group as noted above, comprises a monolayer surface, the monolayer may be formed alternatively on a metal, e.g., gold film, aluminum, and may be composed of a monolayer surface with a thiol group linkage.

In one embodiment, the proposed apparatus contains a chamber, which is adapted to contain an aqueous solution of redox species in contact with the monolayer, and the detector includes a circuit for measuring ion-mediated current across the monolayer, in response to binding events occurring between the receptor and ligand.

More generally, we disclose construction of an array of different, selected biological reagents attached to different, selected regions on an assay support surface comprised of the SH SAW connected electrically to source following amplifier which form the basic unit of the analogue signal chain resulting in an electrical output(S) equivalent to the binding events occurring at the sensing surface of the SH SAW biosensor.

In one embodiment a micro-machined or printable structure (cavity), is generally formed using a semiconductor substrate such as a silicon wafer. One of the objects of the present invention is to realize further reduction in cost by integrating a minute structure and a semiconductor element controlling the minute structure over one insulating surface in one-step. A minute structure has a structure in which a first layer formed into a frame-shape is provided over an insulating surface, a space being formed inside the frame, and a second layer is formed over the first layer. Such a minute structure and a thin film metalized IDT can be integrated on one insulating surface in one-step.

Further improvements of the device are illustrated by the architecture of the SAW, where the hybrid construction of the substrate and its geometry (the sensing and reference ID's on the $SiO_2$ substrate) are formed to enable a transduction of the hybridization between the antibody and the analyte, while mimicking the biological process dynamics, and as it is described and realized by the cavity geometry and the electrical characteristics of the SAW.

In one embodiment the SAW is constructed as an independent cell out of an active array of elements in the form of a matrix, resulting in an effective analog computation device, where each of the cell unit (SAW resonator) reports to a resident microcontroller of the event activity and is summed, integrated or undergoes the process of measurement and counting via the arithmetical of the proposed apparatus.

The aim of the apparatus is to measure and mimic the hybridization process between antibody(s) and analyte(s) by further providing a means for counting/measuring such processes while emulating biological kinetics' process with mathematical analogs such as known in the art as: counting, summation, integration and differentiation.

Some embodiments demonstrate the advantages of the SAW architecture compared to the traditional optical methods as well as existing field effect transistor (FET), where a direct, label-free, (near) real-time, continuous signal is obtained, and where highly selective sensing is used followed by the binding between an antibody and an antigen, achieving a specificity with resolution and accuracy which is improved over the current art. The above state of improved device characteristics is due to its higher surface-to-volume ratio of the sensing surface in the sampling cell and thus an increased modulation of the conductance by the biomolecules. A concentration dependent increase while the phase shift or amplitude changes is directly connected to a source follower amplifier and where the source-drain current is observed in the regime of clinical significance with a detection limit of approximately 30 fM (450 pg).

In one embodiment, the surface area of the sensing lane between the IDT's resonators is minimized, hence the amount of the required analyte concentration is proportionally reduced, and this feature of the invention minimizes the amount of analyte needed in performing the measurement. Due to such construction, the device characteristics (DC) offer an order of magnitude increase of analyte/antibody statistics of covalent matching and the SAW cell sensor benefits from further miniaturization and increased detection rate. The improvements in device characteristics are due to the lithographic process employed and the integration of the metalized IDT's over the microfluidic chamber similar to the integration of field effect transistor fabrication, which enables sensing protein-protein interactions, and protein interaction mechanisms. These improvements are due not only to the sheer fact of the device characteristics of real-time and a label-free detection, but also to its high sensitivity and selectivity, whereas the IDT geometry increases mobility and facilitates transportation by improving the spatial opportunity access of the analyte and its antibody as the assay travels through the SAW internal microfluidic chamber. The statistical indices of accelerated hybridization are due to the electrical design of the sensing lane(s), which further increases propulsion of antibody/antigen, due to molecular affinity of the cytoskeleton specificity of the analyte and the antibody.

In one embodiment, the topological layout of the SAW sensing lane is described where the length as well as the thickness is proportional to its wavelength and its guiding layer has a waveguide coating.

These and other features of the illustrated SAW enable an accurate, near real-time computation of the data generated by the transducer action by the label free SAW cell and its peripheral electronics, to define the time constant $\tau$ (tau) of the measured process. This embodiment is enhanced by high sampling rate by the use of a resident microcontroller, achieving an accurate and consistent count of hybridization rate on a scale consistent with medical diagnostic values having a resolution of 1 pg/mL (3.671 pmol/L), while measuring the analyte flow through the SAW's microfluidic chamber.

Many studies outlining the quantitative correlation of serum levels and tumor expression of vascular endothelial growth factor (VEGF) in patients indicate that those serum levels of VEGF may provide useful prognostic information in patients with various types of cancers. The ability to measure such vectorial expression can provide a prognostic as well as therapeutic tool in the hands of the physician (oncologist). To enable such resolution and accuracy of the measuring apparatus, it must be capable of resolving the process of hybridization product with magnitude of 40 pg/mL minimum, to achieve the degree of statistical confidence required.

In one embodiment, the operation of the SAW in a conducting buffer environment demonstrates that the device characteristics improve the relation between the $V_{ds}$-$I_{ds}$ output due to its electronic scheme. The SH SAW sensing lane coupled with its reference lane (functionalized with a nonspecific class of antibodies such as IgG, IgA, IgM, IgE and IgD) formed in a differential amplifier mode, readily responds to changes in the local environment. Such effects have been demonstrated by this application as noted in its incorporation of the prior art as well as its clinical studies which validate such application of the proposed modification to the prior art.

In one other embodiment the substrate ($SiO_2$) of the biosensor was coated with layers of poly (glyceryl methacrylate) (PGMA), employing self-assembled monolayer (SAM), where a $VEGF_{165}$ molecules and linker (thiol group) was studied and tested by the authors, resulting in an improved properties of adhesion.

In one embodiment, the SAW topology enables reduction in variation between the different devices fabrication due to the ease in a one-step production technique, associated with the construction and functionalization of the SAW's chemistry, as it is further annotated by the figures and their accompanying descriptions.

In one embodiment, the apparatus addresses the problem of biomolecular time-scales, which undergo a variety of fluctuations and conformational changes that span several orders of magnitude. This feature of the invention is related to the analog front end (AFE) which employs a logarithmic amplifier, which linearized the output where the compression of wide dynamic range is available when measuring fast hybridizing biomolecular events.

The ability of such studies (measuring repeatedly in short time intervals) is limited by the fact that local, real-time in vivo/in vitro's measurement of the VEGF level is limited and the needs for such an embodiment and its usefulness is described by the method and apparatus presented, and where the SH SAW biosensor enables repeated measurements of the patient without the customary use of laboratory equipment and trained personnel, while achieving an indication of a process involving VEGF, and Flk-1/KDR RTK; The process described above can benefit from the invention as this biological exchange has been implicated as the key endothelial cell-specific factor signaling pathway in which pathological angiogenesis-including tumor neovascularization is present. This type of measurement can assist in some therapeutic applications, where inhibiting the VEGF tyrosine kinase signaling pathway, blocks new blood vessel formation in growing tumors, thereby leading to stasis or regression of tumor growth. Advances in understanding the biology of angiogenesis have led to the development of several therapeutic modalities for the inhibition of the VEGF tyrosine kinase-signaling pathway. A number of these modalities are under investigation in clinical studies to evaluate their potential to treat verities of the VEGF transduction, where a label-free, real time indication and low cost can use the invention in improving therapeutic outcomes. This and other biological processes can be improved by employing the disclosed method and its implementation. By using the disclosed apparatus, the sequencing and its time stamps can be emulated in evaluating tumor progression, activation of VEGF pathways that promotes tumor vascularization, facilitating tumor growth and metastasis. Abnormal VEGF function is also associated with other diseases including atherosclerosis, psoriasis, age-related macular degeneration, diabetic blindness, rheumatoid arthritis, and hyperthyroidism. The members of the VEGF and VEGF-receptor protein families have distinct but overlapping ligand-receptor specificities, cell-type expression, and function of VEGF receptor activation which in turn regulates a network of signaling processes in the body that promote endothelial cell growth, migration, and survival. The ability of any apparatus to differentiate such a complex assay requires an apparatus that can emulate and mimic the stochastic-statistical hybridization of the protein and its sequences, a task that these application addresses, by employing a label free, hand held device with the embodiments annotated by the figures and the descriptions, which follow.

These and other objects and features of the invention will become more fully apparent when the following detailed description of the invention is read in conjunction with the accompanying drawings.

BRIEF DESCRIPTION OF THE DRAWINGS

The following description of the invention is provided to facilitate an understanding of some of the innovative features unique to the present invention and is not intended to be a full description. A full appreciation of the various aspects of the invention can be gained by taking the entire specification, claims, drawings, and abstract as a whole. Additional objects and advantages of the current invention will become apparent to one of ordinary skill in the art upon reading the specification.

The accompanying drawings in which like reference numerals refer to identical or functionally-similar elements throughout the separate views and which are incorporated in and form part of the specification, further illustrate the present invention and together with the detailed description of the invention, serve to explain the principles of the present invention.

FIG. 11A is a molecular diagram of the interaction between the aptamer and single-strand oligonucleotides.

FIG. 11B is a molecular diagram of how aptamer binds antigen on the active surface forming the substrate of the SAW sensing lane.

FIG. 12A-12C are molecular diagrams of the capture of analyte, proteins and microorganisms with the SAW sensor.

FIG. 22(A) is the summing amplifier, FIG. 22(B) the difference amplifier, FIG. 22(C) the integrator, and FIG. 22(D) the differentiator.

DETAILED DESCRIPTION OF THE PREFERRED EMBODIMENTS

Principle of Operation of Saw Devices
Surface Acoustic Wave-Sensor-Boundary Conditions The aim of this introductory section is to set the theoretical as well as engineering guidelines to achieve a biosensor platform where the limit of detection (LOD) is capable of detecting an analyte concentration in femtomolar level. Setting the boundary conditions for such an objective must include the elements, which form the sensor construction, be it the physical characteristics of the resonator, the crystal oscillator, the geometry of the interdigitated electrodes, the chemical probes and their functionalization as well as the biological probes, which determine the sensor specificity. These facts and other considerations in forming such a platform is further complicated by the fact that biological signal measurements are sensitive to the kinetics of hybridization where such information is essential in evaluating the resultant data.

This application addresses the boundary conditions, which lead to the fabrication of an improved analytical biosensing, label free platform. It further addresses the theoretical as well as the engineering considerations in fabricating a low cost, label free, SH SAW biosensor for field deployment.

The apparatus and its embodiments demonstrate a LOD of biological payloads where the aim of the novel construction of the biosensor platform is to enable an LOD measure with femtomolar concentrations. The detection limit, lower limit of detection, or LOD, is the lowest quantity of a substance that can be distinguished from the absence of that substance (a blank value) within a stated confidence limit (generally 1%). Lee et al, in a study titled "Surface acoustic wave immunosensor for real-time detection of hepatitis B surface antibodies in whole blood samples". 2009; 24:3120-3125. [PubMed], have demonstrated an application of low-wave mode SAW immunosensor to detect an HBs antibody in aqueous conditions. The resonance frequency shift has been monitored to detect specific binding of HBs antibody to the immobilized HBsAg. The sensor shows binding specificity to HBs antibody and a linear relationship between the frequency shift and antibody concentration with sensitivity of 0.74 Hz/(pg/µL) and detection limit <10 pg/µL. The SAW immunosensor can successfully detect HBs antibody in whole blood samples without any pretreatment. This and other studies indicate that the LOD measure in clinically relevant concentrations can be improved if the complex boundary conditions of sensor fabrication are defined and their parameters accurately determined. This process involves the proper selection of the crystal lattice, the metallization of the IDT, as well as the selection of biological or inorganic probes, compaction of the antibody pairing, and the electronic circuit that captures the biological events through a series of amplification and data capture.

Figure 1:
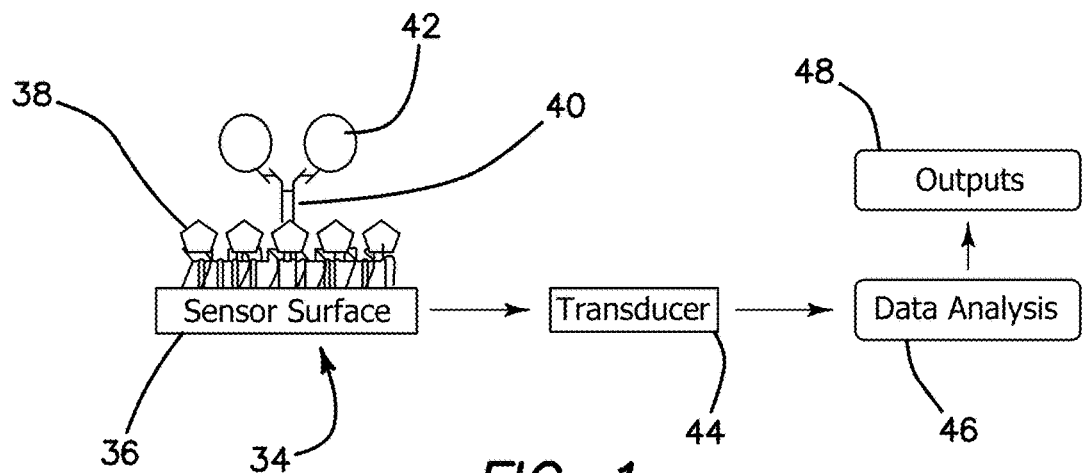
FIG. 1 is simple representation of a biosensor. Full-length antibodies are captured by an organosilane linker on silica dioxide for immobilizing protein in solution.

An overall schematic of the components of the biosensor is shown in FIG. 1. The biosensor 34 includes a functionalized sensor surface 36 where the analyte 42 is recognized and bound using a bio-recognition element 40, which is bound to a surface functionalized agent, here shown as 3-aminopropyl triethoxysilane (APTES). A transducer 44 converts the detected binding event into an electrical signal, which is conditioned or analyzed by a processor or data circuit 38 and then communicated to the biosensor output 48.

Figure 1A:
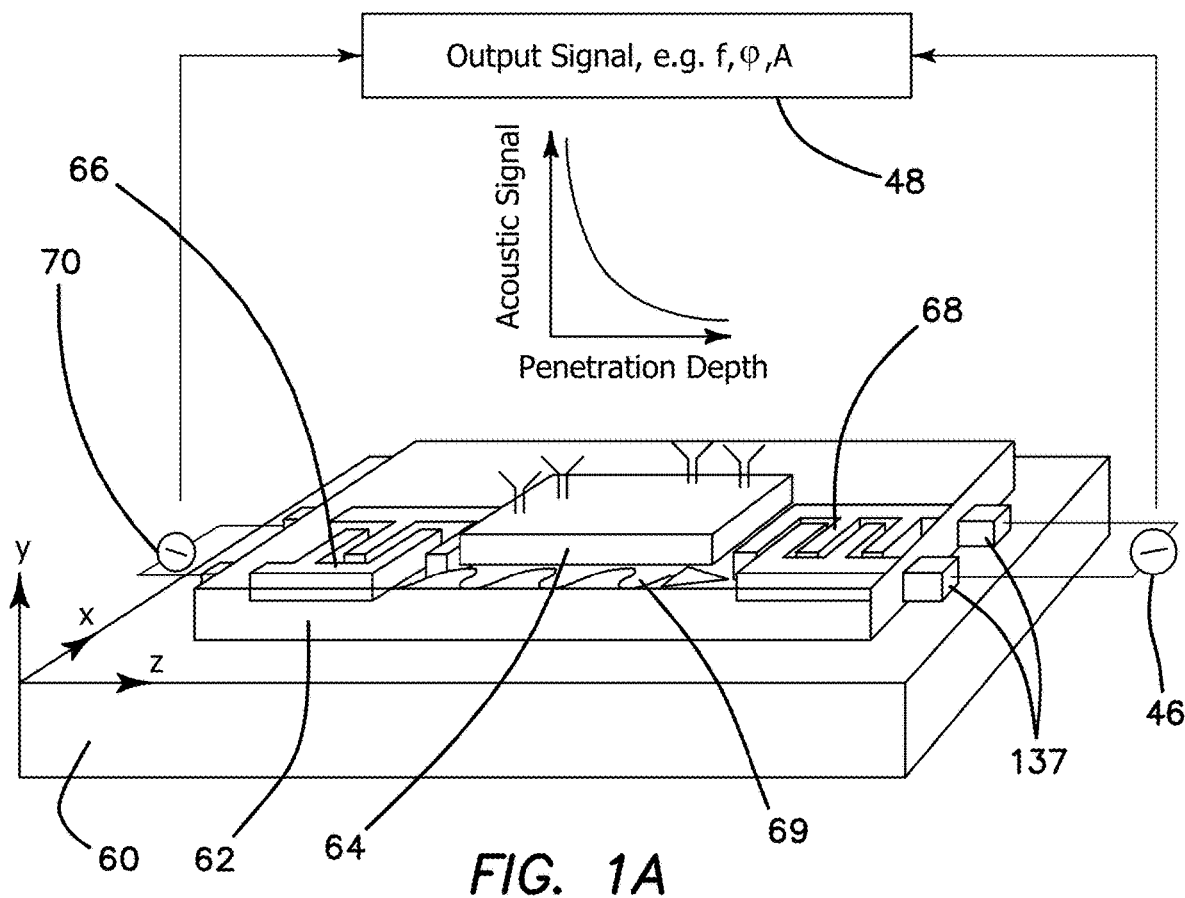
FIG. 1A is a surface acoustic wave device with a single delay line, fabricated on a piezoelectric substrate. The output signal is compare to the signal from a reference lane and the phase, frequency or amplitude differences determined using a mixing cell.

The operation of the SAW device of FIG. 1 is based on acoustic wave propagation near the surface of piezoelectric solids diagrammatically depicted in FIG. 1A. A piezoelectric substrate 60 has a guiding layer 62 formed thereon in which there is an input interdigitated transducer (IDT) 66 and output interdigitated transducer (IDT) 68 comprising transducer 44 of FIG. 1. Between IDTs 66 and 68 is a sensitive layer 64, which may be a functionalized gold layer. An RF driver 70 creates the SAW waves in the guiding layer 62 by means of IDT 66, which are then transmitted or launched into sensitive layer 64, which will be loaded by the detected analyte. The output IDT 68 is excited by the modified SAW wave, and transduces it into an electrical signal, which is detected in data circuit 38 and then communicated to output 48 as the frequency, phase and/or amplitude of the modified SAW wave. The wave can be trapped or otherwise modified while propagating in a traverse mode in layer 64. The displacements decay exponentially away from the surface, so that the most of the wave energy is confined within a depth equal to one wavelength.

The interdigital transducer 66, 68 is comprised of a series of interleaved electrodes made of a metal film deposited on a piezoelectric substrate. The width of the electrodes usually equals the width of the inter-electrode gaps (typically ~0.3 µm) giving the maximal conversion of electrical to mechanical signal, and vice versa.

Controlling the covalent bonding of antibodies onto functionalized substrate 64 using a SH SAW platform is a key step in the design and preparation of label free-based transducer for targeting cancer cells, biomarkers and synthetic oligonucleic acid or peptide. The chemical biosensors forming the sensing substrate 64, their chemical probes and architecture (cellular arrays) which undergo the conformational electrical impedance (phase shift) changes due to hybridization of bioagents is realized with resolution on a scale of femtomolar increments.

Devices of the type illustrated in FIG. 1A are provided as pairs, one as a sensing lane and the other as a reference lane. Whereas the prior art SH SAW transducer controls the mass loading of the analyte and its targeted probe (namely an antibody, an antigen, a protein, a receptor, an aptamer, a peptide, a DNA strand, or an enzyme) by hybridization of the analyte to its specific antibody, thereby changing the mass loading on the sensing and reference lanes, the illustrated embodiments center on the ability of the transducer's design to control the boundary conditions parameters, thereby leading to contributing effects that improve the signal-to-noise ratio of the resultant measured output, which is represented by the phase shift in the frequency domain and its time constant.

The complexity associated with the optimization of such an apparatus is determined by the variability and characteristics relating to the crystal type, waveguide design, waveguide delay layer, microfluidic acoustic properties, analog front-end circuitry, interdigitated electrode, frequency domain characteristics and the use of chemical functionalization of the biological probe.

This task is further complicated by the fact that a label free, near real time response of such a device, for the detection of an antibody, an antigen, a protein, a receptor, an aptamer, a peptide, a DNA strand, or an enzyme requires a careful analysis of the contributing factors, which impact the resultant phase shift as a consequence of the mass loading on the sensing lane. The illustrated embodiments solve some of the limitations of the prior art by sorting the primary contributing factors which enables us to detect and reliably measure the degree and time-sequencing of a plurality of biomarkers in a microfluidic chamber.

In FIGS. 1 and 1A, full-length antibodies are captured by an organosilane linker on silica dioxide for immobilizing protein in solution. A monolithic SAW biosensor system is fabricated on a lithium tantalite substrate ($LiTaO_3$) that utilizes the strategies outlined in FIG. 1 for conducting real-time or near real-time detection of pathogen, disease biomarkers and coupled with an electrochemical system for rapid nucleic acid analysis. The SAW biosensors are specifically targeted towards the detection of whole microbial pathogens, protein biomarkers and nucleic acid in a biological matrix. The illustrated SAW biosensors provide relevant information for patients who are likely to respond to a given therapy, as well as biomarkers that have the ability to measure a patient's response to therapy. These two measures are necessary for personalizing the drug treatment for each patient. The SAW devices will provide preventative information with respect to rapid, point-of-care detection of biological contaminations or infection. One example is in the field of food safety, namely monitoring food quality before food items are consumed.

The use of interdigitated gold acoustic wave biosensors on lithium tantalite substrates presents platforms ideally suited as label-free biosensors for aqueous-based samples. This general technology has been used extensively as a portable, rapid and sensitive detection system for decades, primarily in the telecommunications industry. Recent advancements in the technology, has allowed for the creation guided shear surface acoustic wave (SAW) devices that can operate in liquid environments. These devices can be functionalized through immobilization of antibodies or antibody fragments to target biomarkers to dramatically enhance the use of this system over previous generation of SAW devices. This involves enhanced surface chemistry techniques along with methods of attaching antibody fragments that bind specifically to biomarkers for various diseases.

When performing SAW biosensing in liquid environments for the detection of microbes, eukaryotic cells, protein biomarkers or nucleic acid sequences, there is a strong loss of longitudinal bulk modes such as Raleigh surface waves and most Lamb-wave modes. Surface waves with displacements normal to the surface generate compressional waves, which dissipate wave energy in the liquid. For this reason, acoustic waves that have the particle displacement parallel to the device surface and normal to the wave propagation direction are essential. These waves, which are referred to as shear-horizontal (SH) waves, propagate without coupling acoustic energy into the liquid. SH type acoustic waves include thickness shear modes (TSM), acoustic plate modes (APM), surface skimming bulk waves (STW), Love-waves, Leaky surface acoustic waves (LSAW) and Bleustein-Gulyaev waves. In particular, Love-waves are SH waves that propagate in a thin guiding layer on SH-SAW devices. If a no-slip boundary condition is assumed at the sensing surface, a thin layer of liquid becomes entrained with a shear movement at the surface for viscous liquids. This viscous loading affects the Love-wave in two ways. First, the entrainment results in mass loading of the wave-guiding layer, resulting in changes to the wave number. Second, the wave becomes damped due to viscous losses in the liquid. To reduce aqueous effects, the guiding layer can be shielded in gold to prevent electrical loading of the IDTs. Love-wave that are SH are confined to the thin layer between the wave-guides with the requirement that the shear velocity in this guiding layer (the velocity in the material forming the wave-guides) is less than the shear velocity in the piezoelectric substrate. For this reason, the waveguide is the most significant structure for proper Love mode operation as a mass-sensitive biosensor.

SAW sensors are well known to offer high surface-mass detection sensitivity for chemical sensing. It is possible to measure mass sensitivities from surface loading in the 1-100 $ng/cm^2$ range. The traditional configuration of SAW devices involves a chemically functionalized area that immobilizes a targeted species with a selective surface coating. The attachment of the targeted species perturbs a propagating surface acoustic wave that is generated by the interdigitated (IDT) gold electrode. The system also uses a reference line, which uses an antibody that is not specific to the target. This reference line is used to account for non-specific binding on the sensing area. The acoustic wave is detected by a second set of IDT 68 located across from the first set of IDT 66. If the targeted species is present, then the propagating wave will be perturbed in such a way to cause a shift in the phase, frequency or amplitude, relative to wave that propagated across the reference electrode. This configuration is illustrated in FIG. 1A. These miniature biosensors are often used in an array format where multiple delay lines can be scanned for a single target in parallel, but the device could also be operated in series to scan for multiple biomarkers for different diseases. Operating a SAW array allows rapid, point-of-care diagnostic using small portable devices. The use of miniature monolithic SAW sensor arrays allows on-chip signal processing, and allows the chips to be fully integrated into a larger system and can be easily packaged.

Temperature compensation is inherent to this system since the SAW's reference and the sensing lanes are on the same substrate and therefore experience the same temperature fluctuations. Therefore, any adjustment to the phase due to temperature fluctuation is automatically adjusted. The determination of the phase shift is determined by using homodyne mixing using a Gilbert cell mixer. The mixer extracts the difference in phase between the resonance frequency from the reference and the resonance frequency of the delay line being probed. The resulting phase shift is then calibrated for changes in the mass loading of the surface. This process cancels any temperature dependence. Measurements in all lanes are differential measurements relative to the reference line. Both the reference and the delay lines experience the same changes since the reference lanes are essentially a built-in control.

In a surface acoustic wave device with a single delay line, fabricated on a piezoelectric substrate, the output signal is compared to the signal from a reference lane and the phase, frequency or amplitude differences determined using a mixing cell.

Antibody-based coated SAW biosensors permit the rapid and sensitive analysis of a range of pathogens and their associated toxins. The presence of bacterial pathogens, fungus and viral particles are ubiquitous in our environment and can pose considerable risk to persons, who are exposed to these pathogens. Therefore, monitoring for the presence of microorganisms will be critical for maintaining proper health. This is especially true for short shelf-life foods. Mass-based piezoelectric biosensors operate on the principle that a change in the mass, resulting from the molecular interactions between a targeting molecule and the target can be determined. For example, mass changes result in alterations in the resonance frequency of a lithium tantalite crystal. These piezoelectric sensors are affordable and disposable options for pathogen and biomarker detection.

Outbreaks of food-borne and water-borne pathogens remain a major cause of disease and mortality throughout the world. The rapid detection of these pathogenic microorganisms is critical for the prevention of public health epidemics. The quantitative identification of microorganisms has become one of the key points in areas of biodefense and food safety. To date, the detection and identification of pathogens rely primarily on classic microbiology methods of culturing. In such cases, the technician is required to go through a series of handling steps. There are several rapid methods that are now also used in microbiology that utilize enzyme-linked immunosorbent assays (ELISA) or polymerase chain reaction (PCR) assays. These methods are laborious and time consuming. These methods are also not able to deliver real-time analysis or point-of-care analysis. The use of portable biosensors to rapidly identify pathogens in food and water offers several advantages over the other rapid methods.

Figure 3:
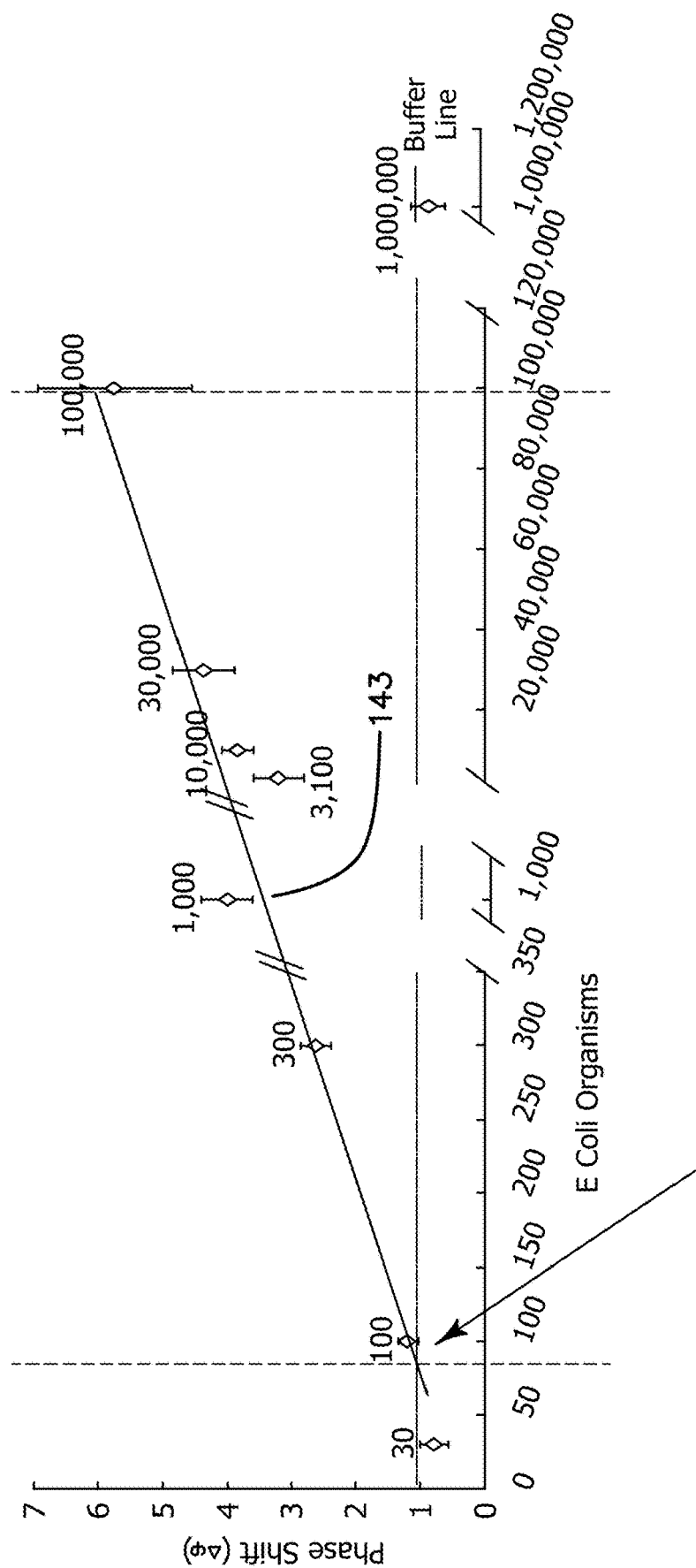
FIG. 3 is a standard curve established using SAW biosensor for measuring *E. coli* O157:H7 cell densities over a concentration spanning three orders of magnitude.

Branch and Brozik demonstrated the detection of the endospores from the gram-negative bacteria specie *Bacillus thuringiensis* B8, a simulant of *Bacillus anthracis*. Use *Bacillus anthracis* is the causative agent for anthrax, a potentially fatal bacterial infection that has as a bioterrorist agent. A $LiTaO_3$ Love-wave biosensor was used to demonstrate a detection level of 1 ng/cm2 when using a polyimide guided layer and BSA as the blocking agent. The detection of such low levels of anthrax simulants revealed the ability detects clinically relevant doses of anthrax. Larson et al. used a similar device to detect both HIV and Ebola viruses at clinically relevant doses. All three devices used antibodies conjugated to a $SiO_2$ layer on a $LiTaO_3$ substrate. In preliminary experiments, the SAW proved capable of detecting concentrations spanning three orders of magnitude, with an estimated limit of detection (LOD) of 74 cells, as seen in FIG. 3. While the cell mass is not a true concentration, the use of an accurate standard curve will allow the rapid correlation to a potential start concentration. SAW biosensors, have been used to detect Ebola virus as a potential point-of care diagnostic tool.

Figure 41:
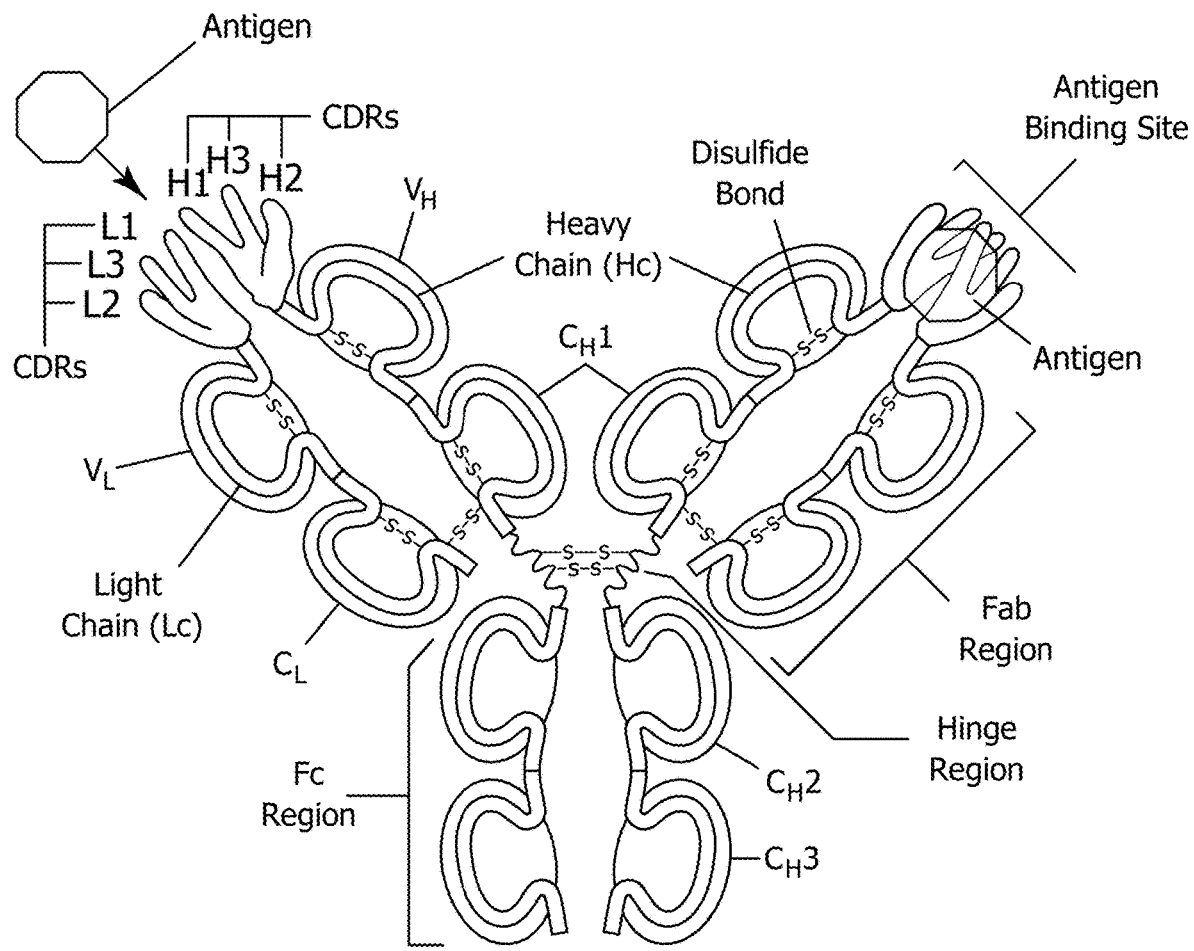
FIG. 41 is a molecular diagram of an IgG antibody comprising heavy chain and light chain with Fragment Fab and fragment Fc along with the antigen binding sites.

A schematic representation of a full-length antibody is shown in FIG. 41. Polyclonal, monoclonal and recombinant antibodies have frequently been selected for a wide variety of applications including biomarker detection. Their production involves the exploitation of the immune system of a host organism to produce antibody against target specie. Typically, a host organism is immunized with cells or inactivated microorganisms. Polyclonal antibodies are typically raised in larger mammals. The antibodies are widely used in immunosensor assays for pathogens. However, the inherent nature of polyclonal antibodies is that they bind different epitopes on a single target. In cases where this is undesirable, monoclonal or recombinant antibodies are used. Monoclonal antibodies are often generated through the use of hybridoma technology and murine hosts. The bone marrow, primary lymph nodes and spleen are selected as a source of antibody-producing B cells, which are harvested and fused to immortal myeloma cells. The resulting hybrid cells (hybridomas) secrete full-length antibodies that are directed towards a single epitope. Recombinant antibodies are generated using a phage display technology and the biopanning of antibody reporters against a target of interest. Three types of libraries may be used as sources of antibody pools: synthetic, naïve and immune.

Limit of Detection (LOD) and Frequency Domain

The Love wave and its subspecies SAW biosensor operating in the shear horizontal mode with its guiding layer are devices which are able to operate at higher frequencies than traditional QCMs. Typical operation frequencies are between 80-300 MHz Higher frequencies as described below, lead in principle, to higher sensitivity because the acoustic wave penetration depth into the adjacent media is reduced. However, the increase in the operation frequency also results in an increased noise level, thus restricting the LOD. The LOD determines the minimum surface mass that can be detected. In this sense, the optimization of the read out electronics or analog front end (AFE) and characterization system, which in the illustrated embodiment, includes an analog sensor coupled to an analog interface (AFE) and analog computation module (ACM) for the Love wave and SAW biosensor, is the means for improving the LOD. The SAW proved capable of detecting concentrations spanning three orders of magnitude, with an estimated limit of detection (LOD) of 74 cells, as seen in FIG. 3, which shows phase shift of the SAW wave as a function of the number of *E. Coli* organisms in graph line 143.

Shear Horizontal SAW

Figure 27:
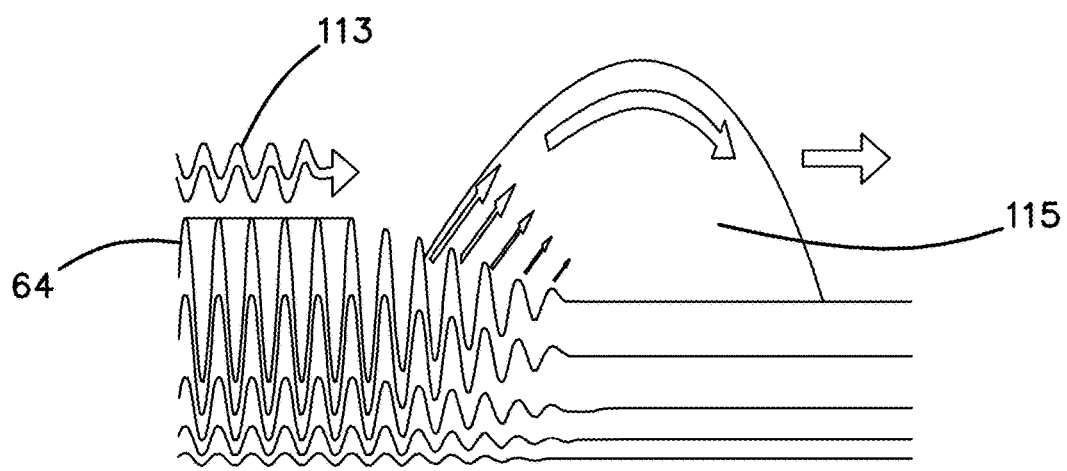
FIG. 27 is a schematic depiction of a shear horizontal wave and a droplet of liquid loading the same.

The design and performance of guided shear horizontal surface acoustic wave (guided SH-SAW) devices employing a crystal $LiTaO_3$ substrate is introduced for high-sensitivity chemical and biochemical sensors in liquids. A schematic depiction of a shear horizontal surface acoustic wave loaded by a liquid droplet is depicted in FIG. 27. The SAW 113 launches a shock wave in the surface of sensitive layer 64 shown in highly exaggerated form in FIG. 27. Liquid or a droplet 115 on sensitive layer 64 interacts with the shock wave to induce streaming within the droplet and liquid or droplet movement across sensitive layer 64. The sensitive layer 64 has been functionalized and selective hybridization may have occurred with targets in the liquid. The result will be that the mass of the hybridized or captured targets will load and/or act flow resistive or viscous agents on the shockwave, which will be received by IDT 68 and transduced into an electrical signal. The received signal generated by IDT 68 will differ from the launched signal by IDT 66 in amplitude, phase and/or frequency. The differences will be indicative of the target that has been captured.

Despite their structural similarity to Rayleigh SAW devices, SH-SAW devices often propagate slightly more deeply within the substrate, hence preventing the implementation of high-sensitivity detectors. The device sensitivity to mass and viscoelastic loading is increased using a thin guiding layer on the device surface. Because of their relatively low shear wave velocity, various polymers including polymethylmethacrylate (PMMA) is proposed as the guiding layer to trap the acoustic energy near the sensing surface. The devices have been tested in biosensing and chemical sensing experiments described below and given as examples of the use of SH SAW biosensor. Suitable design principles for these applications are discussed with regard to wave guidance, electrical passivation of the interdigital transducers from the liquid environments, acoustic loss, and sensor signal distortion. In biosensing experiments, using near-optimal PMMA thickness of ~2 µm, mass sensitivity greater than 1500 Hz/(ng/mm2) is demonstrated, resulting in a minimum detection limit less than 20 pg/mm$^2$.

Impedance and Phase Shift

Figures 28A, 28B:
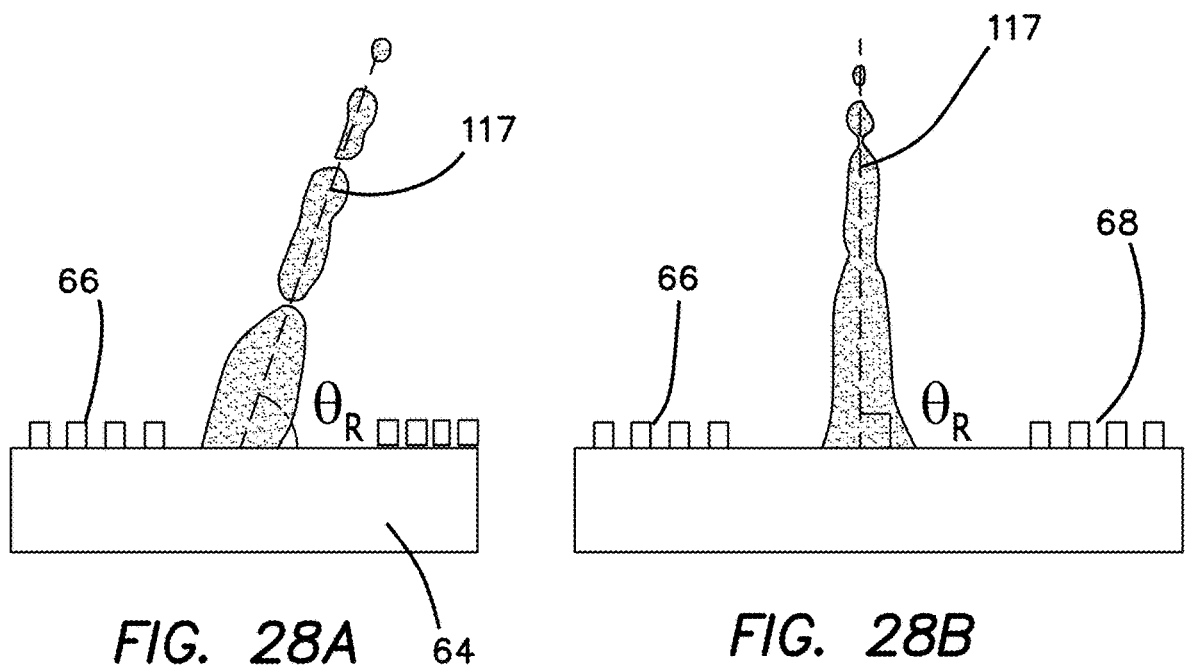
FIGS. 28A and 28B are schematic depictions of the phase shift before mass loading in FIG. 36A and after mass loading in FIG. 36B.
Figure 36A:
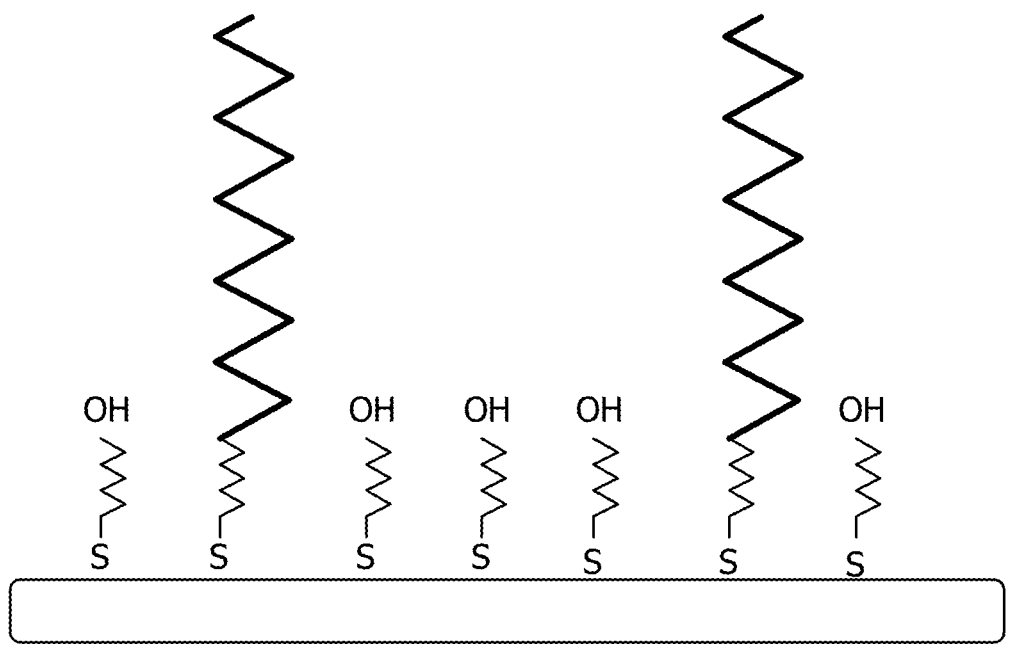
FIGS. 36A and 36B are molecular diagrams showing two different types of ternary self-assembled monolayer (SAM) in a SAM-based DNA hybridization biosensor.

One way to improve the SH SAW phase-shift as a function of the impedance change due to mass loading as diagrammatically depicted in FIGS. 28A and 28B, is to employ the Bode plot of both the logarithm of the absolute impedance (|Z|) and the phase shift ($\varphi$), plotted against the logarithm of the excitation frequency. The phase angle $\theta_R$ changes before loading in FIG. 36A compared to that as graphically shown for after loading in FIG. 36B. The figure further describes a simulation employing COMSOL Multiphysics, which facilitates computational modeling of the SAW biosensor as a resonant cavity, which is perturbed from resonance upon application of functionalizing layers at the sensor surface. These SAW devices in practice actually measure a $\Delta\varphi$-phase change, not $\Delta f$-frequency change, but one can be deduced from the other by the changes in acoustic wave velocity, $\Delta v$, upon layer addition. The perturbation of the media that incurs a certain amount of $\Delta v$ has been determined theoretically for some ideal materials and experimentally verified as described by the example "Low-level detection of a *Bacillus anthracis* simulant using Love-wave biosensors on 36° YX LiTaO$_3$", Biosensors and Bio-electronics 19 (2004) 849-859, where the SH SAW sensor was employed in clinical field setting. The agreement between the theoretical prediction and the actual field testing took into account the application of a linear elastic mass due to the displacement of the liquid media with its analyte by the excitation energy (375 MHz) generated by the RF driver 96 acting on the LiTaO$_3$ piezoelectric layer 60, and where such prediction of the actual measurement used the combined elastic change of the antibody/analyte on the IDT's impact (perturbation) on the mass. The resulting phase shift ($\Delta\varphi$) was predicted, while the actual counts of the analyte in the experiment was further established by using a comparative analysis of the sample(s) by florescent technique of ELISA. The phase shift using bidirectional input IDT's, is detailed in FIG. 36B demonstrating the preferred embodiment of employing a dual resonators where the IDT input is matched with the wave energy in its output's IDT, resulting in a phase change $\Delta\varphi$ value which is in good approximation to the predicted value.

Enabling a reduction of the LOD, which is a measure of the concentration of a solute in a solution, or of any chemical species, in terms of amount of substance in a given volume, while minimizing the concentration limits to $10^{-15}$ molar relative to surface area is a task, which is realized by incorporating bioimpedance amplification. This effort is achieved by this application by the use of fragmented antibodies with multi-epitopes and modification of the antibody fragment where the capture probe (Ab) is modified using encoded DNA library to generate the embodiment (see FIG. 37A). This process enables a compaction of the modified antibody to form a uniform and directional geometry, thereby increasing the density of the antibodies per the available surface area of the sensing and reference lanes. As a corollary of the improved fragmented antibodies, spacer molecules and surface adhesion chemistry, the biosensor amplification is increased proportionally by the order of compaction rate. The benefits of such approach described by Schreiber, G.; et al. in "Computational design of protein-protein interactions". Curr. Opin. Struct. Biol. 2013, 23, 903-910 which describes the biologically relevant conformations among the dynamic ensemble of target protein conformational sampling.

We use the advancements of fragmented DNA encoded libraries to enhance the phenomenon of impedance amplification by improving functionalization of antibody-density and directional stability including the design of multi-epitopes to enable a minimum threshold impedance Z value in which the captured molecules will yield a reliable, statistically significant detection without the need for large ensemble of the targeted biological elements. Hence, a phase shift indicative of a femtomolar resolution can be calculated by the relative density of the fragmented antibodies over the linear surface area, and where the effective geometry of the sensor equivalent capacitive value as a ratio of the linear surface is noted below in section titled "Performance Characteristics of Cells". Using the standard impedance measure along the axis of propagation and its surface area as defined by its geometrical term.

$$Z = \frac{V(t)}{I(t)} = \frac{1}{Y} = \frac{V_0 \sin(2\pi f t)}{I_0 \sin(2\pi f t + \varphi)} \times (\text{geometrical term})$$

One feature of the illustrated embodiment and its computational machinery includes the use of an analog front end (AFE) with an analog computation module (ACM) to enable the measuring, analyzing and reporting of the underlying kinetics of the hybridization and its representation by the phase shift as a linear function of mass loading. The data generated is represented by a continuous analog plotting curve, as a consequence the analog front end (AFE) generating a data string used in plotting a signal for which the time varying feature (such as phase shift and or amplitude) of the signal is a representation of some other time varying quantity, i.e., analogous to another time varying signal. For example, in employing the SAW biosensor the analog audio signal, the instantaneous voltage of the signal varies continuously with the hybridization and the mass loading over the sensing lanes proportionally to the phase shift change over the time domain.

Delay Line and Sensitivity of the Sensor Based on Waveguide and Guiding Layer

In one of the embodiments, the application uses Snell's law to identify the characteristic behavior of the wave propagation and its reflective as well as transmitted impact on the sensitivity measure of such magneto-optical noise disturbance. The design of the waveguide and its coating play a significant role in determining the ability of the sensor (SH SAW) to be able to meet the threshold minimal LOD with a femtomolar concentration value.

The sensor platform comprises waveguide geometry where a shear-wave SAW device is overlaid by a layer of a dielectric material (FIG. 1A, 47A reference designator 64). The main advantage of the waveguide device is that the acoustic energy is confined to the sensing surface, resulting in higher sensitivity to surface perturbations. Waveguides comprise a single layer (described in FIG. 39A) of silica polymethylmethacrylate (PMMA) and photoresist. In general, polymer waveguides are desirable, since they can be easily constructed by using a spin coating method instead of the laborious procedures required for silica deposition. Acoustic waveguide devices employing polymer and silica layers have been used in biosensing applications to detect antibody-antigen and antibody-peptides interactions as well as the formation of supported lipid bilayers In order to use the acoustic waveguide device for biosensing, it is important to optimize the acoustic geometry. One of the parameters that have been extensively studied is the effect of the waveguide thickness on the device sensitivity. These studies involve the utilization of both various SH-wave devices and biological molecules. Since the sensitivity of biosensors depends on both the transducer and biological molecule used, it is important to compare different acoustic wave devices for the detection of the same biological interaction.

Since the sensitivity of biosensors depends on both the transducer physical and electrical elements and the biochemical interaction of the sensing lane with its target analyte, the apparatus' waveguide is then configured in a manner commensurable with magneto-optical principle, thereby, enable the system with guiding layer to achieve a minimal reflection and avoid the critical angles of transmission to avoid total internal reflection, due to geometrical features which form the microfluidic chamber, the IDT dimensionality and the wave length selected for the application. To that extent the application careful analysis of the waveguide transmission is compared isotropic modeling of Snell's law behavior, where different material dielectric-relative permittivity, a measure of resistance encountered when forming an electric field in a medium such as the microfluidic chamber with polydimethylsiloxane (PDMS), and where such measure attenuate and reduce wave reflection.

Waveguide geometry coating on the surface of SH-SAW devices is covered with an overplayed with a dielectric material, which has a lower shear acoustic velocity ($v_o$) than the piezoelectric substrate ($v_s$), and then the SH-SAW is converted to a guided wave known as the Love wave. For a specific frequency, the velocity of the Love wave ($V_L$) depends on the thickness of the over layer and can vary between $v_o$ and $v_s$, i.e. $v_o < v_L < v_s$. The use of silica or photoresist such as Novolac is applied as a waveguide layer on the surface. The effect of the thickness of the layer on the frequency and, thus, propagating velocity of the SH SAW must satisfy the inequality of reducing the wave velocity to satisfy the velocity of the guided wave as close to that of the substrate and the frequency change is small. As the overlayer thickness increases, the velocity decreases until eventually it will reach the velocity of the dielectric of either $SiO_2$ or for example Novolac. Hence, resulting in a larger frequency drop, matching the desired inequality noted above.

Figure 21:
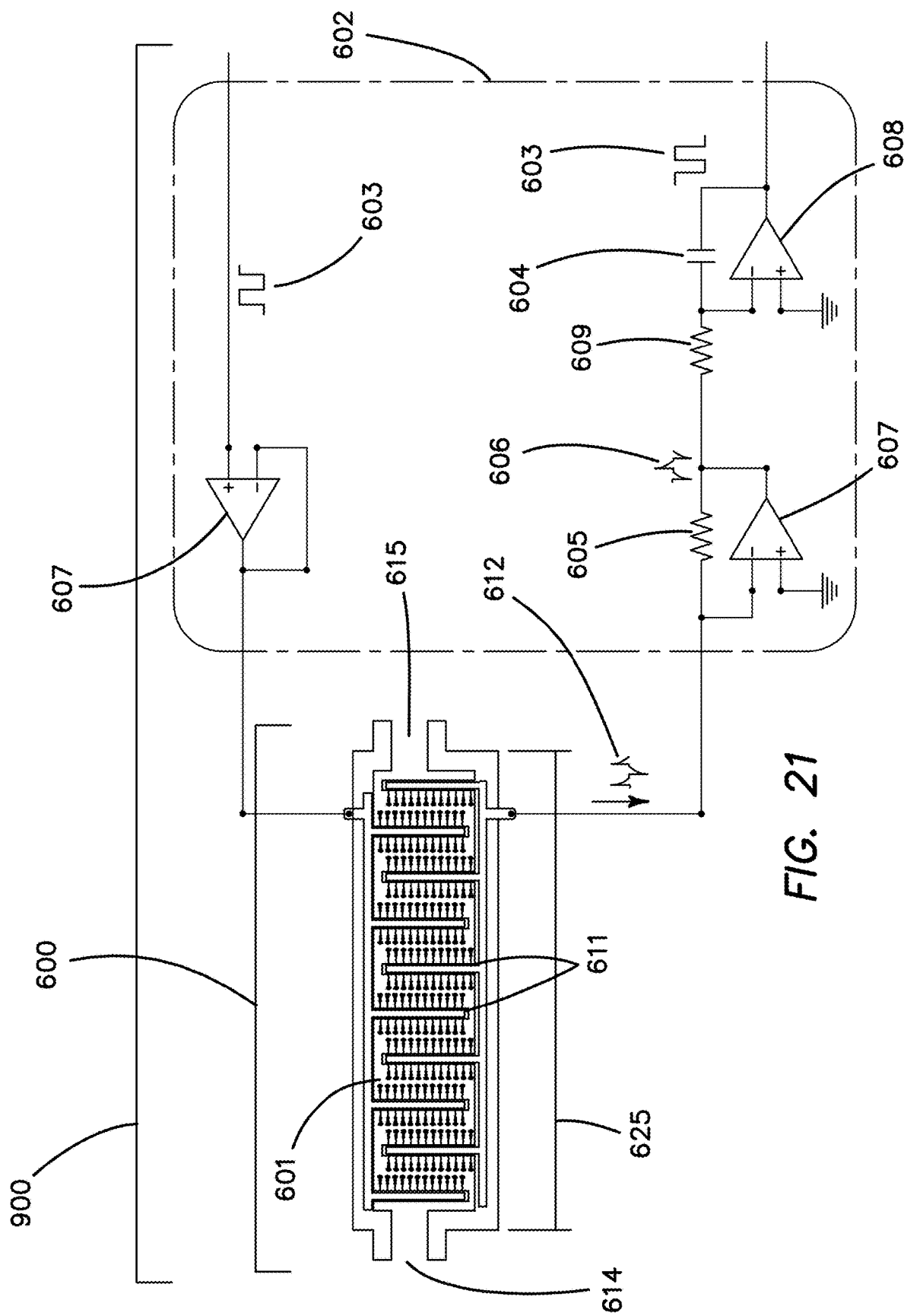
FIG. 21 is a schematic representation of the micro fluidic chamber with detail of the charging and discharging of the capacitive load on the SAW cell's array.

The mass sensitivity ($S_m$) of acoustic wave sensors is defined as the relative change in the frequency due to mass loading divided by the surface density of the deposited mass:

$$S_m = \lim_{m \to \infty} \left[ \frac{\frac{\Delta f}{f_o}}{\frac{\Delta m}{A}} \right]$$

where $\Delta f$ is the frequency change, $f_o$ the operating frequency and $\Delta m/A$ the deposited mass per unit area A—(a detail procedure of how to evaluate and calculate the equivalent capacitive loading and the effective active area of the sensing lane on the SAW biosensor, is described by FIG. 21). The sensing surface A is related to the effective change in phase shift measured and is related to frequency through the following relationship:

$$\frac{\Delta f}{f_o} = \frac{\Delta \phi \lambda_s}{360 L}$$

where f is the wave phase in degrees, $\lambda s$ is the acoustic wavelength in the substrate and L is the length of the propagation path of the wave. Based on expression above and on the assumption that for low concentrations the antibody mass deposition is proportional to bulk antibody concentration, where for example, and where [IgG] is the bulk antibody concentration in solution and C is an arbitrary constant proportional to the bulk concentration of IgG, by simplifying, we obtain:

$$S_m = \frac{\lambda_s A}{360 LC} \lim_{[IgG] \to \infty} \left[ \frac{\Delta \phi}{\Delta [IgG]} \right]$$

By estimating the slope of $\Delta f$ versus [IgG] and by inserting the corresponding data for the concentration constant C, we can evaluate the impact of the guiding layer which form the waveguide.

Snell's law enables the design of a guiding layer, which forms the waveguide. The wave-guide is a feature of the sensor that reduce the refractive response of the surface wave from refracting and thereby reducing the transmission quality of the wave energy. The increased noise emanating from the secondary optical phenomenon of total internal reflection, caused by the incident angle, is estimated and is further optimized. The resulting improvement of coating the waveguide directly effects the LOD analyte concentration and minimizes its value to a femtomolar threshold.

The use of Snell's law in the context of reducing the edge effect of reflecting waves and the reduction of additional noise contributing factor is achieved by deposition of a delay line deposition of $SiO_2$. Refraction takes place at an interface due to the different velocities of the acoustic waves within the two materials comprising the sensor elements. The velocity of sound in each material is determined by the material properties (elastic modulus and density) for that material selected in forming the sensor, e.g. the LTO crystal, the microfluidic chamber, the interdigitated electrodes, the geometry terms (metric of the chamber and the number of the DT's). The intent of this application is to uncover and analyze the boundary conditions of the SH SAW biosensor structure, where the measure of improved performance is aimed at minimization of LOD concentration, to improve the reliability and resolution of the apparatus, meeting clinical relevant standards e.g. such as ELISA or PCR and where the sensor platform is able to resolve concentration of analyte in question at order of femtomolar concentration.

An optimization method comprising of a strategy to reduce LOD concentration, by employing first an amplification of the biological low-signal value with the aid of analog front end (AFE) and second bioamplification of the capture statistics between the analyte and its probe by the use of a DNA encoded library, where sensor functionalization is modified by the use of fragmented, multi-epitopes engineered antibodies. Both embodiments yield an improve LOD minimization, thereby, yielding an improved sensitivity while enabling detection by the SAW biosensor with LOD's concentration threshold of femtomolar value ($10^{-15}$ mol/dm$^3$).

To model the sensor performance we employ Snell's Law for acoustic impedance in order to reduce energy losses, due to the dielectric change between the liquid/solid edge, similar to the reflection and refraction of electromagnetic radiation in an anisotropic media. T. Nomura et al in study titled "Liquid sensor probe using reflecting SH-SAW delay line" describe a shear horizontal mode surface acoustic wave (SH-SAW) which has a unique characteristic of complete reflection at the free edges of the substrate. Snell's observation that sounds travels at different speeds in different materials due to mass of the atomic particles and where force constants are different for different materials dielectric. The mass of the particles is related to the density of the material, and the interatomic force constant is related to the elastic constants of a material. The general relationship between the speed of sound in a solid and its density and elastic constants is given by the following expression:

$$V = \sqrt{\frac{C_{ij}}{\rho}}$$

where V is the speed of sound, C is the elastic constant, and ρ material density. This equation may take a number of different forms depending on the type of wave (Longitudinal or Shear) and the applicable substitution of the elastic constants used. The typical elastic constants of materials include Young's Modulus, E: a proportionality constant between uniaxial stresses. Poisson's ratio ν, the ratio of radial strain to axial strain bulk modulus, K a measure of the incompressibility of a body subjected to hydrostatic pressure. Shear Modulus, G: also called rigidity, a measure of a substance's resistance to shear. Lame's Constants, λ and μ is the material constants derived from Young's Modulus and Poisson's Ratio. When calculating the velocity of a shear wave, the shear modulus is used. It is often most convenient to make the calculations using Lame's Constants, which are derived from Young's Modulus and Poisson's Ratio. Sound travels through materials under the influence of sound pressure. Because molecules or atoms of a solid are bound elastically to one another, the excess pressure results in a wave propagating through the solid. The acoustic impedance (Z) of a material, defined as product of its density (ρ) and acoustic velocity (V).

Hence, Z=ρV where ultrasonic waves are reflected at boundaries where there is a difference in acoustic impedances (Z) of the materials on each side of the boundary. This difference in Z is commonly referred to as the impedance mismatch. The greater the impedance mismatch, the greater the percentage of energy that will be reflected at the interface or boundary between one medium and another.

$$R = \left(\frac{Z_2 - Z_1}{Z_2 + Z_1}\right)^2,$$

the optimization of the geometry and the reduction of the reflection due to dielectric variations of the IDT's and the interfaces on the microfluidic is mitigated by the use of impedance matching and carful geometrical features such as it analyzed by Snell's law.

Since the amount of reflected energy plus the transmitted energy must equal the total amount of incident energy, the transmission coefficient is calculated by simply subtracting the reflection coefficient from one. This simple measure defines the total contribution of all the fabrication steps associated with the delay line material, the IDT's deposition and their geometry, the energy waveguide architecture and the cut angle of the crystal.

The fraction of the incident wave intensity that is reflected can be derived because particle velocity and local particle pressures must be continuous across the boundary. When the acoustic impedances of the materials on both sides of the boundary are known, the fraction of the incident wave intensity that is reflected can be calculated with the equation expressed above, where Refraction takes place at an interface due to the different velocities of the acoustic waves within the two materials. The velocity of sound in each material is determined by the (elastic modulus and density) for that material. The use of Snell's law of reflection provides for a good estimate based on the material properties employed when selecting the delay line.

The selection of the delay line material such as $SiO_2$, simply acts as a wave absorber at the reflecting edge thereby reducing the noise characteristics associated with the edge reflection, which alter the SHS SAW propagation, and inducing an additional nonlinear term to the sensor. A simple experimental measure to evaluate the effect of the delay line contribution to the signal quality is to calculate the value produced based on the material properties selected to absorb the edge reelection and is known as the reflection coefficient. Multiplying the reflection coefficient by 100 yields the amount of energy reflected as a percentage of the original transmitted energy.

IDT's Tailoring Geometry

The SH-SAW is excited on a 36° YX $LiTaO_3$ and the right angle edge of the substrate is used to reflect the SAW. The SAW has two components of particle displacement. One is parallel to the surface along the direction of the wave propagation, and the other is normal to the surface. The desire to sense the liquid phase using a SAW device is complicated by the excessive energy losses experienced at a solid and liquid interface. Displacements normal to the surface generate compression waves, which dissipate the wave energy in the liquid. Therefore, liquid phase sensing using the SAW device is difficult. It is possible to use shear horizontal mode SAW (SH-SAW) that are not affected by the described energy loss mechanism.

The magnitude of the output signal is the function of the ratio of the signal's wavelength 127 and the distance 2d. The sinusoidal electrical input signal generates an alternating polarity between the fingers of the interdigitated transducer. Between two adjacent sets of fingers, polarity of IDE fingers is switched based on polarization e.g. (− + − +). As a result, the direction of the electric field between two fingers will alternate between adjacent sets of fingers. This creates alternating regions of tensile and compressive strain between fingers of the electrode by the piezoelectric effect, producing a mechanical wave at the surface. As fingers on the input IDE's of the sensor, where it experience the same level of compression or tension, the space between them—known as the pitch—is the wavelength λ of the mechanical wave. The synchronous frequency $f_0$ of the device with phase velocity $v_p$ and pitch p is defined by the expression:

$$f_0 = \frac{v_p}{p}$$

Defining the pitch and the electrodes length deposited over the crystal $LiTaO_3$ is a critical parameter in establishing the resolution of the sensor resolution. Hence, the limit of detection is directly related to the frequency domain that operates the device and it is linearly related to the frequency, the higher the frequency the higher is the resolution.

Figure 29:
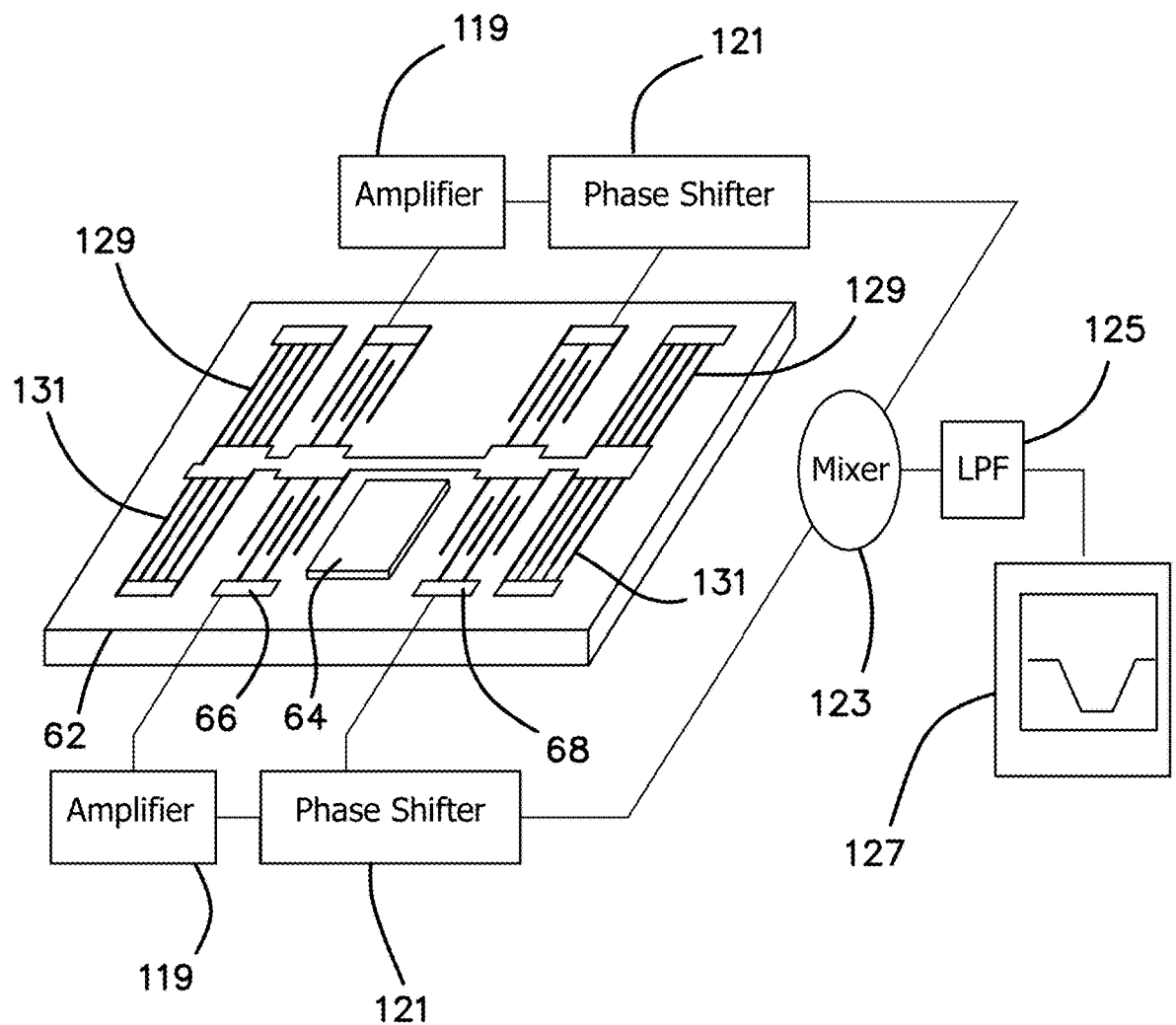
FIG. 29 is a diagram of a SAW delay line.

If the distance 2d is equal to the wavelength, the magnitude of the output voltage is maximal. The corresponding frequency is called the "center" or the synchronous frequency of the apparatus. The magnitude of the output voltage decays as the frequency shifts from the center frequency. It means basically, a SAW device is a transversal bandpass filter, which in the proposed configuration is capable of being altered by the added mass, whereby the device is attenuated with added mass. In transversal filters, the phase characteristic is a function of the distances between the electrodes and the amplitude characteristic is a function of the number of electrodes and their lengths. The IDT geometry 131 is capable of almost endless variation, leading to a wide variety of devices. If the electrodes are uniformly spaced, the phase characteristic is a linear function of frequency, e.g., the phase delay is constant in the appropriate frequency range. This type of the SAW device is then called delay line as diagrammatically depicted in FIG. 29 showing a reference lane (functionalized with non-specific antibody) 129 and sample line (functionalized with specific antibody) 131. Input IDT 66 is coupled to an amplifier 119 which is also coupled to a phase shifter 121 coupled to output IDT 68. The phase shifter outputs from reference line 129 and sample line 131 are coupled to a mixer 123, whose output is coupled through low pass filter 125 to frequency counter 127.

Mass Loading

Sensor phase changes due to mass loading by the hybridization of the analyte conjugation depend on the substrate's length and its elasticity constants. These changes cause velocity and phase delay variations, which then proportionally change the center and resonant frequency, attenuation and time delay of the device.

Time delay τ of the SAW delay line sensor, is the ratio of acoustical length L and SAW velocity v. The design of the sensor boundary conditions we set the following: L and v are changed due to mass loading from the hybridization over the surface layer. Therefore, the relative change of the delay due to the variation of the measurand γ is expressed as follows:

$$\frac{d\tau}{\tau} = \left(\frac{1}{L}\frac{\partial L}{\partial y} - \frac{1}{v}\frac{\partial v}{\partial y}\right)dy = \gamma_y dy$$

Where $\gamma_y$ is termed the delay sensitivity y. It is determined by the orientation and type of crystalline material (36° Y-cut X-propagating $LiTaO_3$) used in fabrication of the proposed biosensor. As shown in our SAW design, the delay line is placed in the feedback loop of the oscillator, so that the oscillation frequency is proportional to the measurand. The accumulation of mass on the surface of an acoustic wave sensor will affect the surface acoustic wave as it travels across the delay line. The velocity v of a wave traveling through the sensing and reference lane(s) is proportional to the square root of product of the Young's modulus E and the density ρ of the material, and as noted by the expression: $v \propto \sqrt{E/\rho}$, describing the proportionality relationship between mass and phase shift, similar to mechanical spring k characteristic.

Mass Loading and linear Phase Shift

Figure 30:
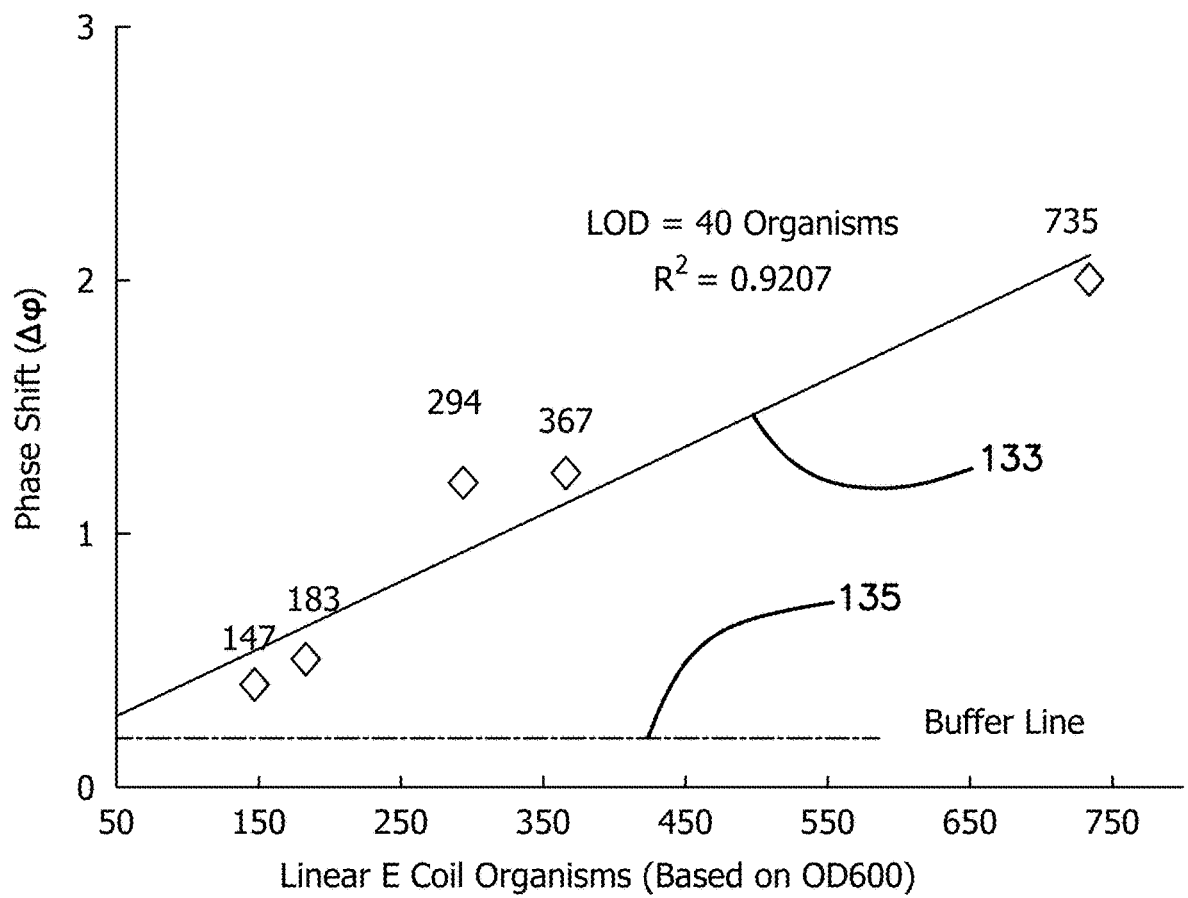
FIG. 30 is a graph of the phase shift as function of the mass loading by *E. Coli* organisms.

The apparatus presented herein was subjected to a set of experimental test, which resulted with the data presented. A graph of the phase shift as function of the mass loading by E. coli organisms is depicted in FIG. 30. The phase shift in the SAW signal above that introduced by the reference lane fitted with nonspecific antibody (no hybridization of the pathogen in the analyte e.g. E Coli will be conjugated as the reference Lane was fitted with buffer solution and IgA). As shown in dotted line 135 where the measured phase shift is constant—the use of nonspecific antibody is set as a control line for the apparatus, to perform a differential detection between the specific sensing lane where the lane was functionalized with the specific E. coli serotype O157, where region recognized by this antibody is LPS oligosaccharide and where the antibody was non-reactive with serotypes: O111, O125, O20 and O55 and K12.

The measured hybridization over different concentration was repeatedly detected and its data was linearized with least square fitting algorithm. The data shown is the results of differential phase shift between the reference lane and the sensing lane. The oscillations are sustained if the following conditions are met: the amplification in the open loop is greater than 1 and where the net phase in the closed loop, (acoustical plus electrical), equals 2πn, where n is the number of the mode, e.g.:

$$\frac{2\pi fL}{v} + \varphi_A(f) = 2\pi n$$

Where f is the oscillation frequency and $\phi_A$ is the phase of the amplifier. Since the electrical delay is much smaller than acoustical, from the two expressions we obtain:

$$\frac{df}{f} = \frac{-d\tau}{\tau} = -\gamma_y dy$$

The mass loading changes on the sensing surface provide the straight influence of the measurand on the frequency while the apparatus electronics (AFE) amplify the sensor output signal which is then computed and scaled by the arithmetical module (AU) as a continuous graph, the AU further subtracting the phase-shift output generated by the reference lane and the sensing lane.

If more than one SAW sensor is present in the configuration, (such as in an array form of sensors) and where parallel measurements conducted with a substrate functionalized with the same antibody, then the relative change in the delay found, is calculated as a linear addition:

$$\frac{d\tau}{\tau} = \sum_{i=1}^{n} \gamma_{yi} d\gamma_i$$

where n is the number of measurand on the sensing lanes, to avoid errors caused by cross sensitivities of the array of sensors on a common microfluidic chamber, a differential measurements of delay is conducted by the apparatus and where the energy excitation is triggered by a time delay (e.g. five millisecond apart between measurements)

Figures 31A, 31B, 31C:
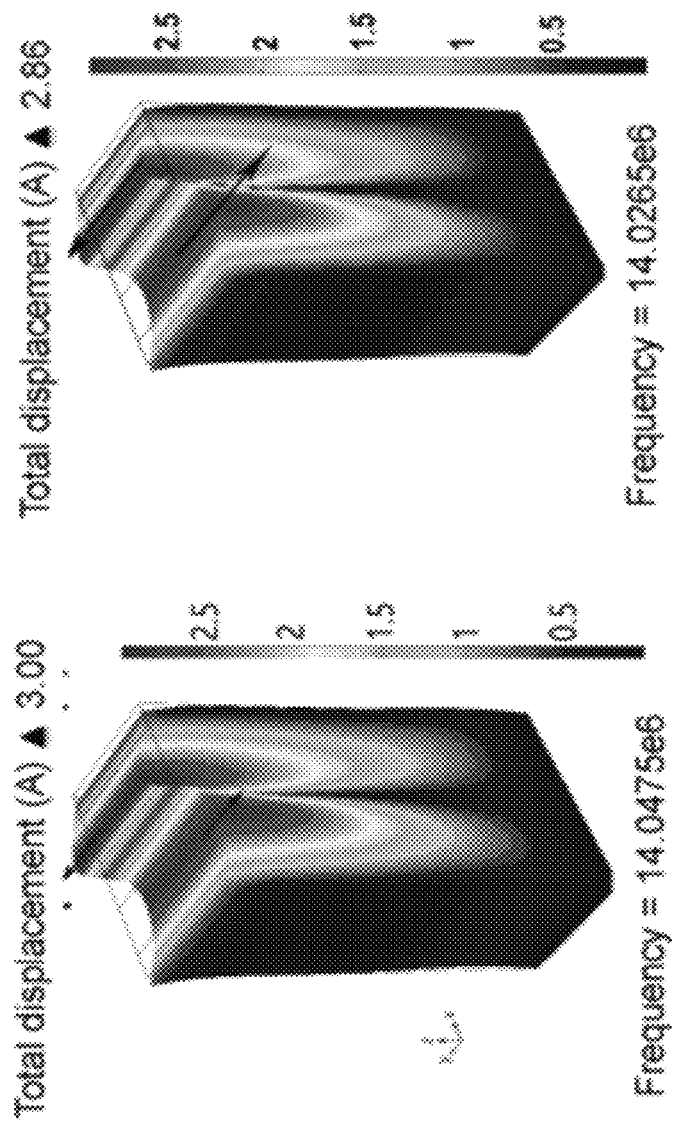
FIGS. 31A-31C shows the displacements in FIGS. 31B and 31C at two different frequencies in the lithium tantalite crystal SAW device of FIG. 31A.

FIG. 31A is an orthographic representation of a surface acoustic wave crystal formed in a mode of SH SAW by using a Y cut with X-axis propagation, where its energy, with surface velocity of 4160 m/s directed and confined to the crystal's edge, such as LiTaO$_3$. The crystal energy is reduced to a shear horizontal (SH) wave at a rotation angle of about 36°. The three dimensional displacements of a SAW in the crystal underneath the IDTs 66, 68 shown in FIG. 1*a* are depicted and are represented in graphs at two different frequencies in FIGS. 31B and 31C, which further depict the relationship of the wave propagation to the sensitivity parameter associated with the input frequency and its impact on pressure, strain, torque, temperature, and mass. The figures graphically depict a surface of LTO fabricated with two IDTs separated by some distance on the piezoelectric substrate. These phenomena can cause a change in length along the surface of the device. A change in length will affect both the spacing between the interdigitated electrodes, (altering the pitch), and the spacing between IDTs, (altering the delay). This phenomenon is sensed as a phase-shift, amplitude change, or time-delay in the output electrical signal. As reported by Shiokawa, S. "Design of SAW sensor in liquid": (Jp. J. Appl. Phys. 1988, 27, 142-144), that when conducting measurements in water, an additional problem arises due to the dielectric constant of water ($\varepsilon_r \approx 80$) which is significantly higher than that of quartz ($\varepsilon_r = 4.7$). This leads to a dramatic decrease in the acoustoelectric coupling and to a significant electrical impedance mismatch, which causes short-circuit of the IDTs through the water. The later can be minimized by using substrate materials for the device with a $\varepsilon_r(\omega)$ closer to that of water; for example, LiTaO$_3$ with relative primitively value of $\varepsilon_r = 47$.

Figure 32A:
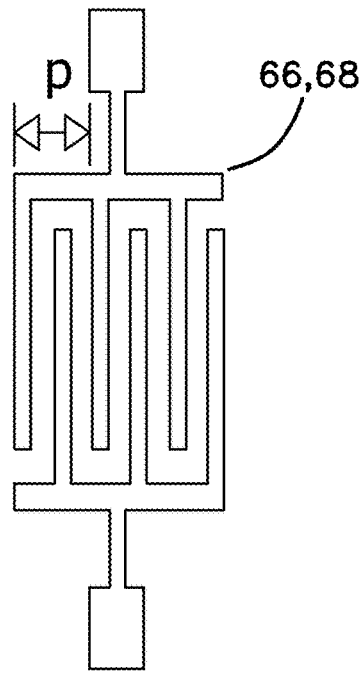
FIG. 32A is a plan diagram of an IDT in a SAW device.
Figure 32B:
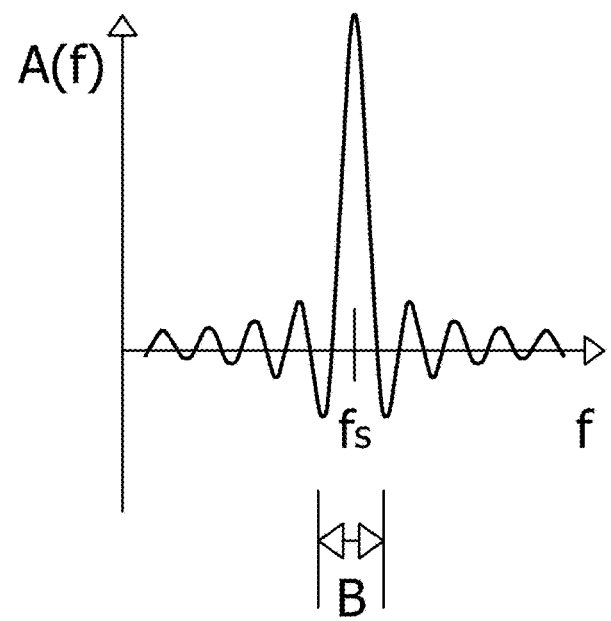
FIG. 32B is a graph of the amplitude of the SAW wave as a function of frequency created by such an IDT.
Figure 32C:
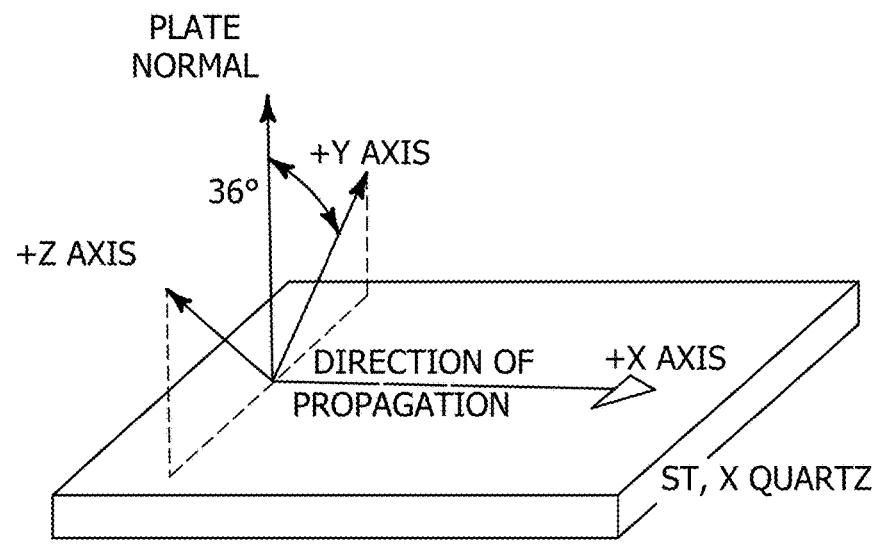
FIG. 32C is an orthographic representation of the Euler angles, a means of representing the spatial orientation of the crystal LiTaO$_3$ cut and its wave-propagation reference frame (coordinate system or basis) as a composition of three elemental rotations starting from a known standard orientation of 36° relative to its x axis frame.

The 36° Y-cut X-axis propagation of LiTaO$_3$ crystal (depicted in FIG. 32C) has been used extensively due to their low insertion loss, very large electromechanical coupling factor K$^2$, and low propagation loss. Using these SH wave devices, Love modes will propagate within a thin guiding layer if the shear velocity in the deposited layer is less than the shear velocity in the substrate. The guiding layer selection defines the characteristic behavior of the propagation and its operation as a biosensing platform is due to its confinement of the energy dispersion where it is minimizes the insertion loss. The fabrication of the crystal is accomplished by the use of ST-cut quartz defined by FIG. 32C where the cut is 90°-off the x-axis direction and its orientation is set at 36° relative to Y-axis of crystal seed of LiTaO$_3$.

The frequency responses for both sensing and reference lane are illustrated when it was used experimentally by the authors—see FIG. 3, the data generated when using the LTO crystal with its SH SAW mode at a frequency domain of 375 MHz established the performance of the sensor).

It is further noted by the experimental data cited by the literature that for ST-cut quartz the response is noisy, with only a few crossings with 0°. The 0° crossings are usually the operation points of the sensors, given the fact that enough amplifier gain is supplied to the system. For the 36° Y-cut lithium tantalate quartz, the response is less noisy with several 0° crossings, which results in excitation of several modes as provided by the optimization schema of the illustrated embodiments. This application employs the 36° Y-cut lithium tantalate quartz, with a frequency domain of 375 MHz.

Sensor Design

SAW sensor, schematically shown in FIG. 1A; include a transducing area and a sensing area. The transducing area includes the interdigital transducers (IDTs) 66, 68, which are metal electrodes, sandwiched between the piezoelectric substrate and the guiding layer. A typical IDT pattern is diagrammatically depicted in FIG. 32A. The input IDT 66 is excited electrically (applying an RF signal) and launches a mechanical acoustic wave into the piezoelectric material as graphically depicted in FIG. 32B. The design and analysis of SAW devices, a SAW delay line model has been created using Simulink®, which provides a graphical interface for the development of dynamic multi-domain (electrical, mechanical and piezoelectric) simulations.

Figure 40C:
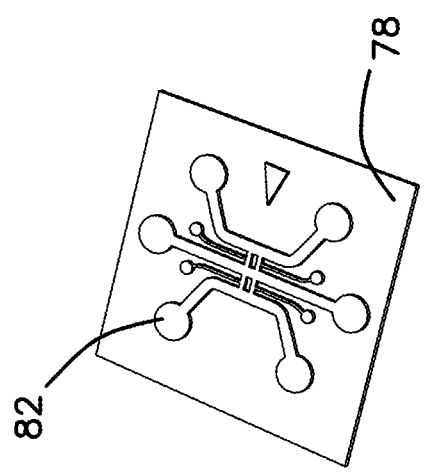
FIGS. 40A-40F diagrammatically illustrate the PDMS molding process.
Figure 40F:
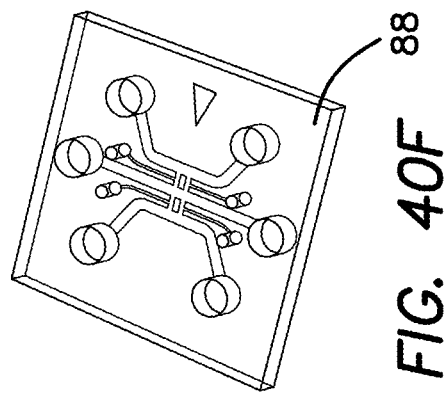
Figure 40B:
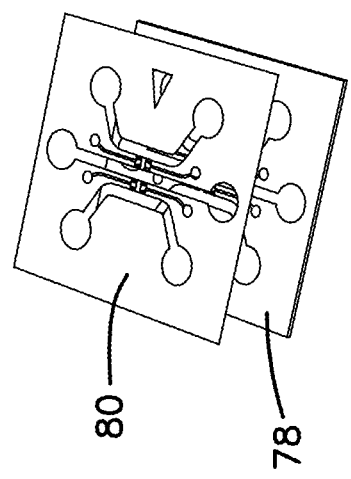
Figure 40E:
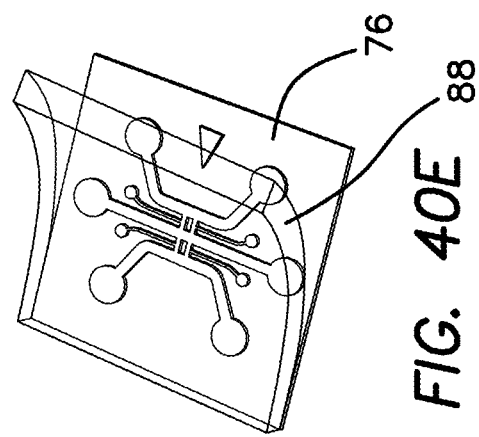
Figure 40A:
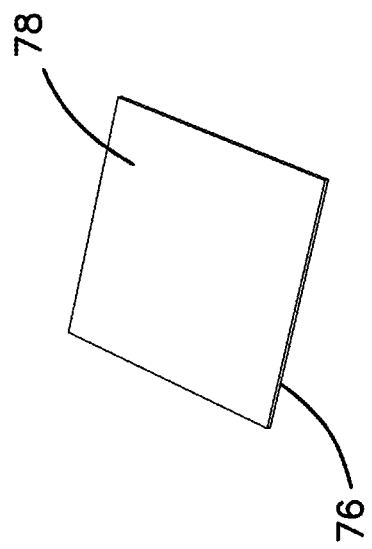
Figure 40D:
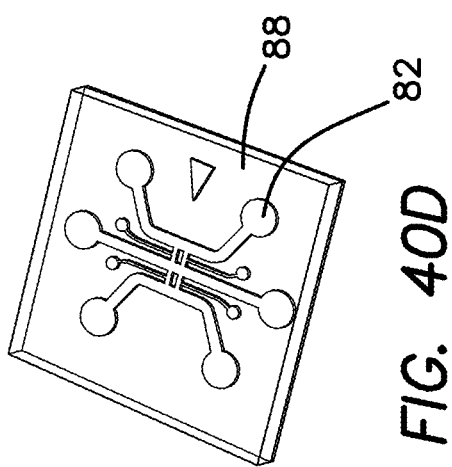

The model calculates the radiation conductance G, the acoustic susceptance Y, (the inverse of impedance Z) and the frequency response for the system. The model includes optimization for the aperture height. The effects of triple transit echoes have been added to the model from the Impulse Response model, where one can calculate the wavelength (A) and the number of finger pairs (Np) using the following equations:

$$\lambda = \frac{V}{fo}$$

where V is the acoustic velocity in the media, fo is the center or synchronous frequency. The frequency noted in FIG. 40*b* is an indication of where "sweet spot" tuning occur and the center frequency optimal design must match the IDT resistance (real impedance) to the source resistance.

Figure 33:
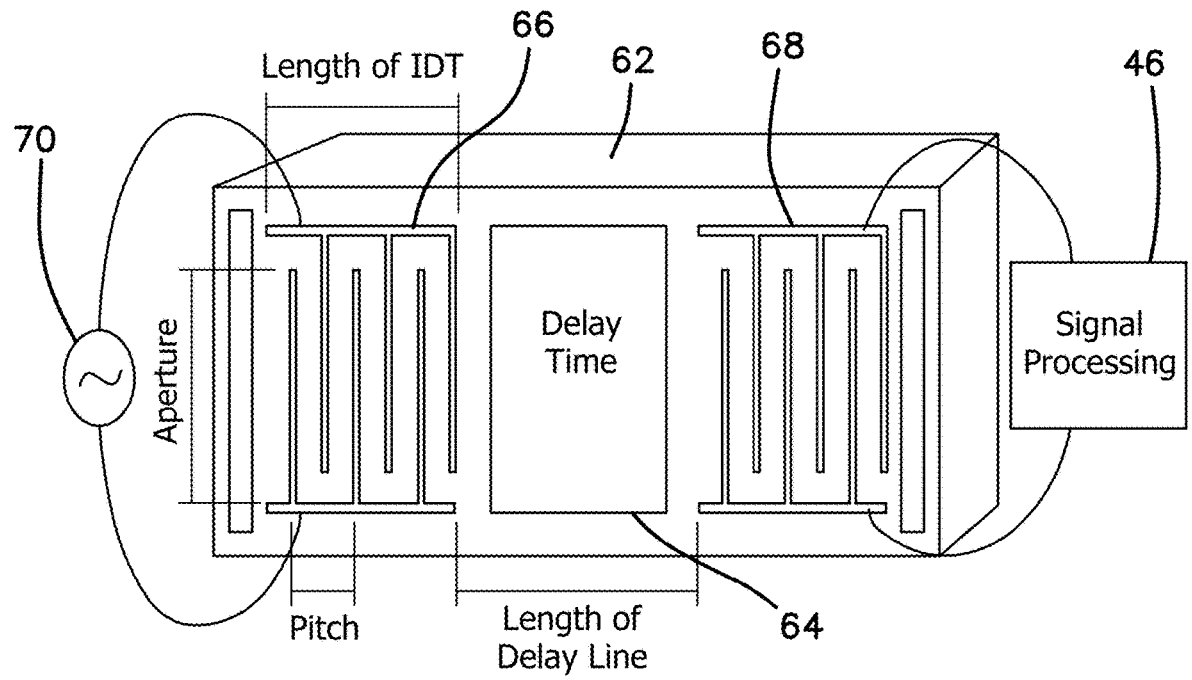
FIG. 33 is a diagram of a SAW device having its input coupled to an RF source and its output to a signal processor.

The device aperture is adjusted so that the IDT design achieves the correct resistance. Where the wave energy is guided through the guiding layer (waveguide) up to the output IDT 68, where it is transformed back into a measurable electrical signal. The sensing area 64 is the area of the sensor surface, located between the input IDT 66 and output IDT 68, which is exposed to the analyte. A simplified diagram of a SAW device is depicted in FIG. 33, which is substantially the same as that shown in FIG. 1A.

The sensor uses shear horizontal (SH) surface acoustic waves, which are frequently used for liquid-loaded biosensing applications. In SH-SAWs, the particle displacement is in the plane of the surface. SH-SAWs are not affected or damped by liquid loading, as compared to Rayleigh waves. On the other hand, almost all SH wave propagation on various substrates results in leaky waves (not pure waves like Rayleigh waves), which also leak into longitudinal and shear vertical wave components when excited. For this reason, special cuts of typical wafer types of wafers are typically used for SH waves, in which the energy is highly concentrated on the SH mode. Typical wafer types used in this application employ a SH-SAW with ST cut quartz, at 36° Y-cut lithium tantalate (LiTaO$_3$).

The sensing mechanism of SH-SAW sensors relies on the change of SAW speed either by change in mass loading (most biological and chemical sensors) or by changing physical parameters, such as the sensor native frequency, mode of detection e.g. phase shift or amplitude change, geometry layout of the IDT's, or the delay dielectric material forming the waveguide).

In general, the majority of SAW sensors include surface treatments and extra layers to effectively and specifically sense the target analyte. Several SH-SAW sensors have been reported using 36° Y-cut LiTaO$_3$. In the illustrated embodiment, the SH-SAW generating wafers is an ST-cut quartz, 36° Y-Cut, LiTaO$_3$ with delay path designs and surface functionalization steps which were validated experimentally as shown below. It was observed that ST cut quartz is the most stable and the easiest to operate among those tested. ST-cut quartz is also favorable for narrower bandwidth operation, and it does not need additional layers or gratings to concentrate the energy in the surface. SH waves are present in the direction of 90° off the x-axis in ST-cut quartz, so the features were designed to obtain wave the propagation direction is z, the normal direction y, and the plane of the substrate is in the x-axis, as it is graphically illustrated by FIG. 32C.

The substrates used in the illustrated embodiments are a 3-inch, single-side-polished, 500 μm-thick ST-cut quartz wafers. The SH-SAWs were generated and sensed by a pair of interdigital transducers separated with a delay path on these wafers. The pitch (corresponding to the wavelength of the SAW) is chosen as 300 μm, ensuring fabrication yield and tolerable wave attenuation through the delay path. Each finger of the IDT was set at a 75 μm wide corresponding to the one quarter of wavelength for the most efficient SAW generation. The design parameters of the sensor are illustrated by the embodiments and their accompanying figures. The most important parameter for SAW device design is the center frequency, which is determined by the period of the IDT fingers and the acoustic velocity. The governing equation that determines the operation frequency is: $f_0 = v_{saw}/\lambda$ Where λ is the wavelength, determined by the periodicity of the IDT and $v_{saw}$ s the acoustic wave velocity λ=p=finger width×4 with the finger width as shown in FIG. 2B is determined by the design rule of the technology which sets the minimum metal to metal distance. $v_{saw}$, which is the surface acoustic wave velocity. The example shown by the table is a sample's use of the method for finding the "sweet frequency value" for its intended application.

| Wavelength (λ) | 300 μm |
| Finger Width (λ/4) | 75 μm |
| Finger length | 6250 μm |
| Number of IDT finger pairs (P) | P = 20 |
| Total sensor size | 22 mm × 22 mm |
| Delay path length | 12 mm (40λ) |
| Resonance frequency | 16.8 MHz |

Waveguide Layer

In order to achieve high sensitivity in SAW sensors, it is essential to confine a maximum amount of acoustic energy near the surface of the substrate and minimize wave scattering into the bulk of the substrate. To achieve this in Love-mode SAW devices, a waveguide layer FIG. 1B made of a dielectric material is used to confine acoustic energy close to the surface of the devices. For high waveguide efficiency, the coated material should have a wave velocity less than that of the base piezoelectric substrate material. Dielectric materials such as silicon dioxide, parylene, polymethylmethacrylate, and others are good waveguide materials.

Figure 34:
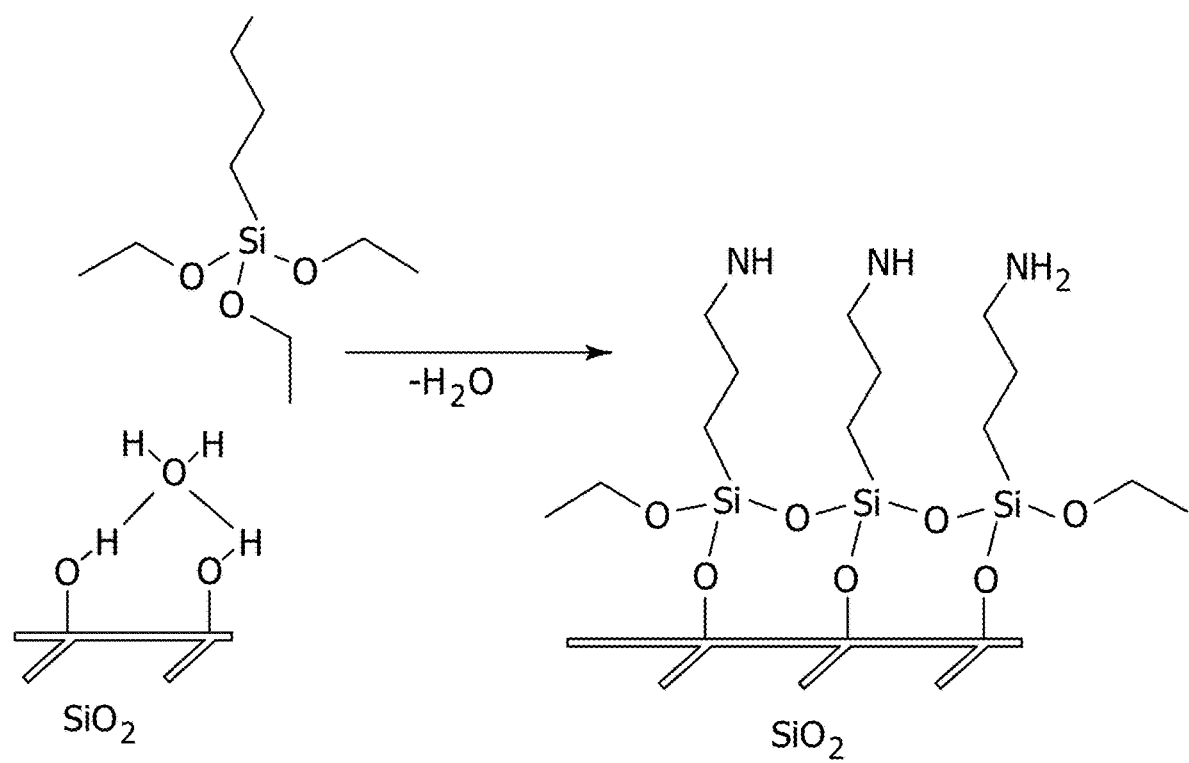
FIG. 34 is a molecular diagram showing the functionalization of a silicon dioxide layer with an insular silicon layer.
Figure 35A:
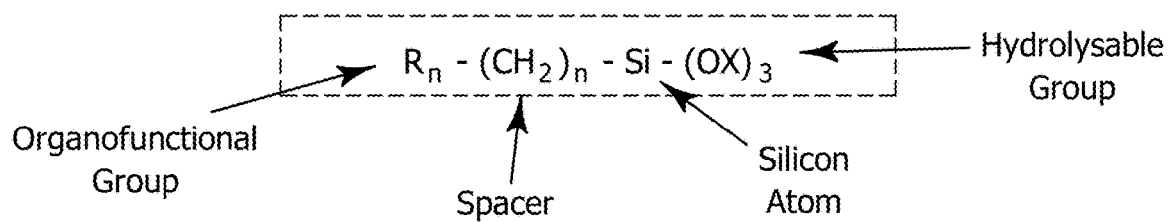
FIGS. 35A-35D are diagrammatic examples of the functionalization of silicon using organo-functional groups and hydrolysable groups.
Figure 35B:
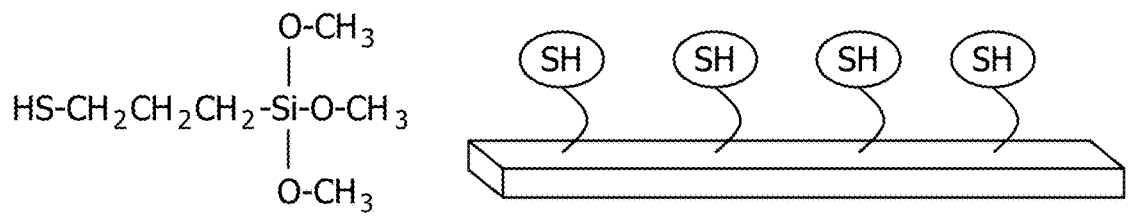
Figure 35C:
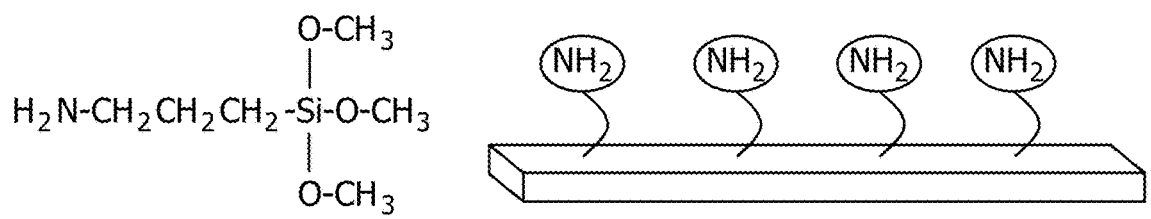
Figure 35D:
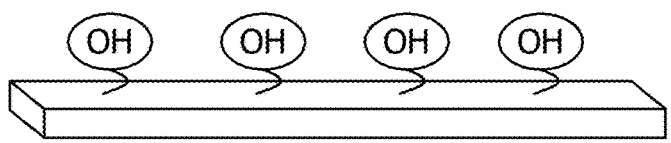

Silicon on Insulator (SOI) technology is a layered silicon insulator silicon substrate combined with LiTaO$_3$ in place of conventional silicon substrates in semiconductor manufacturing, especially microelectronics, to reduce parasitic device capacitance, thereby improving performance of the biosensor substrate, where the LiTaO$_3$ is layered with the metalized IDT formed in a geometry on the wafer and is then deposited with a SiO$_2$ film to form the waveguide layer. A silicon dioxide layer with an insular silicon layer being functionalized thereon is shown in the molecular diagram of FIG. 34.

Waveguide

One of the elements forming the boundary conditions defining the sensor performance for low-level detection (LOD) of bioagents in an aqueous environment is the mass sensitivity optimization of the Love-Wave acoustic sensor. The illustrated embodiment is an experimental study of 36° YX cut on LiTaO$_3$ based crystal for detection of pathogenic spores in aqueous conditions. The detection limit (DL) of Love-Wave based sensor is a function strongly dependent on the overlying waveguide.

Sensors that operate on shear horizontal surface acoustic waves (SH-SAWs) are now widely used for the characterization of liquids, including biological fluids. SH-SAWs do not involve a normal component of mechanical displacement and exhibit weak damping when the wave-bearing surface contacts with a viscous liquid medium, which makes it possible to use these waves in sensors to characterize liquids. There is extensive literature devoted to the development and application of SH SAW sensors, including those of the electronic tongue type for detecting and identifying liquid phase substances. In the case of SH SAW sensors, differences between the response signals to various analytes are achieved by using different thin film coatings in the SAW delay lines or using SAW delay lines at several different frequencies. SAW delay lines, which form the waveguide, impact the shear-horizontal waves propagating on the top layer of a coated layer, direct and reduces the acoustic noise. Attention to this element within the boundary conditions of the device must be focused on the selection of a material, which would effectively guide the Love wave. Silica and polymethyl methacrylate were used as guiding layers and the mass sensitivity of the corresponding sensors was tested in air. Low-shear-acoustic-velocity polymer over layers was found to guide the SH SAW most effectively with a maximum sensitivity. The polymer waveguide sensor was further used to detect protein adsorption on the polymer surface from IgG solutions within the concentration range suitable for clinical range. Finally, the effect of the acoustoelectric interaction on liquid-based applications was studied by utilizing a three-layer waveguide geometry. It was found that the evaporation of a 50 nm gold layer on the polymer over layer can be used to eliminate acoustoelectric interactions without interfering with the Love wave propagation. After activation with protein A and IgG, the above system was used successfully to detect the direct binding of 400 ppb of an herbicide such as atrazine.

This application employs the SH SAW sensor, where the crystal is based on a 36° rotated Y cut X axis propagating wave (LiTaO$_3$) (36° YX LTO) on piezoelectric substrates, in which SAWs are generated and detected using conventional fabrication of lithographic technique in order to form the interdigital transducers (IDTs) metal deposition. As is known, IDTs excite both the surface skimming bulk acoustic waves with SH-polarization and the leaky SH SAW. The phase velocities of the waves of two types on the free substrate surface are almost equal (a difference being on the order of $10^{-5}$) and the SAWs are effectively converted into volume waves. In order to inhibit this conversion, a conducting film that "presses" the SAW to the substrate surface usually coats the region between IDTs. In some cases, the wave energy concentration at the surface (and, hence, the sensitivity) is increased by applying a several micron-thick dielectric film (e.g., $SiO_2$) possessing waveguide properties with respect to SH SAW. Thus, the sensor structures on 36° YX LTO substrates may contain surface regions with different electrical and acoustical properties (i.e., they can be inhomogeneous).

The SH polarized acoustic waves are very effectively reflected by the substrate edges and various in-homogeneities present on the surface, (an noise generating sources that this application take into considerations by applying magneto-optical analysis-(Snell's Law), to reduce the art effects of wave reflective and refractive response, as the wave travel through the guiding layer. Sensors that operate in a continuous mode, used in most experiments, generate reflections, which lead to distortions in the amplitude and phase characteristics of the sensors. In order to ensure a correct measurement of the system response (which usually represents a change in the signal amplitude and/or phase), it is necessary to take special measures either to decrease these distortions or eliminate them, e.g., by using SAW excitation in a pulsed mode or by tailoring the microfluidic chamber geometry with its guiding layer through the analytical use of magneto-optical optimization and the use of the material properties to reduce such art effects.

Functionalized Layer

The functionalization of the sensing lane and its counterpart reference lane on the SAW biosensor cannot be overestimated, as it is one of the critical parameters within the family of causes, which affect the SH SAW sensitivity and its ability to minimize the LOD. This application teaches a set of steps with its chemical recipe to improve the fictionalization of the linker-molecule and provide for a stable probe for the subsequent conjugation of the probe with its analyte. Consider the chemical functionalization of surfaces for building three-dimensional engineered biosensors and in particular the Linker molecule chemistry. Modular, self-assembling peptide linkers are used for stable and re-generable biosensor interfaces. The formation of organosilane-based thin films provides a simple means to incorporate chemically well-defined functional groups on glass-type surfaces. Variations in either the terminal groups or structure of organosilanes have greatly extended the utility of SAW devices by presenting specific chemical groups and altering the physical property of SAW the devices and extending these devices to many new applications. A diagrammatic example of such functionalization is shown in FIGS. 35A-35D.

Biomolecules Immobilization

Figure 42:
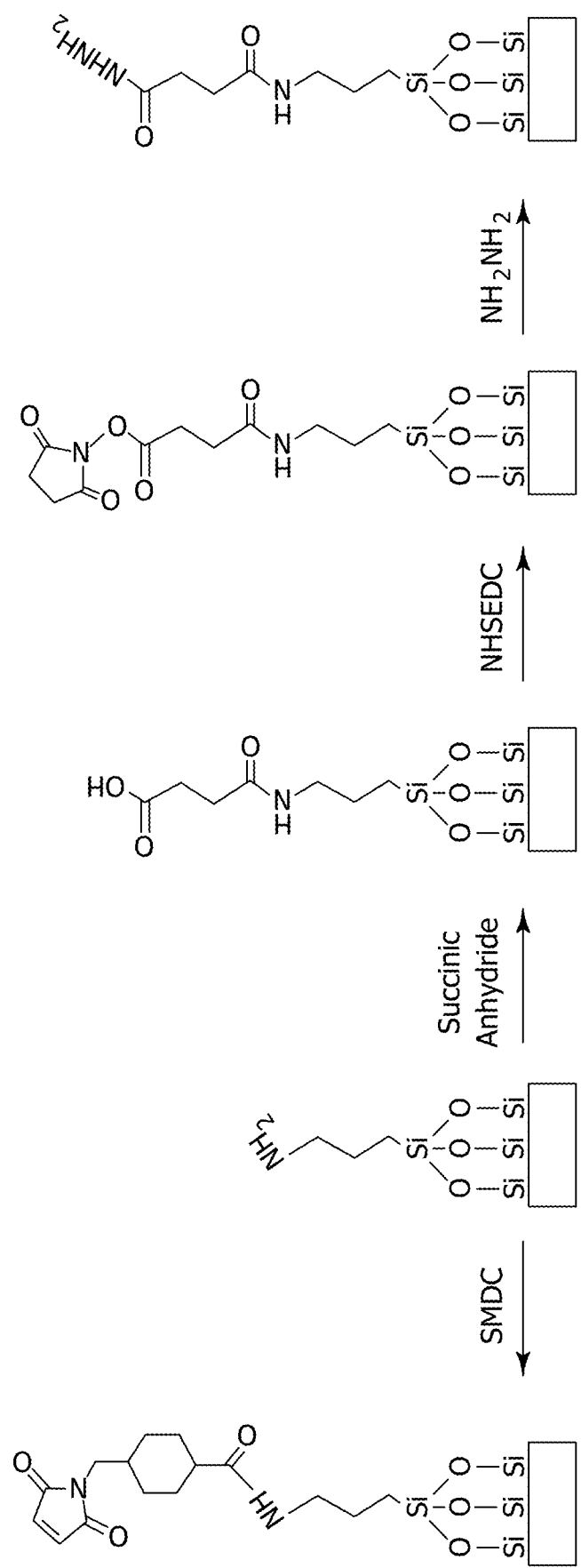
FIG. 42 are molecular diagrams of amino groups in APTES film on silica dioxide ($SiO_2$) chemically modified to carboxyl forms, NHS ester, hydrazide or maleimide groups.
Figure 43A:
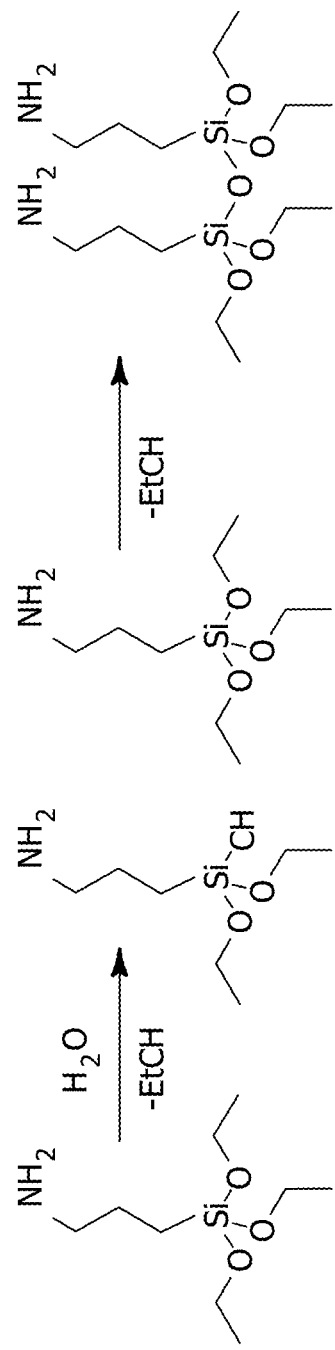
FIGS. 43A and 43B are molecular diagrams illustrating APTES hydrolysis in solution in FIG. 43A and condensation of silanols on the silica dioxide surface in FIG. 43B.
Figure 43B:
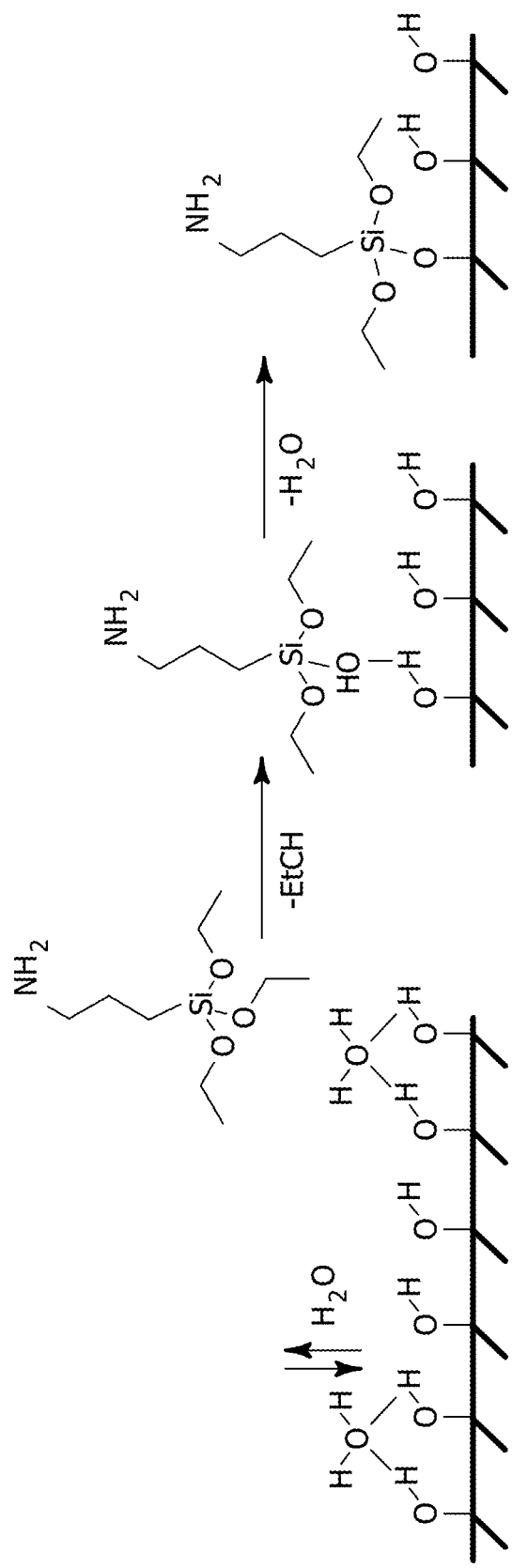

Consider molecular covalent immobilization of antibodies to carboxyl groups through an amide linkage. The sensing area is incorporated into the wave-guides. For example, the amino-terminated organic thin films from the treatment with silane agent 3-aminopropyl triethoxysilane (APTES), on a silica dioxide waveguide on a SAW device, can allow further chemical derivatizations of surface amino groups leading to the introduction of N-hydroxysuccinimide (NHS) esters, hydrazide and maleimide esterase seen in FIG. 42. A consensus regarding APTES film formation is that salinization begins with hydrolysis of the ethoxy groups in APTES, a process catalyzed by water, leading to the formation of silanols, as seen in FIG. 43A. The APTES silonals then condense with surface silanols forming a monolayer of APTES via lateral siloxane network in which amino groups are oriented away from the underlying silica dioxide surface, as seen in FIG. 43A. Other configurations are shown in FIG. 43B.

Silica-based substrates containing these grafted chemical groups have been frequently adopted for site-controlled immobilization of biomolecules such as antibodies, during the fabrication of immunoassay-based biosensors.

Spacer Molecule

To improve specificity and geometrically optimized layering of antibody fragments, the illustrated embodiments use a spacer molecule—a ternary surface monolayer, comprised of co-assembled thiolated capture probes. As shown by the experimental data, the ternary spacer provides the highest signal-to-noise ratio of biological capture with a single application of the mixture between the antibody and the spacers. In one of the embodiments, the use of ternary surface monolayers for ultrasensitive (Zeptomole) detection of nucleic acid hybridization without signal amplification is employed. Pluronic F127 (Sigma Aldrich, St. Louis, Mo.) is adsorbed to obtain a nonfouling surface for highly selective Bcl-2, VEGF, P53 and other biomarkers probes to capture the analyte, an essential step for a diagnostically applicable sensor as it increases specificity and capture statistics. The Pluronic, a tri-block copolymer whose non-fouling nature is mediated by its two polyethylene glycol (PEG) chains, prevents other molecules from non-specifically attaching to the sensor surface. The sensor is submerged in 10 µg/ml Pluronic F127 in deionized water for one hour and then rinsed with deionized water.

Figure 36B:
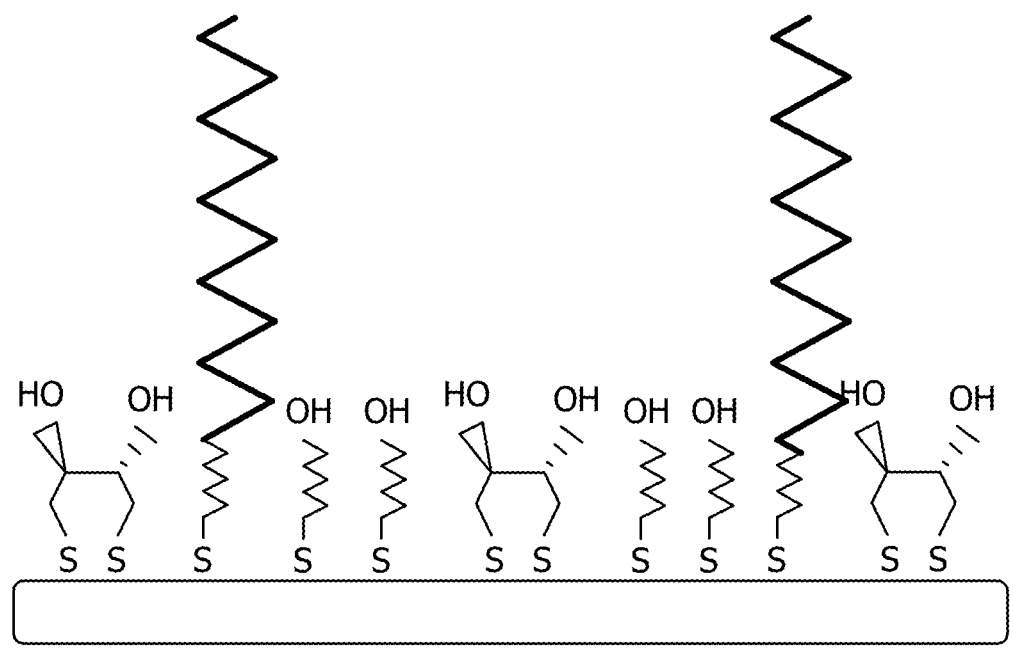

In the illustrated embodiments, we will incorporate a ternary surface monolayer as a more recent study has shown that such a surface enhances DNA hybridization and increases sensitivity. A facile surface functionalization process, similar to the one introduced by Wu et al, 2010 where a detection of specific DNA sequences in clinical samples is a key goal of studies on DNA biosensors and gene chips. This application incorporates a highly sensitive electro-chemical probe for direct measurements of specific DNA sequences in undiluted and untreated human serum and urine samples. Such probe relies on a new ternary interface involving hexanedithiol (HDT) co-immobilized with the thiolated capture probe (SHCP) on gold surfaces, followed by the incorporation of 6-mercapto-1-hexanol (MCH) as diluents. The performance of ternary monolayers prepared with linear dithiols of different lengths is systematically examined, compared and characterized by cyclic voltammetry and electrochemical impedance spectroscopy, with HDT exhibiting the most favorable analytical performance. The new SHCP/HDT+MCH monolayer, led to a 80-fold improvement in the signal-to-noise ratio (S/N) for 1 nM target DNA in undiluted human serum over the common SHCP/MCH binary alkanethiol interface, and allowed the direct quantification of the target DNA down to 7 pM (28 amol) and 17 pM (68 amol) in undiluted/untreated serum and urine, respectively. It also displayed attractive antifouling properties, as indicated from the favorable SNR. These attractive features of the SHCP/HDT+MCH sensor interface indicate considerable promise for a wide range of clinical applications and the alkanedithiol dithiothreitol (DTT), followed by the assembly of the specific antibody. This ternary self-assembled monolayer (SAM) assembly dramatically improves the signal-to-noise characteristics and lowers the detection limits of SAM-based DNA while functionalizing the sensing lane of the SAW biosensors. The two types of surfaces are shown in FIGS. 36A and 36B.

The SAW device is then used to perform micro gravimetric analysis. The LiTaO$_3$ substrate (36°, y-cut, x-propagation LiTaO$_3$) with a polydimethylsiloxane (PDMS) microfluidic channel biosensor was used to determine DNA hybridization to the probe on the gold-coated surface. The gold-coated sensing area on the SAW device is incubated 8 hr. in thiolated DNA at a concentration of 0.5 µM, then incubated another 8 hr. in a 5 µM Tris phosphine hydrochloride in 200 nM Tris-HCl buffer solution at pH 7.4. The resulting sensing lane (The reference lane is treated with the same procedure) is rinsed in distilled deionized water. The phase or frequency shift in the SAW device is then measured. The mass of the modified crystal is monitored by observing the phase shift in the resonance frequency after attachment. The shift is also measured after hybridization of the target DNA to the probe. From this procedure employing the phase shift output(s) and the amplification as well as the logarithmic scaling of the output, the apparatus AFE and its analog computation module tailored the output signal for the GUI, where the results of the measured event is displayed, this process can extract the amount of DNA that bound and use a correlation to deduce the starting concentration of DNA in the sample.

Boundary Condition for Limit of Detection

As outlined by our application, the optimization of the SH SAW biosensor is a task, which require a careful tailoring of the boundary conditions of the sensor platform. The process of improving LOD by increasing the bandwidth of the sensor, its accuracy and resolution must address the different disciplines of the sensor construction:

a) Crystal resonator with electro-acoustic characteristic such as selected by this application, namely the use of 36°, Y-cut, X-propagation LiTaO$_3$.

b) Microfluidic chamber integrated with its interdigitated input/output electrodes with their tailored wave energy (frequency domain) and their appropriate frequency matching as defined by algorithm noted in this application.

c) Electronic interface such as proposed by the novel analog front end (AFE) and its computational module.

d) Algorithmic data analysis and reporting residing with the microcontroller of the proposed apparatus.

e) Biochemical probe suitable for detection with LOD meeting clinical threshold value, and where false positive or false negative are eliminated. This process is detailed and defined by the use of compact layering of antibodies, fragmented Ab, the use of spacer-molecule, and the implementation of regimented chemical recipe to accommodate a commercially priced fabrication methodology.

f) Protein engineering using phage display in combinatorial library to generate highly specific antibody with high affinity exceeding monoclonal antibody (mAbs) capture statistics, where the sensing lane of the sensor is deployed.

g) Combinatorial antibody library technology represents a powerful tool for discovering and designing antibodies that bind targets with high affinity and specificity cloned antibody genes in single-chain Fv (scFv) or Fab format for convenient manipulation and where the DNA encoding that sequence, permits a functional linkage between target recognition and sequence replication that facilitates the rapid screening and identification of polypeptides with novel and desirable properties.

Although historically, combinatorial antibody library technology has represented a powerful tool for discovering and designing antibodies, that bind targets with high affinity and specificity, this application adapts this technology in order to improve the limit of detection by the ability of such antibody phage display libraries. Antibody phage display libraries obviate the need for lengthy development and laborious hybridoma protocols for obtaining a specific mAbs with the potency required to improve diagnostic measure as envisaged by this application. The technique, which directly cloned antibody genes in single-chain Fv (scFv) or Fab format for convenient manipulation, and, importantly, can be derived from the human antibody repertoire. In the phage-display screening format antibodies fused to the capsid or "coat" proteins of filamentous bacteriophage are displayed for targeted selection on the phage particles that also encapsulate the cognate genes. Hence, the structural linkage between a polypeptide sequence expressed on the phage surface, and the DNA encoding that sequence, permits a functional linkage between target recognition and sequence replication that facilitates the rapid screening and identification of polypeptides with novel and desirable properties. These properties associated with the technique noted above is the mainstay of the application as it will result in an improved LOD based on improved specificity, multi-epitope sites capturing the analyte in question, improved density packing of antibody with proper orientation, all of the above and many of the associated embodiments of the DNA-encoded library is the aim of this application in achieving a femtomolar concentration limit of detection.

Figure 38A:
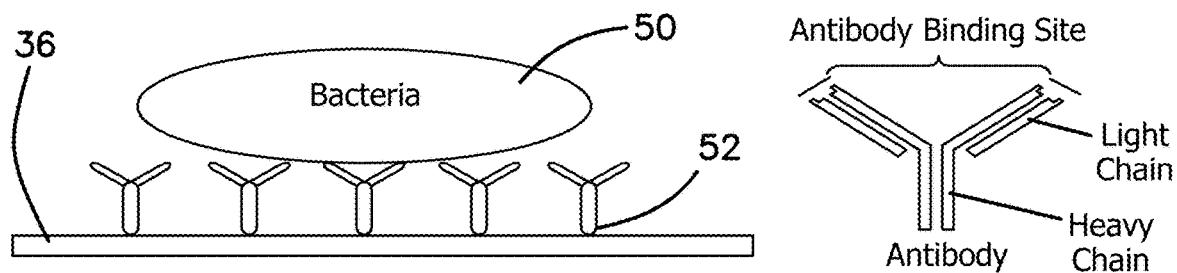
FIGS. 38A-38D diagrammatically illustrate four examples of methods by which a phage display in combinatorial library enable the production of multi-epitope antibodies enabling improved specificity of capture.
Figure 38B:
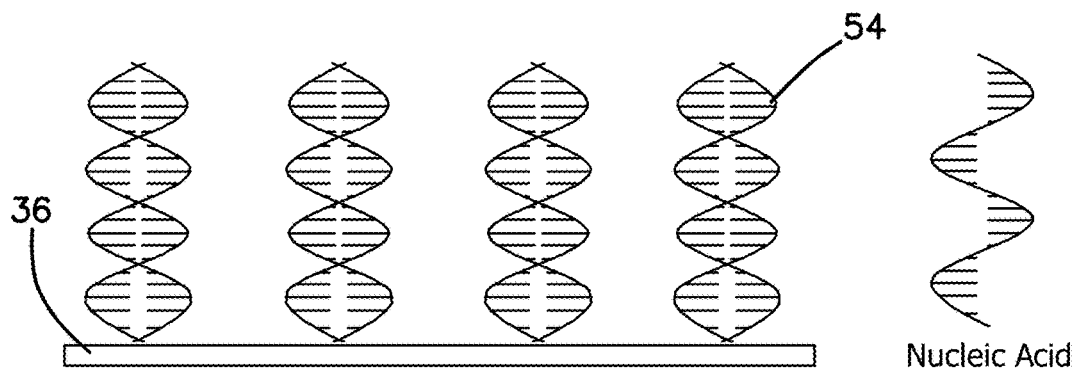
Figure 38C:
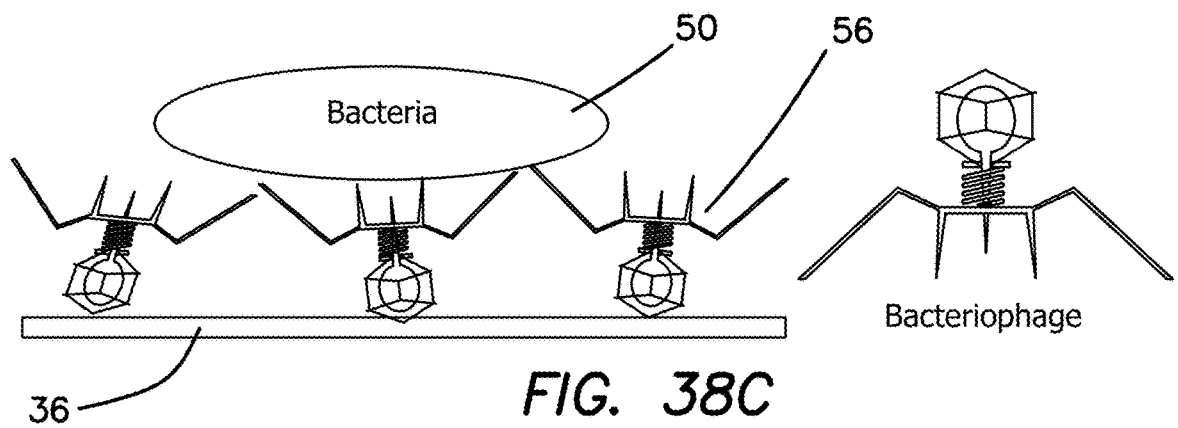
Figure 38D:
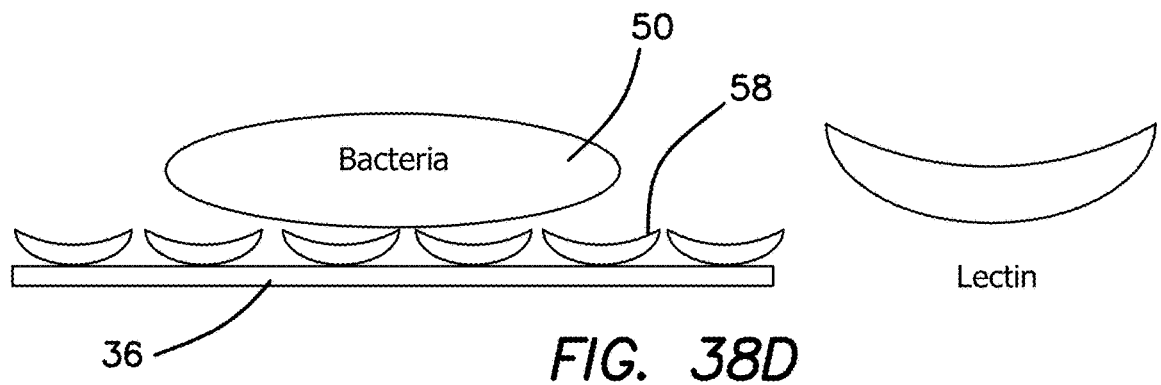
Figure 38E:
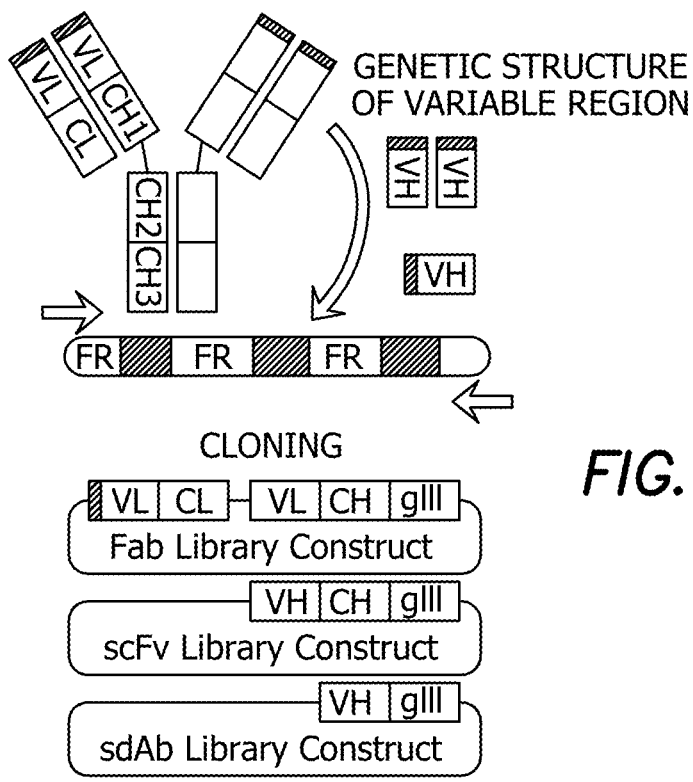
FIGS. 38E-38F are a graphic illustration and examples of implementation of an encoded DNA library and a method for generating a combinatorial antibody classes using phage display for the diagnostic purpose for minimizing the LOD to a femtomolar concentration.

FIG. 38E is a schematic diagram of the structure of a typical IgG molecule. As noted in the previously cited paper by Lerner et al, and further described in International Immunology 26(12), August 2016, by Chan et al, "The Role of Phage Display in Therapeutic Antibody Discovery", each antibody comprises two heavy and two light chains each of which have four and two immunoglobulin domains, respectively. The application notes the process of formation of such libraries as an exemplary use of these libraries, where such technique is known to those familiar with the art, but such use is not prevalent in the diagnostic arena, and where this application employs such technique to amplify the detection limits and lower the LOD to a level commensurable with clinically relevant measure.

The first domain is variable and determines specificity (VL and VH) while the second domain of the light chain (CL) and the second to fourth domains of the heavy (CH1-3) are constant across all antibodies of the same isotype. The light chain and first two domains of the heavy chain form the Fab, which is the portion expressed on the phage. The last two domains of the heavy chain form the Fc and are responsible for immune function through engagement of receptors on immune cells. Heavy and light chains are linked through a single disulfide bond (orange) between the CL and CH1 domains and the two heavy chains have multiple disulfide bonds at the hinge region between the CH1 and CH2. An scFv consists of just variable light and variable heavy domains joined by a flexible polypeptide linker while a single domain antibody (sdAb), as the name implies, is only a single immunoglobulin (usually VH) domain which is sufficient for binding. (B) Variable domain genetic structure and construction of a natural phage display library. Each variable domain consists of three hyper variable CDRs interspersed between the more conserved framework regions (FRs). The immuno-globulin domain folds such that the CDRs are brought together to form the antigen-binding surface at the tip of the Fab. Degenerate primers (arrows) are used to amplify the entire variable heavy and light chains (or alternatively variable and first constant domain) from a source of B cells and cloned in-frame with the phage coat protein (usually gene III) into E. coli to produce an Fab, scFv or sdAb library. The rest of the phage genome is supplied through replication defective helper phage to produce antibody-displaying phage.

Figure 38F:
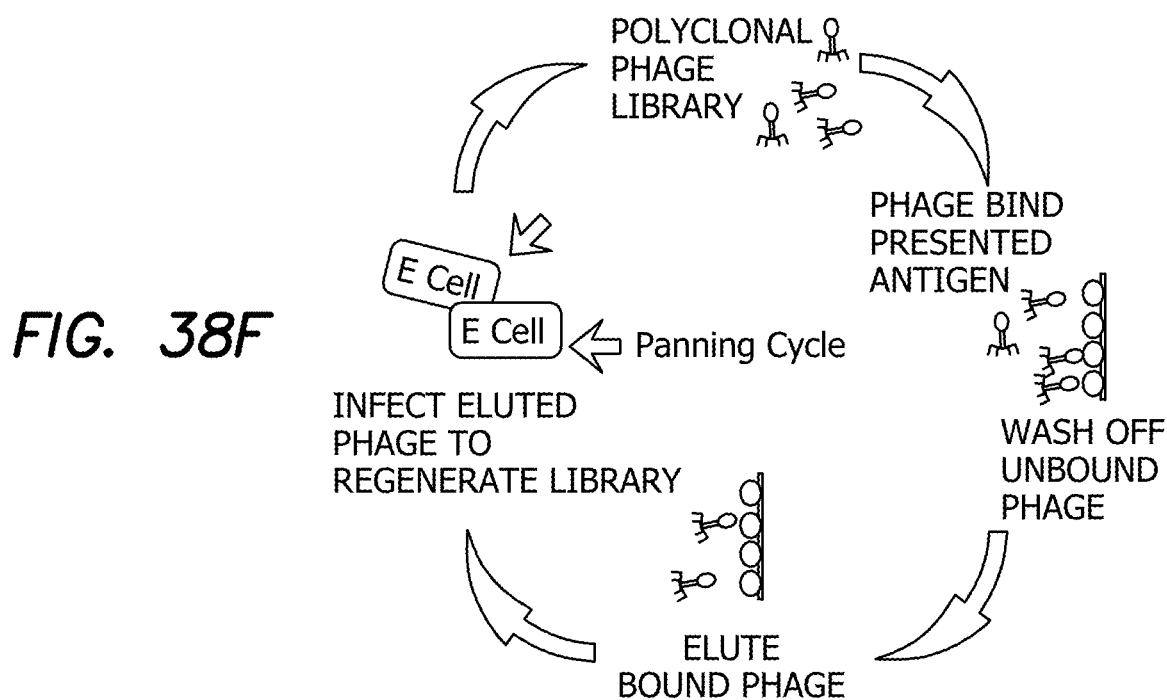

FIG. 38F is a diagram demonstrating a general method for phage panning. Polyclonal phage expressing recombinant antibodies on their surface is applied to target antigen presented as either immobilized on a magnetic bead, polystyrene surface or on the surface of a whole cell. Phage carrying antigen-binding Fab bind and non-specific Fab are removed through stringent washing. Antigen-bound phage is eluted off, either typically through pH change, or protease digestion and re-infected into E. coli, from which a new library enriched for antigen-binding clones are made. After several cycles, the library would be sufficiently enriched so that the individual clones can be isolated from E. Coli stock, expressed as monoclonal phage, tested, sequenced and the specific antibodies expressed recombinantly.

Selection of Biochemical Probe

The past few years, multiple protein biomarkers have been suggested as a diagnostic target based on genomic or proteomic studies. Devices such as biosensors that could measure those biomarkers rapidly (e.g. within 10 minutes) and at very low concentrations (e.g. at fg/ml) would be advantageous in diagnostic development. In particular, the capacity of the biosensor to meet challenges such as sensitive detection and low-level quantification of analytes will undoubtedly put them as Point of Care Standard. Biosensors are built up of a biological target-recognition element (the probe) connected to a transduction element using a suitable interface layer. Binding events occurring at this functionalized interface layer are translated by the transducer into an analytical data point and then displayed on a suitable GUI as indicated by this application. These biosensors provide a rapid, convenient, low cost alternative to conventional analytical methods such as, ELISA, PCR or Mass-Spectrometry, for detecting or assaying a biomarker.

One of the essential embodiments of this application, address the fact that LOD and resolution of the sensor performance must address the advances made through proteomic analyses for generating biomarkers, which possess highly specific probes able to recognize those targets. Antibodies are considered the first choice as molecular recognition units due to their target specificity and affinity, which make them excellent probes in biosensor development. However, several problems such as difficult directional immobilization, unstable behavior, loss of specificity and steric hindrance, may arise from using these large molecules. Protein engineering techniques offer designed antibody formats suitable for biomarker analysis, the minimization strategies of antibodies into fragment antigen binding (Fab) fragments, single chain variable fragment (scFv) or even single-domain antibody fragments like heavy ($V_H$), light ($V_L$) chains of immunoglobulins or single-domain antibody fragments (VHHs) are fabricated as is further detailed by this application with its appended figures and their accompanying description.

A diagrammatic depiction of an IgG antibody is shown in FIG. 41, which outline the use of the fragment antigen binding. The F(ab) fragment is an antibody structure that still binds to antigens but is monovalent with no Fc portion. An antibody digested by the enzyme papain yields two F(ab) fragments of about 50 kDa each and an Fc fragment.

In contrast, F(ab')2 fragment antibodies are generated by pepsin digestion of whole IgG antibodies to remove most of the Fc region while leaving intact some of the hinge region. F(ab')2 fragments have two antigen-binding F(ab) portions linked together by disulfide bonds, and therefore are bivalent with a molecular weight of about 110 kDa.

Figure 37A:
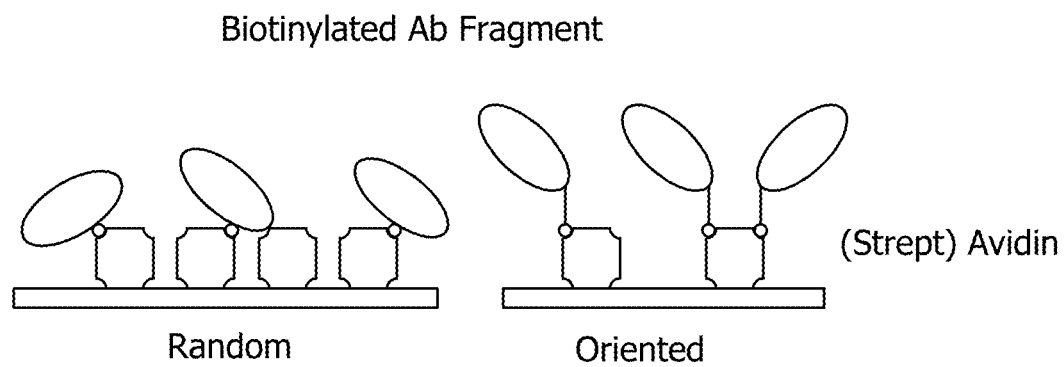
FIGS. 37A-37C illustrate three examples of antibody fragments optimized sensing surfaces.
Figure 37B:
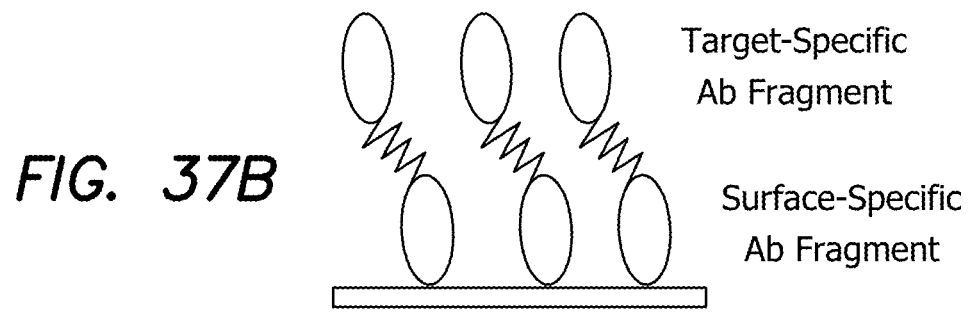
Figure 37C:
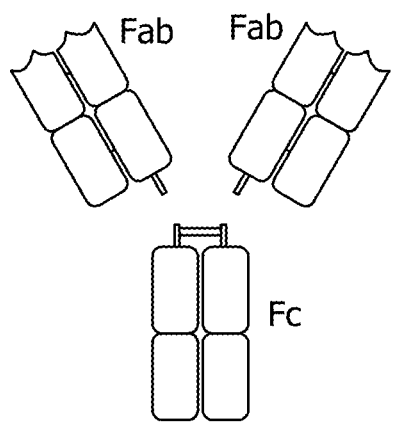

Not only the size of the probe but also other issues like choice of immobilization tag, type of solid support and probe stability are of critical importance in assay development for biosensing. In this respect, multiple approaches to specifically orient and couple antibody fragments in a generic one-step procedure directly on a biosensor substrate are employed. FIGS. 37A-37C illustrate three examples of antibody fragments optimized sensing surfaces. FIG. 37A illustrated a random biotinylated Ab fragment as compared to an oriented biotinylated Ab fragment using (strept)avidin. A study by Cho I H at el, titled "Site-directed biotinylation of antibodies for controlled immobilization on solid surfaces". Anal Biochem. 2007 Jun. 1; 365(1):14-23. The study noted above describes a site-directed biotinylation of antibodies at the hinge region, developed to immobilize antibodies in an oriented manner via biotin-streptavidin linkage. When intact antibody is biotinylated with maleimide-activated biotin after reduction, the reaction preferentially occurred at the sulfhydryl groups between the C(H1) and the C(L) domains and, provided that the reagent concentration exceeded a certain level, at those between the C(H2) and the C(H2) domains at the hinge. Based on this result, the authors devised an approach in which free maleimide was added to compete with the activated biotin for the preferential sites between the C (H1) and the C (L) domains. Since the smaller molecular size of free maleimide made it more accessible for the reaction than biotin, maleimide bound to the groups between the C(H1) and the C(L) domains first and thus conceded the groups between the C(H2) and the C(H2) domains to biotin under optimal conditions. In an alternative approach, selective biotinylation at the hinge was also achieved by reacting activated biotin with F(ab') (2) fragment prepared by enzymatic cleavage. This result indicated that, when free of Fc, the hinge structure, which contains the functional groups, of the fragment was open, allowing easy access to the biotin derivative from the aqueous medium. Both site-directed biotinylation preparations were tested as capture antibodies in sandwich-type immunoassays and compared to whole antibody randomly biotinylated at amino groups on the molecule. Preparations of both the intact antibody and the F(ab') (2) showed consistently enhanced detection capabilities that were 2.6 and 20 times that of the control, respectively. FIG. 37B diagrammatically illustrates a surface-specific Ab fragment bound to a target-specific fragment. FIG. 37C illustrates two Fab fragments bound to a single Fc fragment. In one preferred embodiment, the application employs the technique of fragmented antibody in order to improve specificity, statistical capture rate, stability of the conjugating event, all the above features are set as the combined strategy for the purpose of optimizing the sensor sensitivity, by increasing the frequency, which results in minimizing the LOD of the analyte concentration.

Analyte-Example-Biomarkers as Prognostic Indicator

In a study titled "Molecular Biomarkers for Breast Cancer Prognosis: Expression of c-erbB-2 and p53 Prognostic Value of Vascular Endothelial Growth Factor in Breast Cancer", the authors describe selective capture of protein B-cell lymphoma 2 (Bcl-2), which is elevated in many cancer types including ovarian cancer. The immunosensor was designed, fabricated, and experimentally characterized. An application-specific surface functionalization scheme with monoclonal antibodies, protein A/G and Pluronic F127 was developed and applied. Characterization was done using the oscillation frequency shift of with sensor used as the feedback element of an oscillator circuit. Detection of Bcl-2 with target sensitivity of 0.5 ng/ml from buffer solutions was presented. A linear relation between frequency shift and Bcl-2 concentration was observed. The selectivity was shown with experiments by introducing another protein, in addition to Bcl-2, to the buffer. It was seen that similar detection performance of Bcl-2 was obtained even with presence of control protein in very high concentrations. The results were also analyzed with perturbation equations. This study and others cited by the literature demonstrate the prognostic value of a label free surface acoustic biosensor. However, it is clear that the needs for a robust, hand held device with the embodiments cited by this application, will render such capabilities and use to the entire class of disease model, whereby the medical staff will be able to improve the detection and treatment modality for the patient and its personalized approach to medicine. A diagrammatic depiction of four examples of antibody capture is illustrated in FIGS. 38A-38D. FIG. 38A is a diagrammatically shows bacteria 50 bound to surface 36 by one or more specific antibodies 52. FIG. 38B diagrammatically shows surface 36 functionalized by nucleic acids 54. FIG. 38C diagrammatically shows bacteria 50 bound to surface 36 by one or more bacteriophages 56. FIG. 38D diagrammatically shows bacteria 50 bound to surface 36 by one or more molecules of lectin 58, an agglutinating protein. All the above illustrations are a mere examples of the methods by which this application address the ability of such biosensing modality employing a SH SAW technology to account for detection of biological species in an assay under the minimal LOD of femtomolar resolution.

SAW Platform with PDMS Microfluidic Chip

The integration of a microfluidic chamber with the SH SAW biosensor allows for the liquid buffer with analyte to be dropped directly on the sensor surface, leading to liquids flows with inconsistent results. To minimize insertion losses as well as solve the acoustic reflection associated with the wave propagation, this application is directed to resolve the limitations noted by the prior art, whereby insertion losses (IL), and flow of buffer with the analyte turbulence are minimized. The setting of boundary conditions for such errors with the use of an integrated microfluidic chamber is described by defining the limits of acoustic wave phase (Vp) and group (Vg) velocity where the relative frequency shift is linear and is defined. Employing the following relation we adapt an objective measure for the insertion loses and their contributing elastic/mechanical elements;

$$\frac{\Delta f}{fo} = \frac{Vg}{Vp}\frac{\Delta V}{Vp}$$

The acoustic sensor is based on a piezoelectric delay line with a transmitter and a receiver comprised of interdigital transducers (IDTs) to create and propagate an acoustic wave through an aqueous medium. The integration of the SH SAW sensor with its microfluidic chamber, necessitate the formation layers comprised of a quartz substrate, transmitter and receiver IDTs and a $SiO_2$ guiding layer, which form the waveguide. In this application, the sensor is formed out of $LiTaO_3$ quartz substrate with a cut at 36° angel rotated on the Y-axis relative to X crystallographic axis with the IDT wave propagation perpendicular to $X_j$ crystallographic axis.

Lab-On-Chip for shear horizontal polarization of SAW limits dispersion in liquid and insertion losses. However, in a highly viscous environment, insertion losses due to viscous coupling increase drastically. While using the sensor in an oscillator loop, it leads to a limitation in the measurable viscosity range, as the oscillation conditions, resulting in suboptimal performance due to insertion loses which cannot be satisfied, unless a modification to the echo chambers are mitigated. To overcome this limitation, the illustrated embodiments, employ a microfluidic polydimethylsiloxane (PDMS) chip bonded on the acoustic sensor.

The bonding ability of PDMS allows, due to an UV ozone treatment, the creation of covalent bonds between microfluidic chip and $SiO_2$ guiding layer. PDMS is also acoustically absorbent, and has a low elastic shear modulus compared to the $SiO_2$ guiding layer.

Compared to classical experimental apparatus, where liquids are dropped directly on the sensor surface, the illustrated embodiment uses a liquid flows manifold where the flow characteristic is automated leading to a consistent application of hybridization kinetics and reduced statistical errors in interface manipulations. Thanks to decreased insertion losses, highly viscous environments are sensed in an oscillator set-up, without the insertion losses due to viscous coupling.

Figure 24:
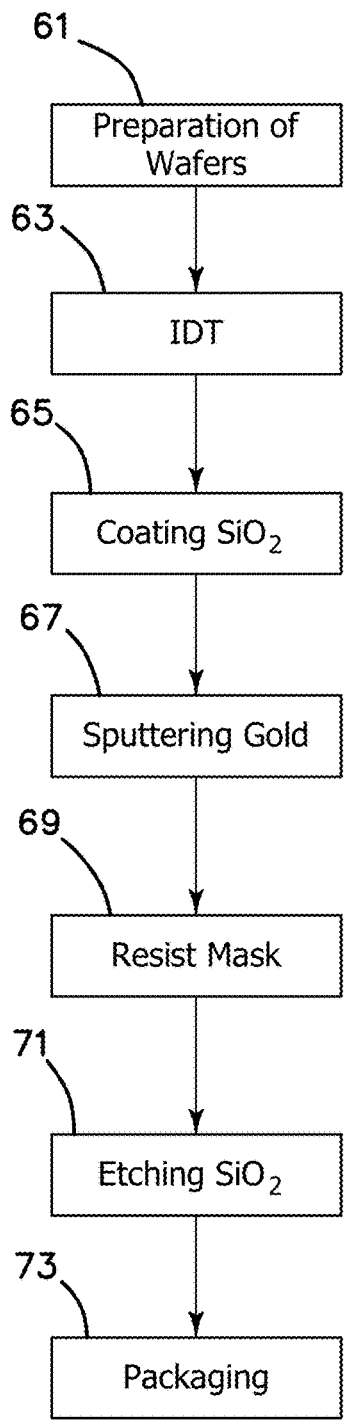
FIG. 24. Schematic for the fabrication of a surface acoustic wave biosensor on a LiTaO$_3$ substrate (36°, y-cut, x-propagation LiTaO$_3$) with a PDMS microfluidic channel for whole cell, protein biomarker and nucleic acid detection in real-time.
Figure 24:
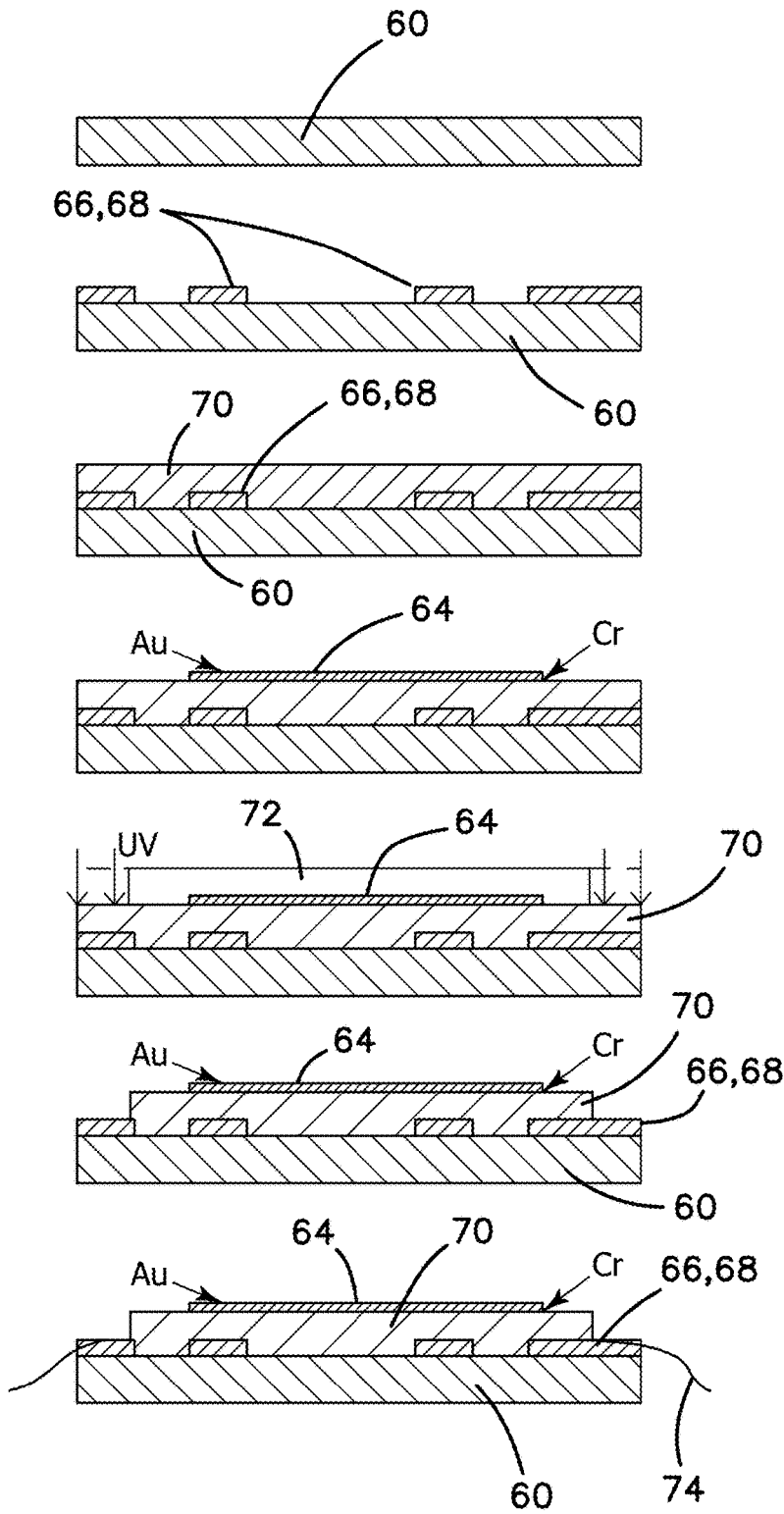

The new SAW-based biosensors are designed and fabricated in a series of relatively simple lithographic steps, as outlined in FIG. 24. The $LiTaO_3$ piezoelectric layer 60 is prepared in step 61 and aluminum IDTs 66, 68 selectively disposed on layer 60 as step 63. A $SiO_2$ layer 70 is disposed over the IDTs 66, 68 and exposed portions of piezoelectric layer 60 at step 65. A gold/chromium sensitive layer 64 is sputtered onto selected portion of $SiO_2$ layer 70 at step 67. A photoresist mask 72 is selectively disposed over sensitive layer 64 and certain exposed portions of $SiO_2$ layer 70 and cured with ultraviolet light at step 69. The portions of the $SiO_2$ layer 70 left exposed by the photomask 72 are etched away at step 71 providing electrical access to selected portions of the metallization or IDTs 66, 68 at step 71, the photomask 72 removed. Wire bonding to the selected portions of the metallization or IDTs 66, 68 and other packaging or passivation processes or structures, terminating with wire pads 137 are put into place at step 73.

Figure 39A:
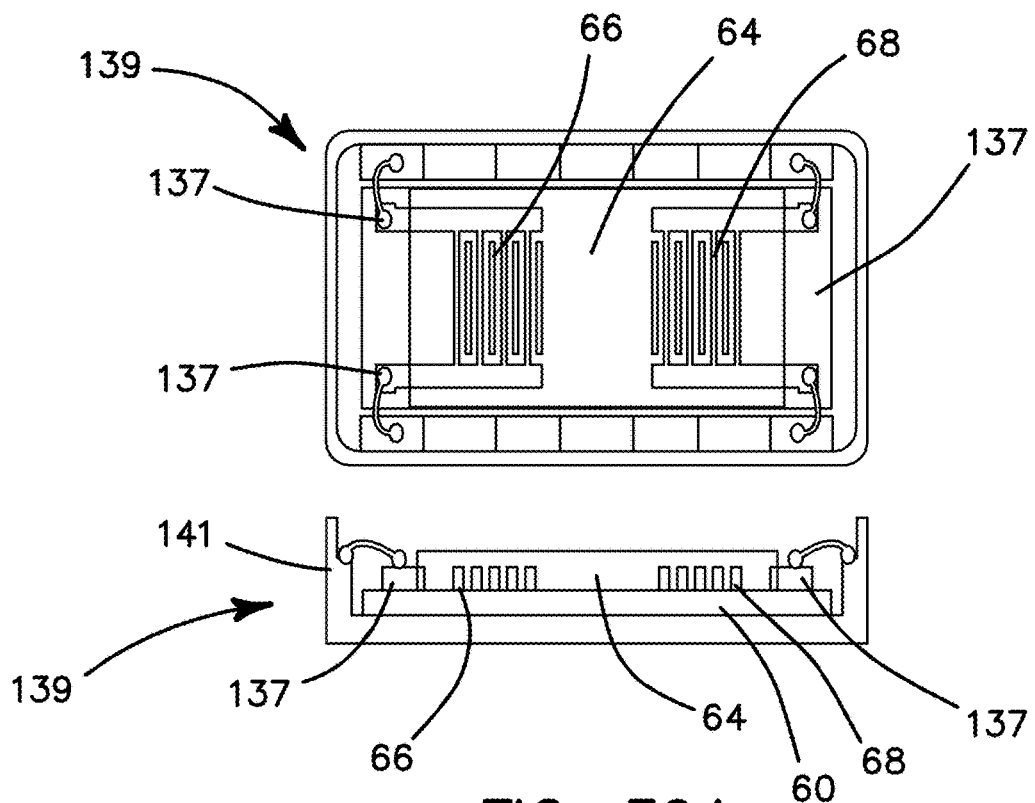
FIG. 39A is a schematic of the microfluidic saw device with the PDMS microfluidic channels with the structure of the sensor array shown in FIG. 39B.
Figure 39B:
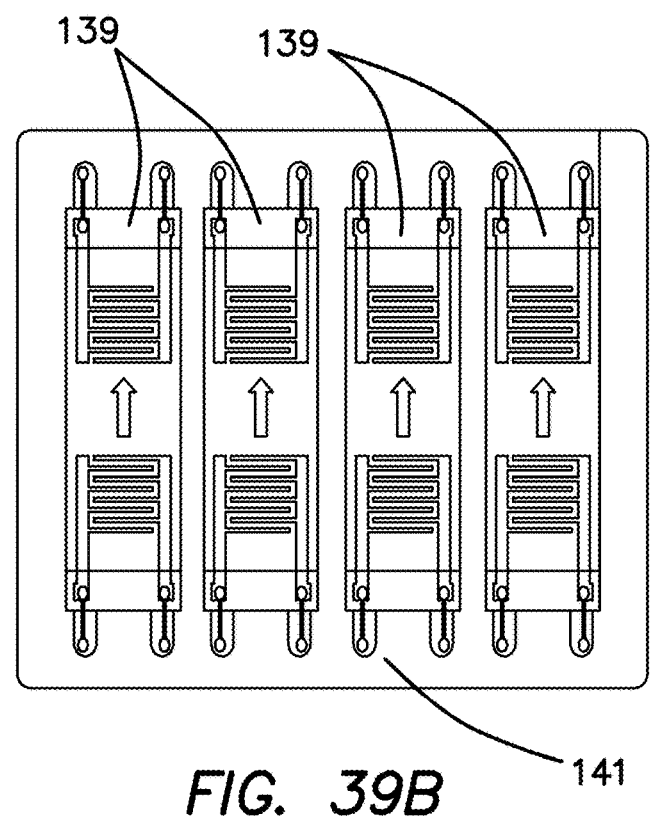

A $LiTaO_3$ Love-Wave biosensor is used for detecting pathogens, protein biomarkers and nucleic acids on a series of related platforms. These devices feature a $LiTaO_3$ substrate with a $SiO_2$ guiding layer, an optional 100 nm gold metallic layer covering the guiding layer, and two sets of interdigitated gold electrodes. A PDMS microfluidic system delivers the sample. The sensor is prepared similarly to the biosensor produced by Zhang et al. 2015; however, the device we use employs antibody fragments and not full-length antibodies. Additionally, we use a ternary surface treatment for efficient immobilization of DNA on the optional gold metallic layer for nucleic acid immobilization. A schematic of the microfluidic SAW device 139 is shown in FIG. 39A with the PDMS microfluidic channels with the structure of the final array of multiple devices shown in FIG. 39B. FIG. 39A shows a single microfluidic SAW device 139 is a side cross-sectional view included in a surface mounted SMD package 141 and electrically connected through wire pads 137. FIG. 39B is a plan view of a plurality of devices 139 mounted on a PCB in an SMD package 141.

Microfluidic Channel-Micro Channel-Guided Antibody Patterning of Antibody-Coated Gold Nanoparticles for Multiplexed Biosensing In this section, a method is presented to enhance a rapid fabrication of custom arrays of targeting molecules, on silica dioxide ($SiO_2$) substrate using a microchannel to guide a flow of gold nanoparticles by a gravity driven flow. The commercially available 40-nm gold nanoparticles in citrate buffer provide a robust surface to graft capture antibodies. The different target antigens are subsequently bound and analyzed in parallel in different microfluidic channels on a single sensing device. This technique allows multiplexed detection on a single platform.

The fabrication and control of a nanostructure on $SiO_2$ or any other silica-based polymer are subjects of interest to many surface chemists. Nobel metal nanoparticles exhibit unique chemical, optical and physical properties. These include the fact that gold does not form oxides, easily forms a strong bond with sulfur containing molecules and is a coinage metal. Gold (Au) nanoparticles (GNP) also exhibit unique optical responses that are absent in bulk gold of localized surface plasmon resonance (LSPR). Therefore, Au nanoparticle-based nanostructures produce elaborate label-free mass sensing devices. As shown in FIG. 24, using a bottom-up approach, colloidal suspensions of gold nanoparticles are deposited on a surface by self-assembly. The gold nanoparticles are protected by bifunctional alkyl thiol, which permit the formation of covalent chemical bonding with various surfaces. However, nanoparticles used to synthesize these structures only have diameters that are less than 10-nm. The technique cannot be applied when larger nanoparticles are required e.g. 20-nm. Several research groups have reported that GNPs in a citrate buffer are strongly adsorbed on glass surfaces coated with bifunctional organosilanes.

The following process is followed in order to fabricate a GNP surface layer: A fabricated lithium tantalate ($LiTaO_3$) shear horizontal surface acoustic wave (SH SAW) device with a silica dioxide ($SiO_2$) guiding layer; 40-nm gold nanoparticles (GNPs) in citrate buffer (aqua regia (3:1 HCl:HNO3); dilute alkaline detergent; a 3-Aminopropyl-triethoxysilane (APTMS) and ethyltrimethoxysilane (ETMS) mixture; a Su-8 photo-resist Bisphenol A Novolac epoxy; polydimethylsiloxane (PDMS); ultrapure water; phosphate buffered saline (PBS); and Thiol terminated nucleic acid, protein or carbohydrate targeting molecule. This treatment of the sensing lane creates a 3-dimensionally seeded surface to enable high compaction of the capture probe on the limited surface available on a SAW sensor.

Experimental Setup and Procedure

Creation of molecular functionalized sensing zones for the SH SAW devices in an array format is realized as follows. Knowing the geometry of the interdigitated (IDT) input and output electrodes, the size of the sensing area is determent by the optimization algorithm. The dimensions (area) of the surface over which the acoustic wave travels provides the dimensions of the area needed to form a monolayer of GNP that are functionalized with a targeting molecule i.e. an antibody, nucleic acid or carbohydrate such as wheat germ agglutinin.

Figure 26A:
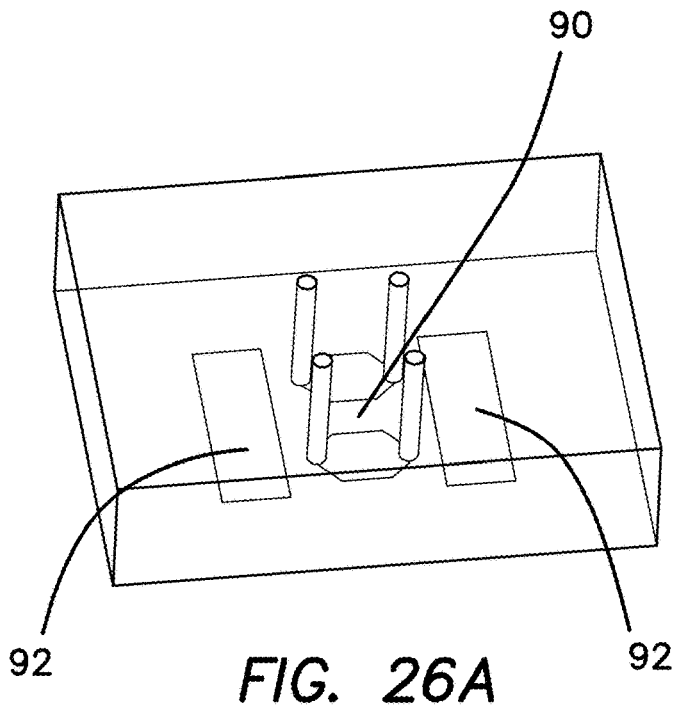
FIGS. 26A-26C are schematic depictions of the microfluidic SAW device in FIG. 26A with the PDMS microfluidic channel, in FIG. 26B showing the structure of the final device and in FIG. 26C illustrating the process flow diagram of the fabrication process.
Figure 26B:
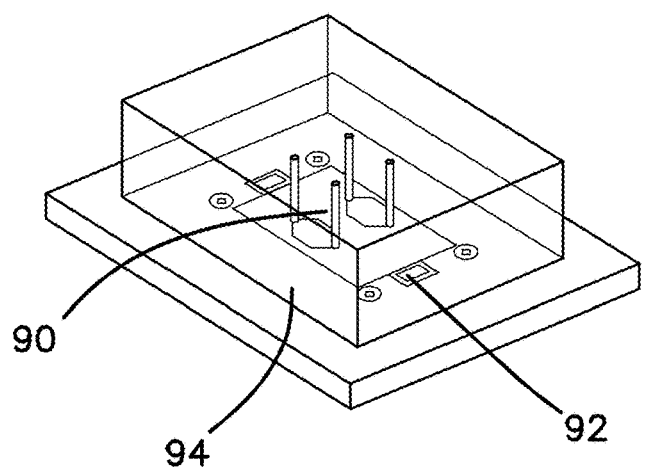
Figure 26C:
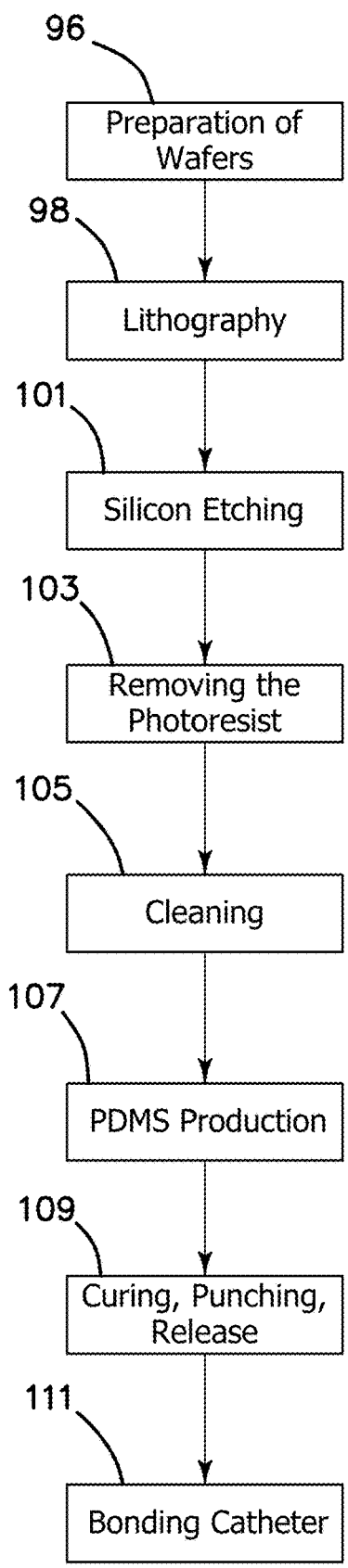

The use of a microfluidic chamber on the proposed SAW biosensor improves the functionality of the device. As indicated in this application, the use of microfluidic technology on SAW platforms has been shown to greatly enhance the device functionality. In the illustrated embodiment, the microfluidic channel components are fabricated from PDMS. PDMS is chosen for its good biocompatibility and optical transparency. The microfluidic channels were designed using the methodology as shown in FIG. 26. The center portion 90 of a defined cavity in a PDMS package as shown in FIG. 26 is the reaction chamber including the sensitive layer 64 while the rectangular sections 92 were designed to cover the IDTs 66, 68. The package device combined with a printed circuit board 94 on which the PDMS microfluidic package is mounted is depicted in FIG. 26b. A process flow diagram is shown in FIG. 26c. This embodiment employs an exemplary material such as SU-8 (SU-8 2000, MicroChem, Newton Mass. USA); The mold for casting the PDMS shown by item 90, a SU-8 (is the most common molding media used for PDMS-based microfluidic structure fabrication.) Using SU-8 with a single spin coat limits our maximum mold thickness to around 250 μm; here we will aim for a thickness of 200 μm. The process is as follows.

(1) Spin coat SU-8 polymer photoresist as poured onto a wafer substrate; Si is ideal for this purpose. Spin curves available from the vendor are useful for estimating the appropriate spin rate to obtain the desired thickness of 200 μm; here we ramp up to 500 rpm spin rate and hold for 15 s to flatten the resist, followed by a 30 s spin at 1250 rpm which gives us a final film thickness of 205±3 μm. The spin acceleration is 100 rpm/s throughout.

(2) Any bubbles seen in the photoresist must be removed, preferably by degassing the photoresist prior to use. Heating the resist to 50-60° C. will help.

(3) Prebake (soft bake) the SU-8 to evaporate its solvent in preparation for exposure. Here we prebake the SU-8 coated wafer at 90° C. on a polished Al hot plate for 75 min; we ramp up the temperature to this temperature at 5° C./min to give improved film adhesion. Generally, the thicker the film, the longer it takes to complete evaporation of the solvent; this represents one limit in the maximum thickness of the spun-on film.

(4) Mount SU-8 covered wafer with mask atop it and expose it with UV radiation with a wavelength of 350-400 nm. The vendor should provide an exposure energy estimate versus film thickness graph, but it will be at best an estimate and requires some trial and error to obtain good results. Our approach uses 500 mJ/cm2 of exposure energy on a standard mask aligner (MA-6/UV400, SUSS Microtec, Garching, Germany) with 350-400 nm UV light source.

(5) Making thicker structures can be accomplished by repeating steps 1 to 4 and then continuing onward.

(6) Post-exposure baking aids in cross-linking the exposed portions of the SU-8 in preparation for its development. This step will also require some trial and error; we ramp up to a bake of 15 min at 90° C. at 5° C./min and ramp down after this time at the same rate. Care in ramping the temperature up and down in baking will reduce the appearance of cracks and bowing from internal stresses.

(7) Development using MicroChem's SU-8 developer is straightforward, requiring about 16 min for immersion development, leaving the finished mold for use in casting. The above steps are indicated serially by the FIG. 24 and its product geometry is optional, it is shown as a mere representation of a generic microfluidic chamber.

Figure 25A:
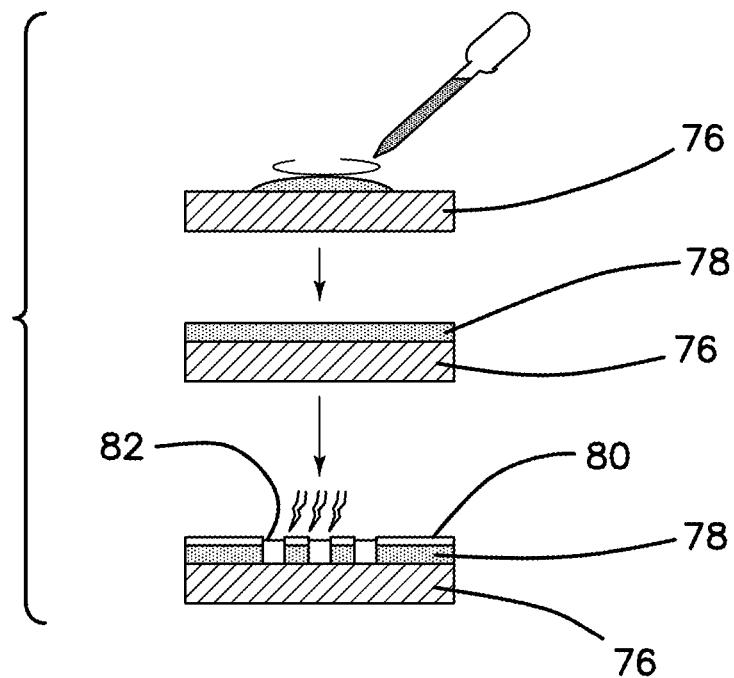
FIGS. 25A and 25B are schematic depictions of a photolithographic process of creating PDMS molds by replica modeling.
Figure 25B:
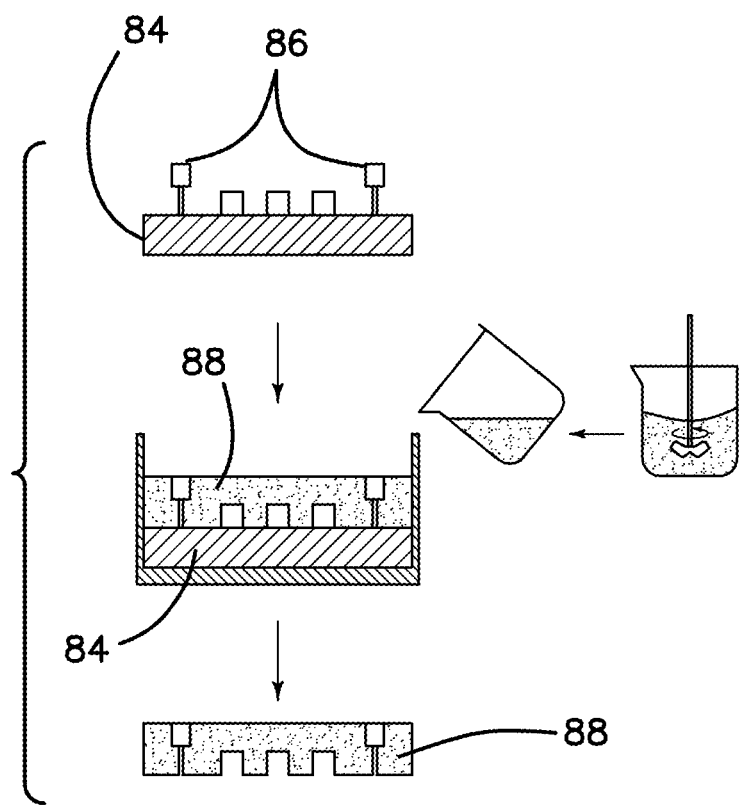

A diagram of the PDMS molding process for defining the microfluidic chambers in which is illustrated in FIG. 25, which is substantially the same as that shown in FIG. 24, namely preparing a photoresist layer 78 on a silicon substrate 76 in FIG. 25, using a mask 80 to define the microfluidic channels in FIG. 25, developing the microfluidic channels in the resist 78 in FIG. 25A, pouring the PDMS 88 and curing it over the developed microfluidic channels defined in the resist 78 in FIG. 25B, detaching the PDMS layer 88 from the resist 78 and silicon substrate 76 in FIG. 26 to result in the finished PDMS package 88 having the microfluidic channels defined therein in FIG. 26C.

Analog Computational Unit and Analog Front End

In one of the preferred embodiments, the apparatus employ a method for solving the optimization problem of SAW measure of sensitivity and the ability of the apparatus in defining the minimum threshold of the sensor's LOD. Schematically the biological event on the sensing lane of the apparatus is amplified and it is accomplished by the use of the analog front end 904, the system further is enabled by an automatic gain control circuit based on input obtained as a result of the change in phase shift measured. The rate of hybridization rate is dynamically varying, where an analog interface accommodate the kinetics in a closed-loop feedback regulating circuit described in FIG. 13. The purpose of which is to provide a controlled signal amplitude at its output, despite variation of the amplitude in the input signal, shown and described by FIG. 14. The average or peak output-signal level is used to dynamically adjust the input-to-output gain to a suitable value, further enabling the circuit, described by FIG. 15, 16, and schematically identified by block diagram in FIG. 17. This feature of the invention enable a satisfactory performance with linear and with order of magnitude range of input signal levels, and were saturation detection circuit 911 and alarm 912 with its switching resistor bank 913 are set to a minimum threshold.

To analyze how the signal is amplified when the analyte/antibody are conjugating, the system define the logarithmic amplification factor (LA) between two activated intermediates in a signal change X* and Y* (with Y* is the downstream event in the pathway). Using the following equation, the system provides selection-mechanism for the "counter", thereby enabling the apparatus to account for hybridization kinetics:

$$LA = \log\left(\frac{\int_0^T V_{Y^*}^+(t)dt}{\int_0^T V_{X^*}^+(t)dt}\right)$$

Where first, the source follower amplifier increase the signal with constant gain for the duration of stimulation event registers as t, it follow that when the LA value—the logarithm of the ratio between the total productions of both the intermediates time during the signaling process detected, defined as the minimum threshold value of detection LOD of e.g. $10^{-15}$ per volume. The total duration of an intermediate event is described in the expression noted above as the integral of the net activation rate (hybridization) during the stimulation process. Considering this definition, the event is amplified between two steps in the SAW sensing lane—(a differential output of phase-shift change between sensing lane and reference lane), the system assign value when LA is higher than "zero", and or in cases where LA is smaller than zero. The system provokes an attenuation of the signal and record the event. A value indicated by "one", implies for example, that on average, each event of X* is equal to a phase shift value of Y*, while a value of minus one (−1) represents that the threshold minimum X* produce on average nominal value below the sensitivity of the system which is the LOD minimum of Y*, and it is indicated as an "attenuation" until the threshold value is attained. This process of "counting" hybridization events act as a state machine with single parametric relating solely to analye-concentration and its rate of hybridization, thereby, providing a measure of kinetics, which is proportional to the LOD set limits, e.g. femtomolar ($10^{-15}$), or picomolar value ($10^{31\ 12}$) set by fiat.

FIG. 22A-22D are schematics of analog operational circuits that may be used in an analog computational analyzer employed by the application incorporating the principles of cellular SAW array, where a parallel computing paradigm similar to neural networks is applied in order to solve the diffusion as well as the hybridization problem for a variety of proteins and DNA captured by the apparatus 900 in a manner in which the cellular biological process-dynamics is mimicked and its underlying protein sequences observed in the sensor 1A, and where such events are counted and certain arithmetical procedures are applied. It is to be understood that many other analog operational circuits in addition to those shown in FIG. 22A-22D could be included.

Following Shannon, C E. 1941. "Mathematical Theory of the Differential Analyzer", this application employ an analog computation, which is an improved method for analytical modeling, as it resembles the physical laws (biological process of diffusion and hybridization), and where computation is realized as a continuous function, and further is observed that analog circuits often use fewer devices than corresponding digital circuits. For example, a four-quadrant adder (capable of adding two signed numbers) can be fabricated from four transistors, and where two transistors are sufficient to compute the logarithm or exponential, five for the hyperbolic tangent (which is very useful in neural computation), and three for the square root. As discussed herein, an analog computation unit is incorporated to enable the apparatus 900 with its SAW 1 in a sensor array configuration 261, to generate a data stream manipulated by the arithmetical operators such as described by FIG. 22A-22D and as shown by example of computing a derivative.

Figure 22A:
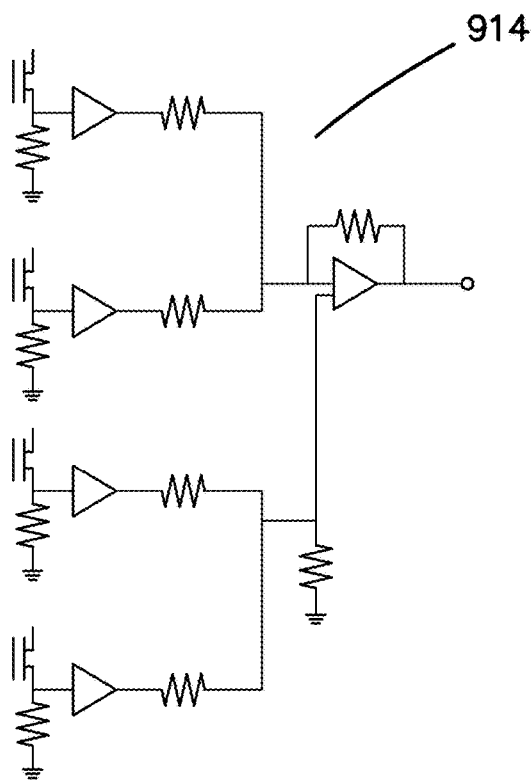
FIG. 22A-22D are schematics for the computational circuits of the illustrated embodiment incorporating the principles of cellular SAW array.
Figure 22B:
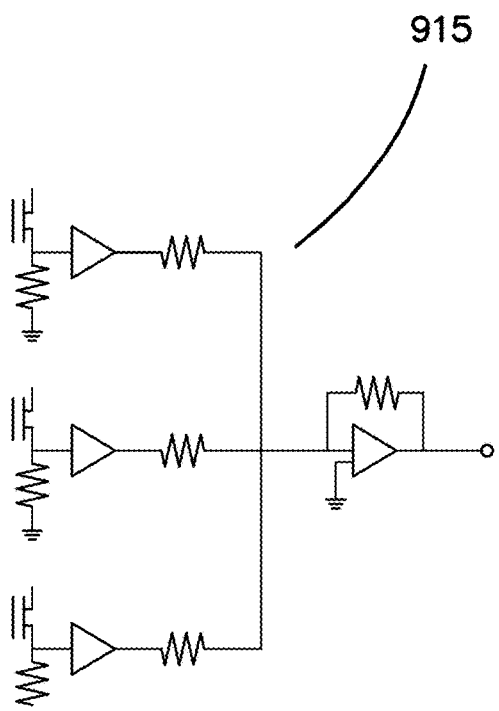
Figure 22C:
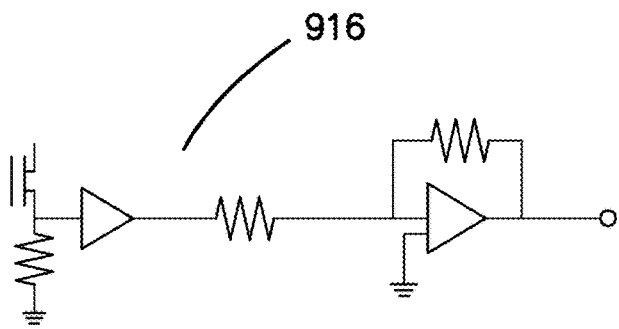
Figure 22D:
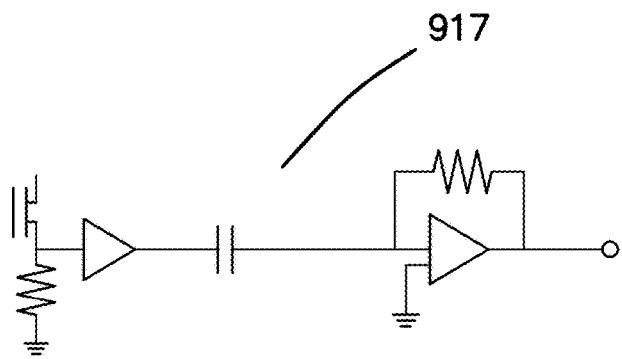

FIG. 22A shows a summing amplifier, FIG. 22B shows a difference amplifier, FIG. 22C shows an integrator and FIG. 22D shows a differentiator. The analog computation devices of FIG. 22A-22D employing the SAW cell unit 34 in an array matrix-configuration are combined and arranged to perform algebraic and integro-differential operations acting upon continuous or analog signals as required by the application at hand. The high gain D.C. source follower amplifier 27 as exhibited by the configuration of SAW cell 1 forms the basic operational element of detection. If the passive components in both feedback and input arms are entirely resistive, the circuits of FIG. 22A add the applied voltages in proportion to the ratios of the individual resistors. If the feedback impedance is capacitive, the circuits integrate the sum of the applied voltages, as shown in FIG. 22C. The simplest input and feedback impedances are replaced with complex networks, either passive or active, the amplifier circuit develops more complicated transfer functions than those shown in FIG. 22A-22D, but a general propose analog computer employing a multiplier may be used to form the product of two or more variables. In addition, a fixed and variable diode function generators are available to perform various non-linear operations, and a comparator may make elementary decisions based on the value of a particular variable.

Figure 23:
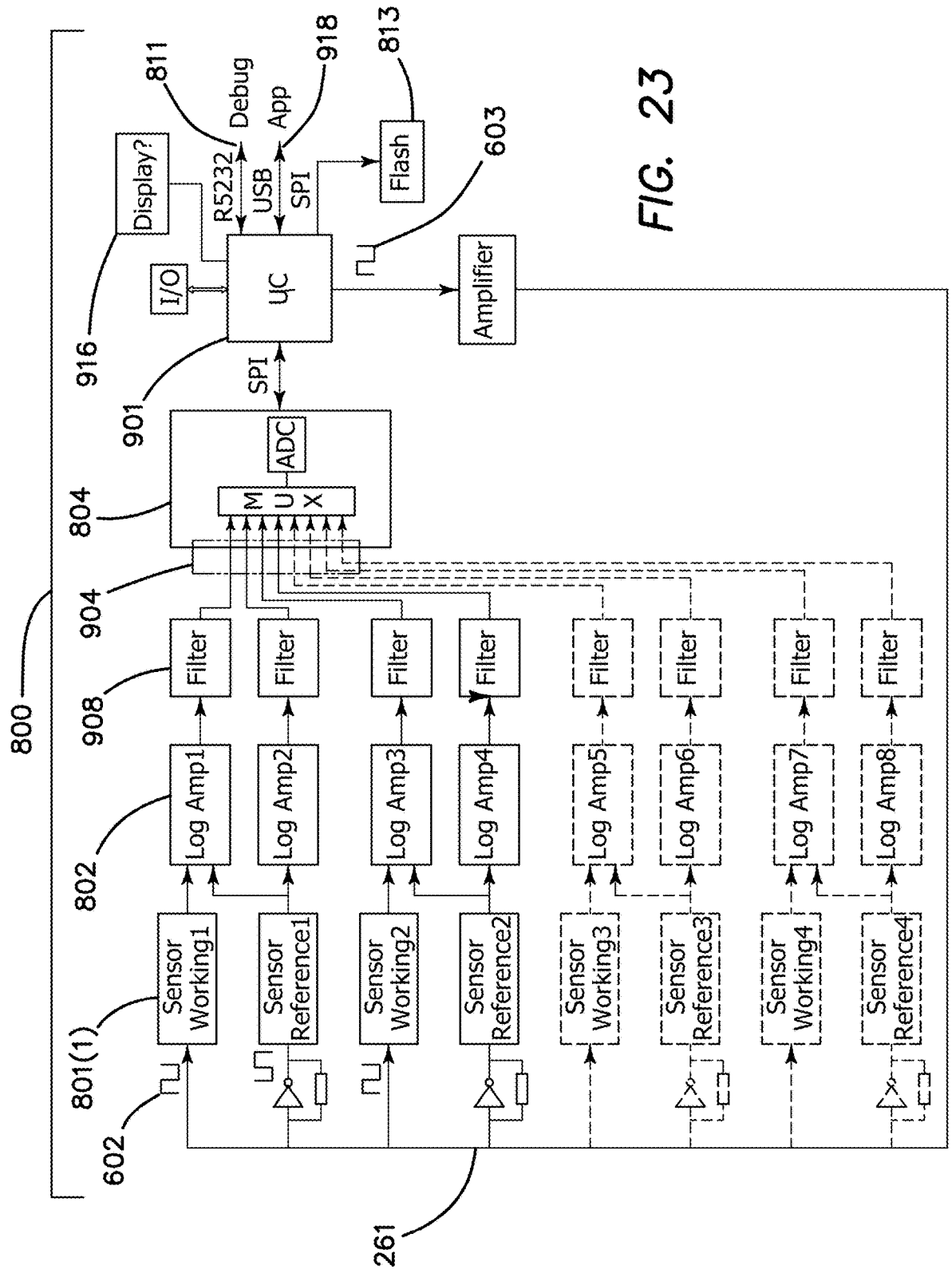
FIG. 23 is one example of a schematic representation of an analog front end (AFE) with selectively connectivity to the analog processing platform.

The circuit architecture shown in FIG. 23 includes the analog front end 904 coupled between the sensor array 261 of a plurality of sensor and reference cell pairs 34(n), each pair coupled to a corresponding log amp 802 and filter 908 and through multiplexer 804 to the digital back end including microprocessor 901. The output signal from filter 908 is a continuous analog signal. The apparatus mimics the underlying biological processes employing discrete state spaces; this data is then manipulated by the arithmetical modules (AU) 300 which mathematically describe the physical process operating on time-varying quantities. The analog computational unit 300 and the digital peripherals shown in FIG. 23, record, store and analyze the hybridization as well as the diffusion processes, which underlay the biology investigated by the apparatus 900.

Figure 23A:
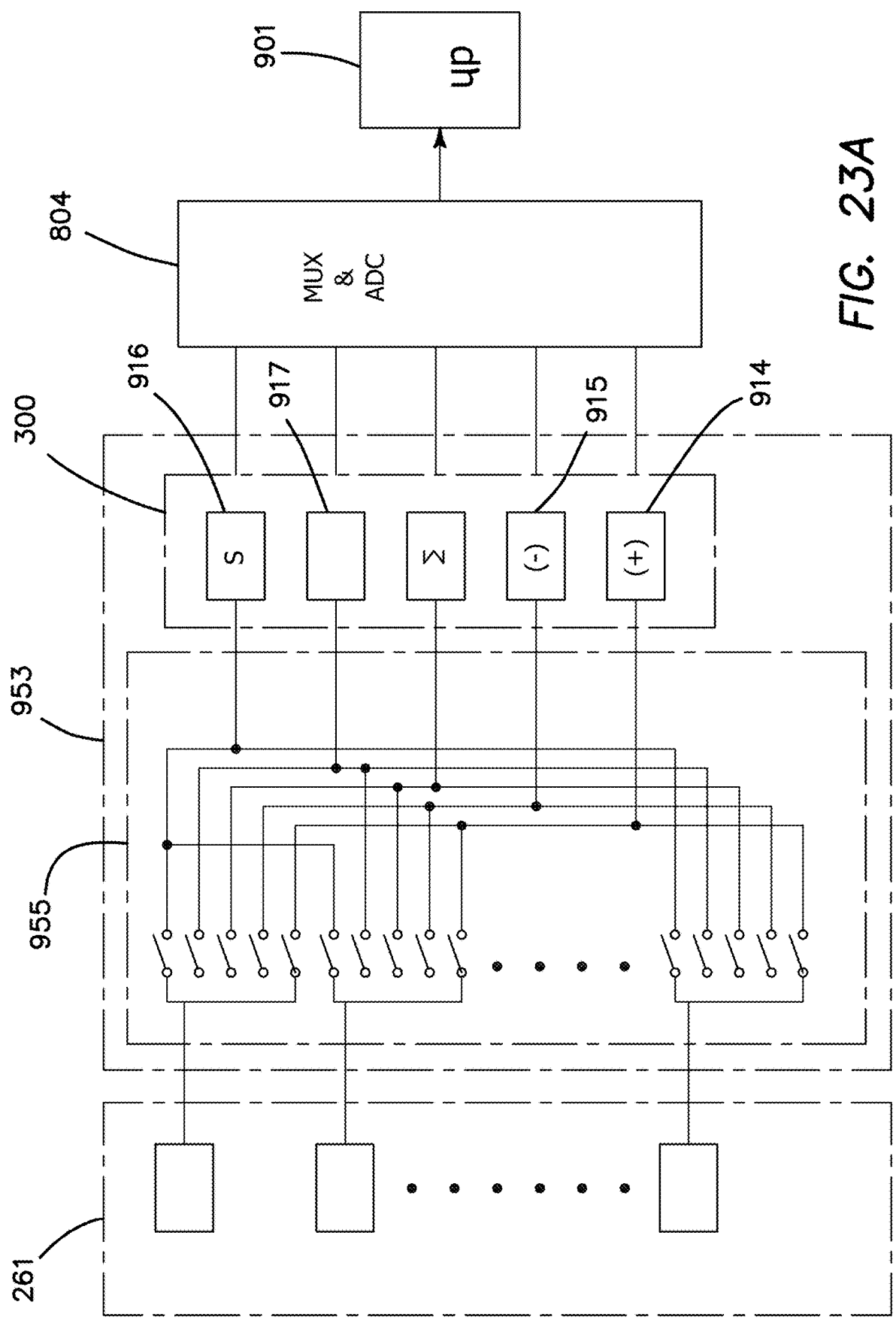
FIG. 23A is schematic representation of an addressable multiplexer (universal switch) module coupled to the output of an array of biosensors and thence to an analog arithmetic module before being multiplexed and digitized into a microcontroller.

FIG. 23A is a schematic block diagram describing the interconnection between the sensor array signal outputs from filters 908 into a universal analog multiplexer 955 including in analog front end 904 in FIG. 23. The multiplexer 955 further enables the selection of the arithmetical operator 914, 915, 916, 917 forming the AU 300. On command from microcontroller 901 the multiplexer 955 enables the command to select the desired arithmetical operation within AU 300.

Figure 23B:
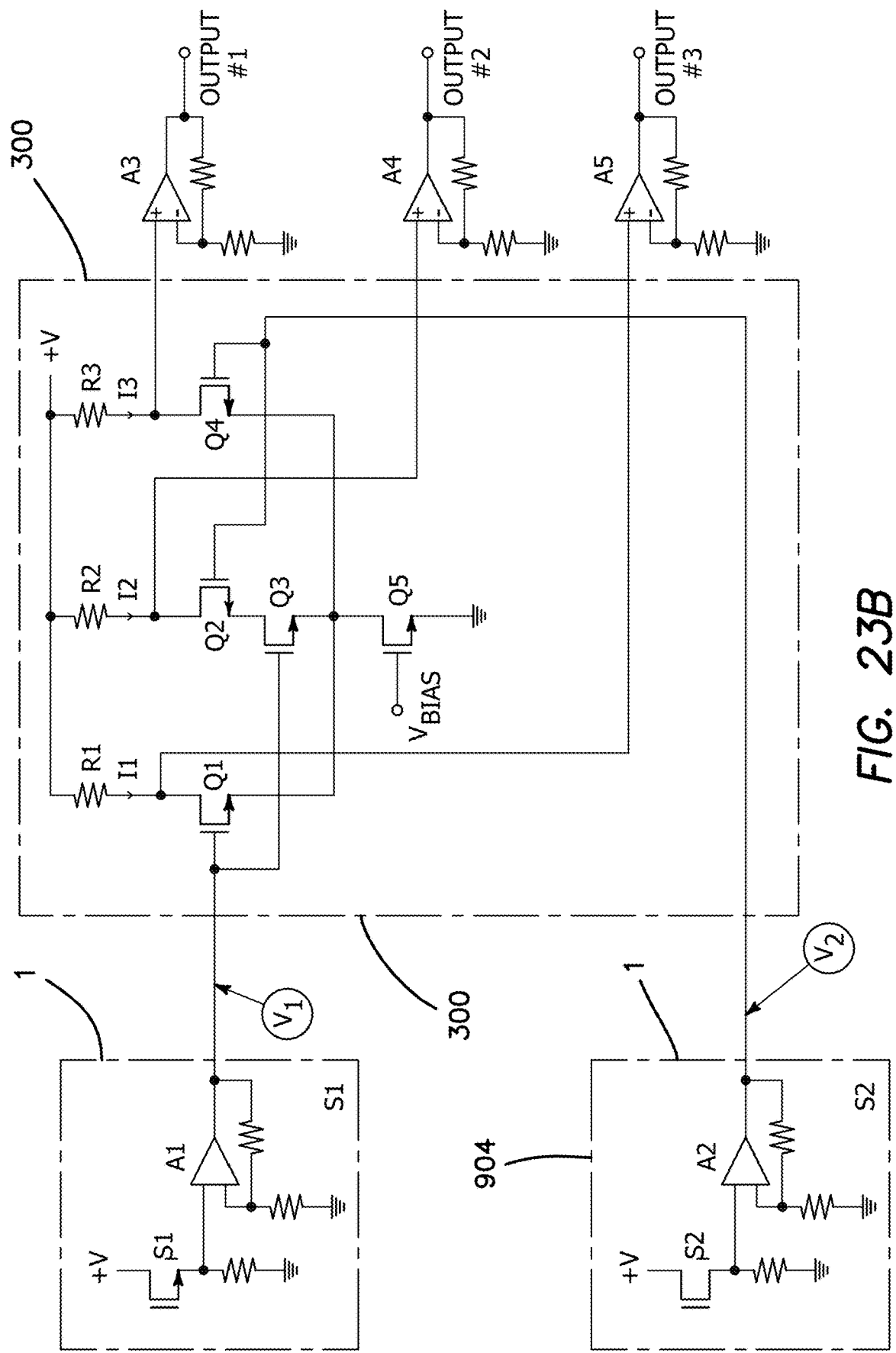
FIG. 23B is one example of a schematic diagram of the SAW sensors $S_1$ and $S_2$ connected to the analog arithmetic module (AU), generating an operation on data generated by the SAW sensor (tanh) and the derivative of the same function (d/dt of tanh).

FIG. 23B is a schematic representation of one of optional configurations of connectivity of SAW 1 (sensor S1 and S2) with the analog arithmetical module (AU) 300. The circuitry is an exemplary demonstration of the multiple configurations by which the SAW sensor unit 1 can be interfaced with the AU 300. In one embodiment, two SAW sensors 34 are used and are connected to the AU 300 as two inputs. In addition, the AU 300 circuit is fitted with variable gain in the form of the extra FET transistor Q5, where the control transistor bias Q5 changes the gain of the section.

The circuit of FIG. 23B is an illustration of the use of the arithmetical analog calculator in use with the SAW sensor comprising of two SAW sensors are shown as S1 and S2. Both are connected to a voltage amplifier, A1 and A2 respectively. The sensor(s) outputs two voltages, which are proportional to the chemical/biological activity (the hybridization rate of analyte/antibody). These are shown as V1 and V2. These two signals are taken to the inputs of the arithmetical module 300, configured by four FET transistors and are marked as Q1, Q2, Q3 and Q4. The FET Q5 serves as a bias transistor. The four transistors together compute (in this exemplary case) the tanh (hyperbolic tangent) function of the difference between the two input signals, V1 and V2. In addition, the AU 300 also computes the derivative of the same function (d/dt of tanh). A simple difference between the two signals is also present. The (AU) 904 outputs are represented as currents, marked as I1, I2 and I3. These currents are proportional to the functions described above. It is necessary to convert these current signals to voltages, hence the addition of the three resistors, R1, R2 and R3. An additional stage of amplification is added to each of the signals after conversion to voltage; indicated as A3, A4 and A5. While considering the energy used in the detection as well as the resulted arithmetical operation, the circuit in FIG. 23B exhibited the substantial saving while performing such operation. The energy budget is in the range of a few femto-amps and it is much more efficient then a digital mathematical computation circuit, when performing similar operation.

In the illustrated embodiment, however, the analog computation unit 300 may provide familiar operations that use differential equations. These include basic arithmetic operations in FIG. 22A-22D, such as algebraic sum 914 and difference 915 ($u(t)=v(t)\pm w(t)$), constant multiplication or scaling ($u(t)=cv(t)$), variable multiplication and division ($u(t)=v(t)w(t)$, $u(t)=v(t)/w(t)$), and inversion ($u(t)=-v(t)$). Transcendental functions may be provided, such as the exponential ($u(t)=\exp v(t)$), logarithm($u(t)=\ln v(t)$), trigonometric functions ($u(t)=\sin v(t)$, etc.), and further option is the use of a re-solvers for converting between polar and rectangular coordinates. In addition, the arithmetical unit 300 perform a definite integration 916 ($u(t)=v_0+\int_{t_0} v(\tau)d\tau$), but differentiation may also be provided 917 ($u(t)=v(t)$).

A reaction-diffusion computation is an important example of continuous-time analog computing within the framework of the apparatus 900, which could be computed in AU 300. In one example, the state of the system apparatus 900 with the analyte is represented by a set of time-varying chemical concentration fields, $c_1, \ldots, c_n$. These fields are distributed across a one-, two-, or three-dimensional space $\Omega$, so that, for $x \in \Omega$, $c_k(x, t)$ represents the concentration of analyte (k) at location x and time t. Computation proceeds in continuous time according to reaction-diffusion equations, which have the form: $\partial c/\partial t = D\nabla 2c + F(c)$, where $c=(c_1, \ldots, c_n)^T$ is the vector of concentrations, $D=\text{diag}(d_1, \ldots, d_n)$ is a diagonal matrix of positive diffusion rates, and F is nonlinear vector function that describes how the chemical reactions affect the concentrations.

There are many variations as well as configurations of interfacing the arithmetical unit with the SAW sensor array 261 and the analog-front-end 904, in one preferred embodiment the analog arithmetic unit 300 and the analog front end 904, function as one integral signal path, to maintain the continuous nature of the signal fidelity, mimicking the underlying cellular biological process in which hybridization and its diffusion coefficient, including its native time constant as well as its impedance value as measured in array 261 are preserved, prior to any digital filtering or smoothing (curve fitting algorithm) the resulting analog signal with its amplified gain and its arithmetical manipulation, is one of the essential embodiments of the proposed apparatus.

If the simple input and feedback impedances are replaced with complex networks, either passive or active, the amplifier circuit will develop more complicated transfer functions than those shown. In addition to the basic amplifiers, the general purpose analog computational unit contains a variety of special purpose units; for example, multipliers to form the product of two or more variables, fixed and variable-diode function generators to perform various nonlinear operations on the variables, switches to start and modify the operations, and comparators to make elementary decisions based on the value of a particular variable. It is the compatibility and simplicity of interconnection of these various components that give the analog computation its flexibility and versatility. An analog computer interface (ACI) is useful in a variety of applications although a digital electronic computer is used in the back-end to process the data. The analog interface is well suited for the solving differential equations (PDE), specifically non-linear differential equations and systems of equations required in mimicking the biological processes. The analog computation unit is comprised of circuits that can perform addition 914, subtraction 915, multiplication, division, integration 916, and differentiation 917, which enable the proposed apparatus 900 to reliably mimic the stochastic-statistical nature of the underlying electrochemical processes which ultimately provide a realistic ground for the biological sequences investigations, as well as the ability to capture and mimic biological processes.

In one of the preferred embodiments of this application, the apparatus and its method solve specific mathematical operations needed in resolving the diffusion equation as well as hybridization of the antibody-analyte conjugate. The mimicking of such biological processes is performed by connecting SAW cells 1 with analog circuits to record continuous biological processes, in which the hybridization sequencing order in cellular process is replicated in apparatus 900, by employing a suitable memory bank. The data recorded and or analyzed by the resident microcontroller 901 and its associated memory bank can be used as part of the underlying information necessary to understand stochastic hybridization of such biological processes, hence provide a window to the resulting vectorial trends which ultimately contribute to the resulting protein product at the end of the chain in the mimicked cellular process. Inputs to the circuit are voltages, which usually vary with time in a prescribed manner, and measurement of the output voltage yields the equation's solution as a continuous representation of the effective capacitive loading and its inverse impedance equivalent value.

The method and apparatus proposed by the invention enable the measurement of such process by its ability to capture and analyze the data in the time domain as well as its frequency domain, hence providing for a realistic representation of the underlying biology and its equivalent circuit.

In one embodiment the layout of the circuit and the SAW cell's position are configured in a manner, which enables a measurement of sequence and timing of the hybridization process. Such data of sequencing and time further enable statistical mapping of biological processes.

In other embodiments, data sampling can also be time delayed to allow for sequence processing in the temporal domain. The definition of a system is a collection of independent, interacting entities forming an integrated whole, whose behavior is distinct and qualitatively greater than its parts. Although data samples are specific to individual cells, global patterns in the data can emerge through application of a diffusion algorithm to the data residing in microcontroller 901. In this sense, the analog front interface with its digital processor enables multiple parallel systems of hybridization to be traced, due to their dynamics, and data patterns are derived from the correlation or relationship of data sequences between the different SAW cell's units in the array 261 by using different antibodies located in different SAW cell units.

An example for such use is the flow of an analyte sample containing multiple biomarkers (antibodies) 28 and where different SAW sensors 1 measure and record the hybridizations of two or more of such biomarkers antigens 29 simultaneously. A typical diagnostic procedure which enables the correlation of such, is noted by measuring the presence and densities of multiple biomarker and their respective values such as $VEGF_{165}$, c-erB-2 AND p53 from a patient's sample by obtaining the density matrices of the three biomarkers in one continues dataset, by the use of apparatus 900. The simultaneous hybridization of multiple biomarkers is here analyzed as a phase space of multidimensional vectors to enable the resultant data to lead to a statistical correlation of possible causal connection between multiple biomarkers such as $VEGF_{165}$, c-ERBb-2 and p53. A density matrix for a biomarker is thus a matrix that describes a system where different parameters are available at the same time, such as impedance, time and geometrical location of the cell, which enables a recordation of the physical density, location and type of antibody/antigen. This is to be contrasted with a single state vector that describes an assay where multiple analytes are measured. The density matrix is the analogue to probability measure (probability distribution of position and time of hybridization). The classical parameterization of phase space statistics can be used as a tool to represent the hybridization of multiple biomarker simultaneously to enable the resultant data to lead to a statistical correlation of possible causal connection between multiple biomarkers such as: $VEGF_{165}$, c-erB-2 AND p53 as clinically an augmentation of the three biomarkers with a positive vectorial change is statistically significant in determining the presence of e.g. breath cancer.

A density matrix is a matrix that describes a system in a state where different parameters are available at the same time, a measure of several elements within that state (time and geometrical location) within a state enable a recordation of density, location and type of antibody/antigen This should be contrasted with a single state vector that describes an assay where multiple analytes are measured The density matrix is the analogue to probability mea sure (probability distribution of position and time stamps of hybridization) and it is assumed as the measure of phase space in classical statistical mechanics.

To emulate and represent a biological sequencing by state-by-state hybridization an analog computing device of the kind described by the application is needed to enable direct solution of polynomial differential equations (PDEs). In general a PDE solver depends on an analogous physical process, that is, on a process obeying the same class of PDEs that it is intended to solve. For example, in Mills, J. W. (2008). "The nature of the extended analog computer." Physica D: Nonlinear Phenomena 237 (9) (Elsevier). pp. 1235-1256, and following Lee A. Rubel, describe use of analog circuit in mimicking the diffusion of electrons in conductive sheets or solids to solve the diffusion equations. In mimicking "reaction-diffusion" biology, a continuous-time analog computing is a necessary step in preserving the fidelity of the process. The state is represented by a set of time-varying chemical concentration fields, c1 ... cn. These fields are distributed across a one-, two-, or three-dimensional space $\Omega$, so that, for x $\Omega$, ck(x, t) which represents the concentration of analyte k at location x and time t. Computation proceeds continuously in time according to reaction-diffusion equations, which have the form: $\partial c/\partial t = D\ 2c + F(c)$, where c=(c1 ... cn)T is the vector of concentrations, D=diag(d1, ... , dn) is a diagonal matrix of positive diffusion rates, and F is nonlinear vector function that describes how the chemical reactions affect the concentrations. The use of the analog module (AU) 904 enable such procedure and realization of the Lee A. Ruble's architecture in addressing the effective solution of PDE and their accuracy (precision), by preserving the actual and realistic underlying biology in a continues form and without the customary digital discrete and filtered data reduction.

A careful review of the embodiments of the invention, demonstrate the ability of the cellular array of SAW 1 sensors to capture, measure, count and analyze the entire biological process of molecular conjugation, in an analog continuous and reliable fashion to enable the tasks of mimicking computational biology in a novel, effective and were results are consistent with scientific standards.

The SAW Cell

Figure 2:
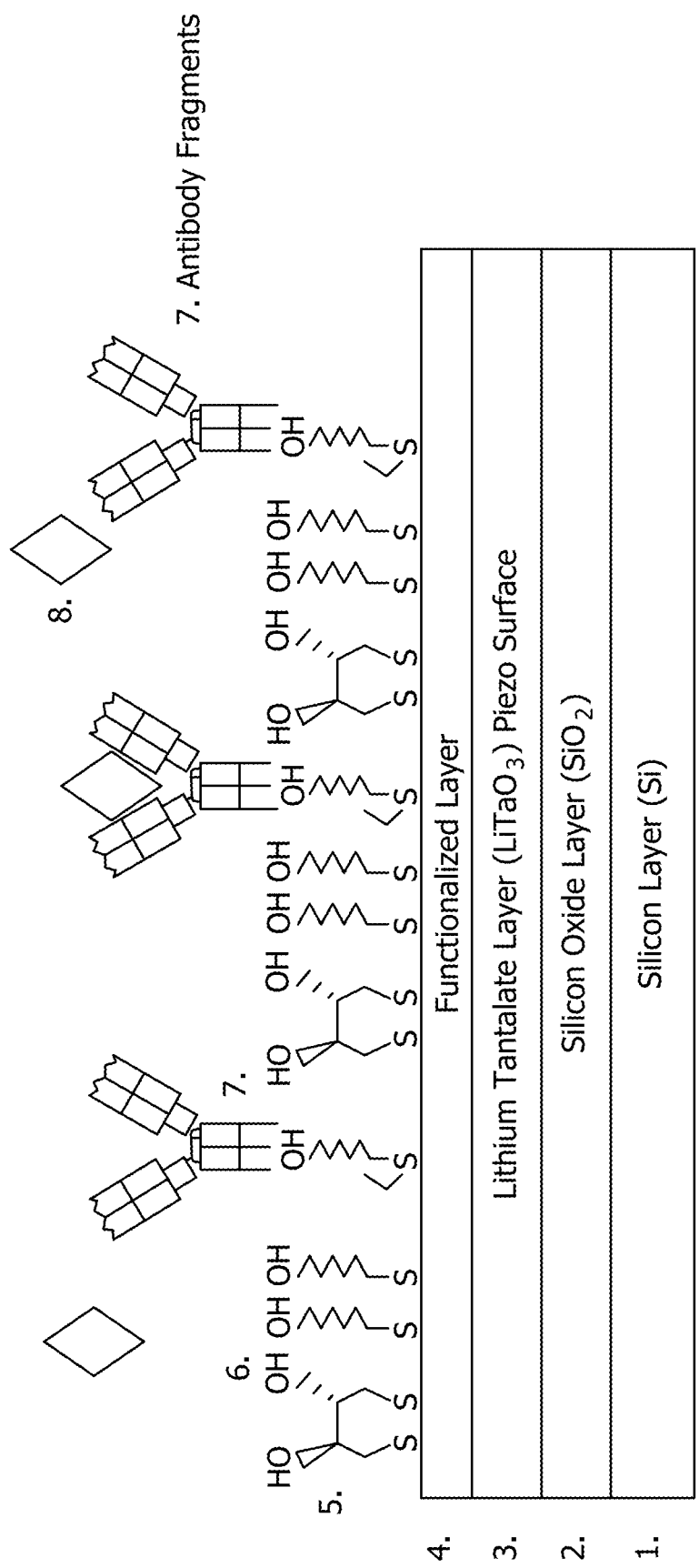
FIG. 2 is an orthographic representation of the functionalization of SAW with Silicon layer (Si), Silicon Oxide layer (SiO2), LiTaO$_3$ (piezo) layer, Functionalized layer, Linker molecule, Spacer molecule, Antibody Fragments, Analyte protein
Figure 2A:
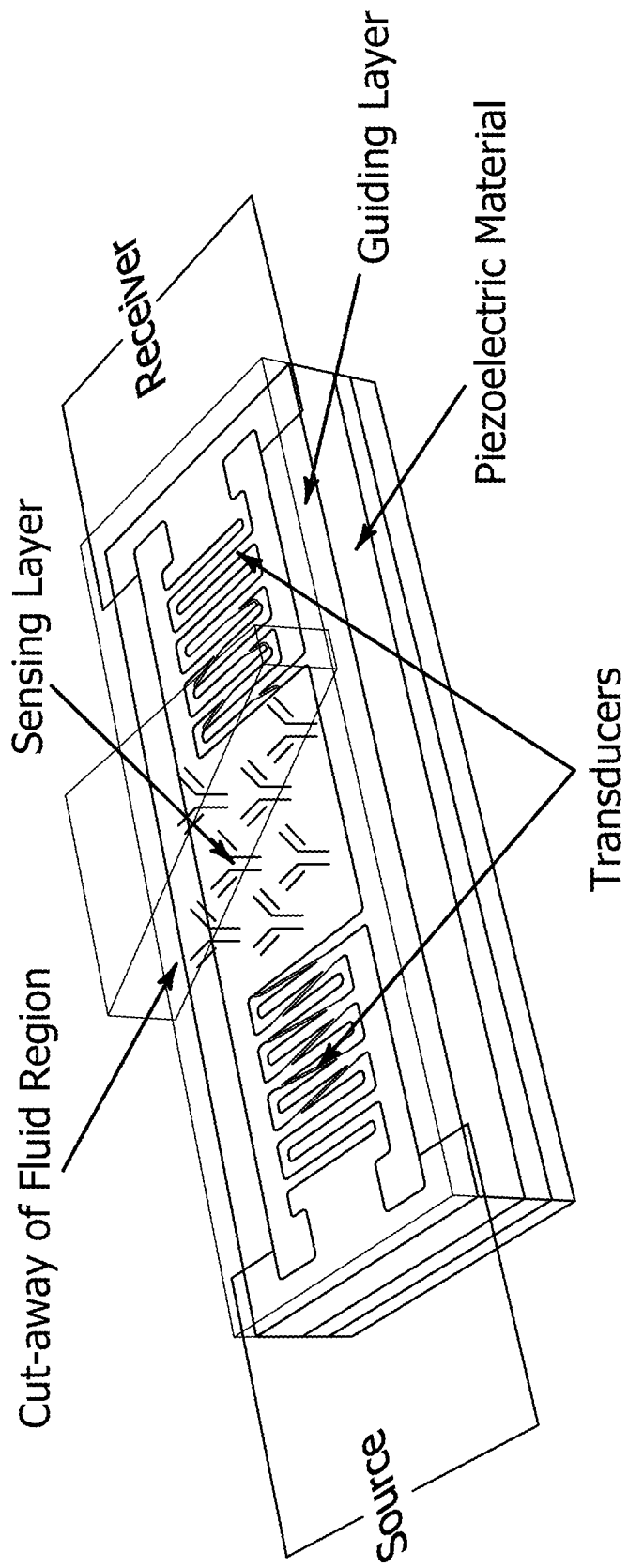
FIG. 2A is a side cross sectional view of a diagram of the SAW sensor fabrication using conventional lithographic or screen printing methodologies with notes on functionalization of SH SAW sensing lane.
Figure 2B:
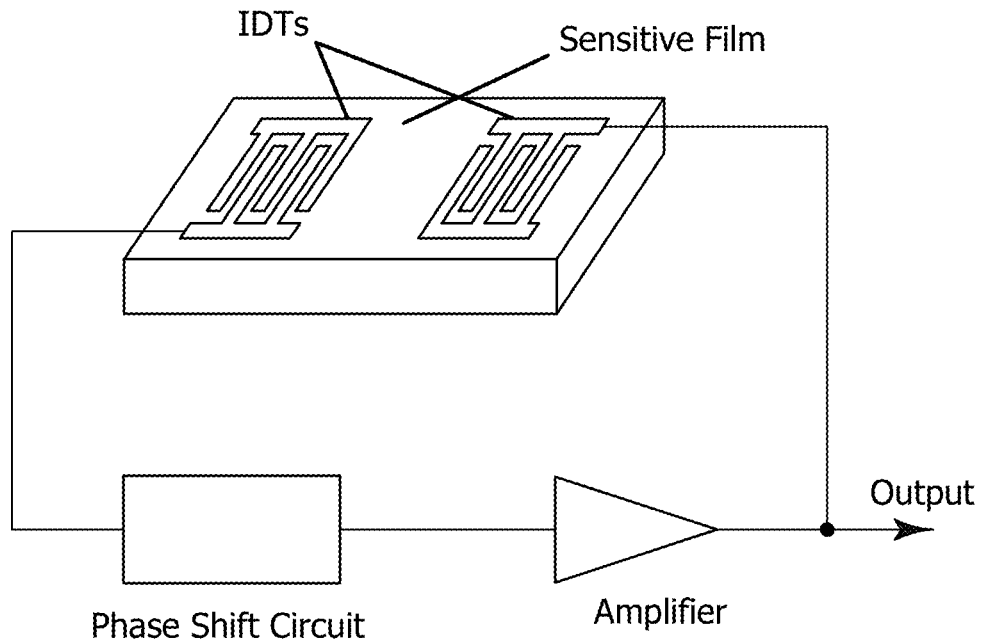
FIG. 2B is a schematic representation with its functional block comprising of phase shift circuit and amplifier.
Figure 2C:
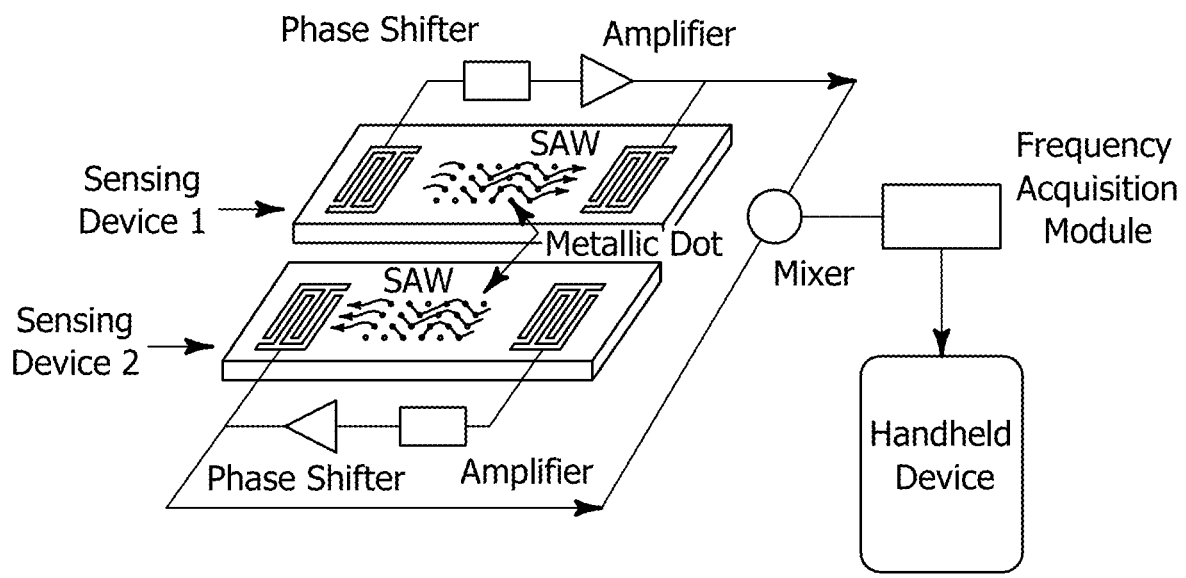
FIG. 2C is a schematic representation of a dual SAW sensor configured with a common RF source and a common processing unit.

FIGS. 2 and 2A are a diagrammatic cross sectional view of the SAW cell 1 fabricated by conventional photolithography. A silicon (550 μm) wafer is used as a substrate 76. A nonconductive layer 70, such as $SiO_2$, is disposed on substrate 76 and used to isolate the Si substrate 76 from $LiTaO_3$ crystal with the geometrical layout of 36° Y-cut X-axis propagation 60. The interdigitated IDT input 66 and IDT output 68 forming the oscillator wave characteristic cell 34 are each produced using a simple technique for the fabrication of interdigitated electrode (IDEs) employing conventional lithography. A top-down simple lithography approach is used to fabricate a set of Interdigitated electrodes were patterned with aluminum metal. Silicon dioxide serves to isolate the electrode from the substrate.

The guiding layer 62 of the proposed SH SAW biosensor 1 follow the study and guidelines set by S. E. Miller, "Integrated Optics: An Introduction" The Bell System Technical Journal, Vol. 48(7) pp. 2059-2069 (1969). A typical waveguide used in integrated acoustic is a strip waveguide, typically a thin and narrow region having somewhat higher refractive indices than the surrounding medium, with typical transverse dimensions of one to several wavelengths of the radiation. This last requirement translates into typical transverse dimensions of integrated acoustic strip waveguides of one to several micrometers. Such guiding structures are generally defined and produced by lithographic techniques akin to those used in integrated circuit technology.

Electrical and Flow Dynamic Factors of the SAW Design

Figure 5:
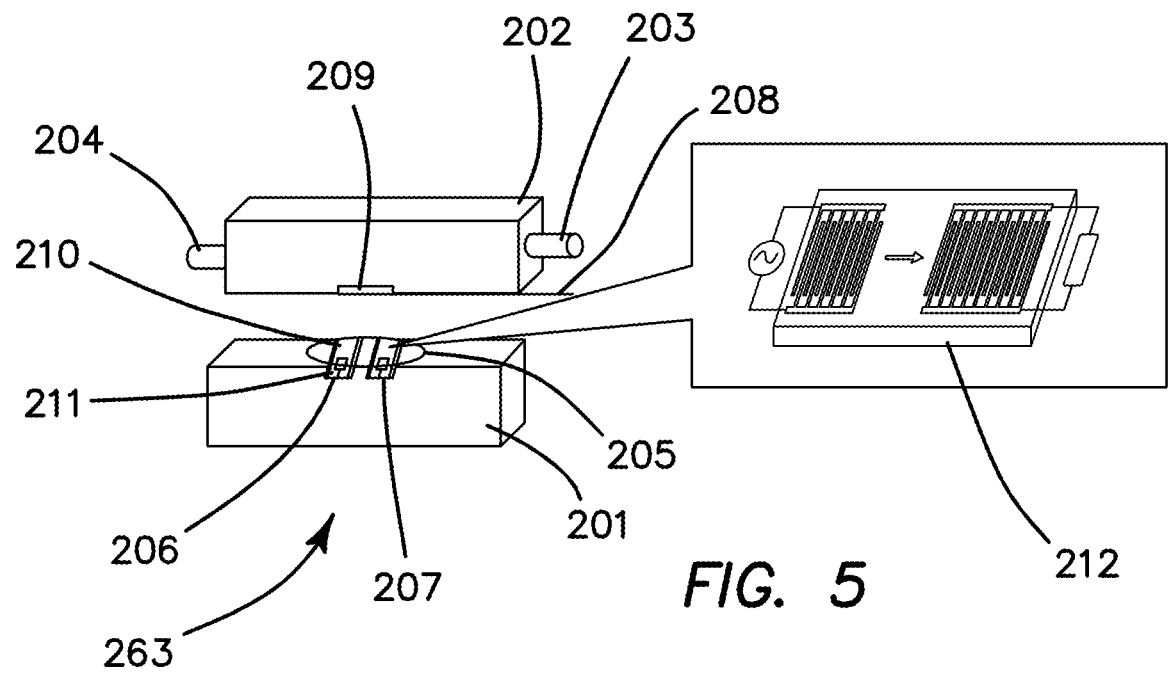
FIG. 5 is a diagram of a fluid flow cell including a sensor cell and corresponding reference cell pair.

Multiple geometrical layouts are available to realize the SAW cell architecture and to accommodate the two fundamental principles guiding the metrics of the cell 34, namely the flow characteristics of the buffer and analyte. Specifically, the molecular size of the item desired to be measured such as $VEGF_{-165}$ molecule ranges between 35-50 kDa, while *E. coli* bacteria and larger proteins measure between 200,000 kDa to 500,000 kDa. The SAW cell 34 is tested and evaluated in terms of LOD performance parameters. Families of phase-shift response associated with concentration of the analyte as shown in FIG. 3 curves reveal essential device characteristics (DC) related to the performance of SAW cell 34 acting as analytical device-biosensor. These parameters include transconductance, threshold voltage, on/off ratio, mobility, etc. Biological receptors such as antibodies 40 (also called capture probes or ligands) specific to target biomarkers 42 are physically bound to the surface of the sensing lane 66 via a single step linking process 38. When the antibodies 40 capture target biomarkers 42, the binding event will cause a change in the frequency or amplitude and such change is reflected by the apparatus as a differential output of phase shift 48. The amount of signal 284 in FIG. 5 generated is inversely proportional to the concentration of biomarkers in the sample for a narrow range of concentrations, called the dynamic range 285 (FIG. 5). The curve represents the logarithmic output of the SAW in operation. SAW devices usually have a narrow response range. The typical "S" shape (reverse) of a response curve 282 is illustrated in FIG. 5, where the signal intensity is plotted as a function of the biomarker capturing time. At low analyte concentrations, still below the detection limit, the sensor 1 can only display baseline signal 280. Once the threshold concentration is reached (limit of detection, LOD) the sensor 1 will produce response signals linearly proportional to the concentration of the analyte which has bound (if plotted in logarithmic scale). This linear response typically spans one or two orders of magnitude of analyte concentrations. As the analyte concentration continues to increase, the sensor surface will be saturated, and the lower limit of response is reached 283. At the lower level, further increase in, for example, VEGF concentration as analyte, the plot indicates saturation and generates a constant response as the capacitive load reaches its maximum coverage threshold within the geometry of the SAW effective area.

There are many factors that influence the dynamic range 285 of biosensors, including the binding affinity of antibodies, sensor geometry, number of active receptors on the surface, sensitivity of the transducer, etc. The SAW sensor dynamic range is tuned to its specific application by optimizing the device geometry, as defined by the effective flow geometry as well as the distance between reference lane and the sensing lane(s) surface.

Arrays of SAW Cells

Figure 4:
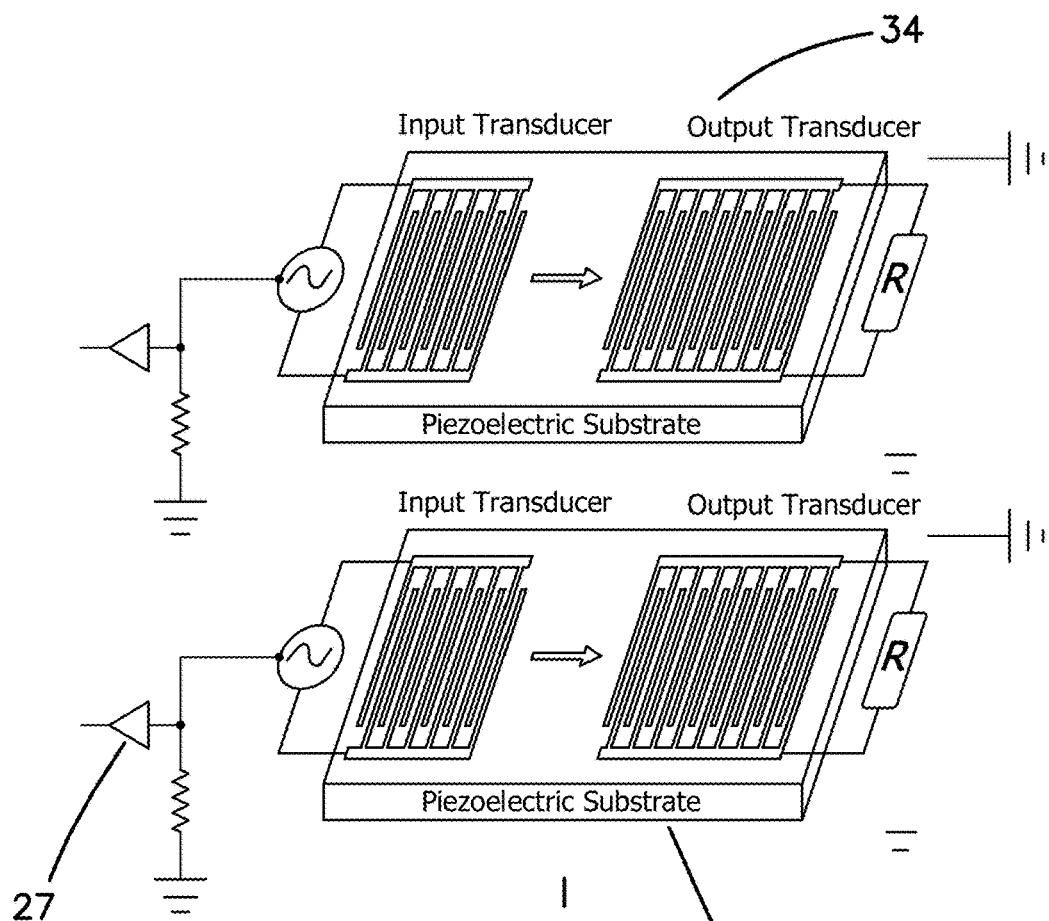
FIG. 4 is a diagrammatic schematic of the array configuration of SAW cell units each configured with a source follower amplifier.
Figure 4:
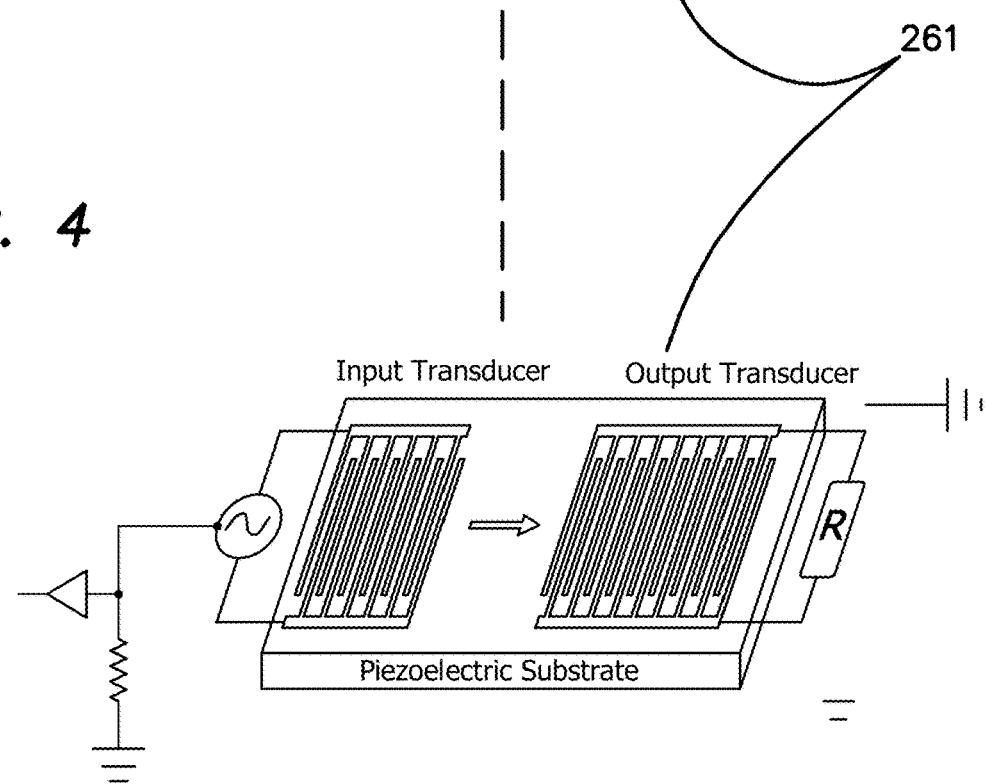

FIG. 4 is a schematic of a plurality of cells such as shown in FIG. 4 and their corresponding source follower amplifiers 27 are arranged into an array 261. The array configuration and its geometrical layout is a function of its use, the cells in an array can be arranged in an arbitrary number of dimensions and geometrical configurations, such as a square, triangle, hexagonal, or any other spatially arrangement. Topologically, the SAW cells 34 can be arranged on an infinite plane or on a toroidal space, and the microfluidic chambers may assume a variety of hydodynamical topologies to improve fluid flow and obstruction avoidance due to sedimentation of proteins on chambers.

Figure 4A:
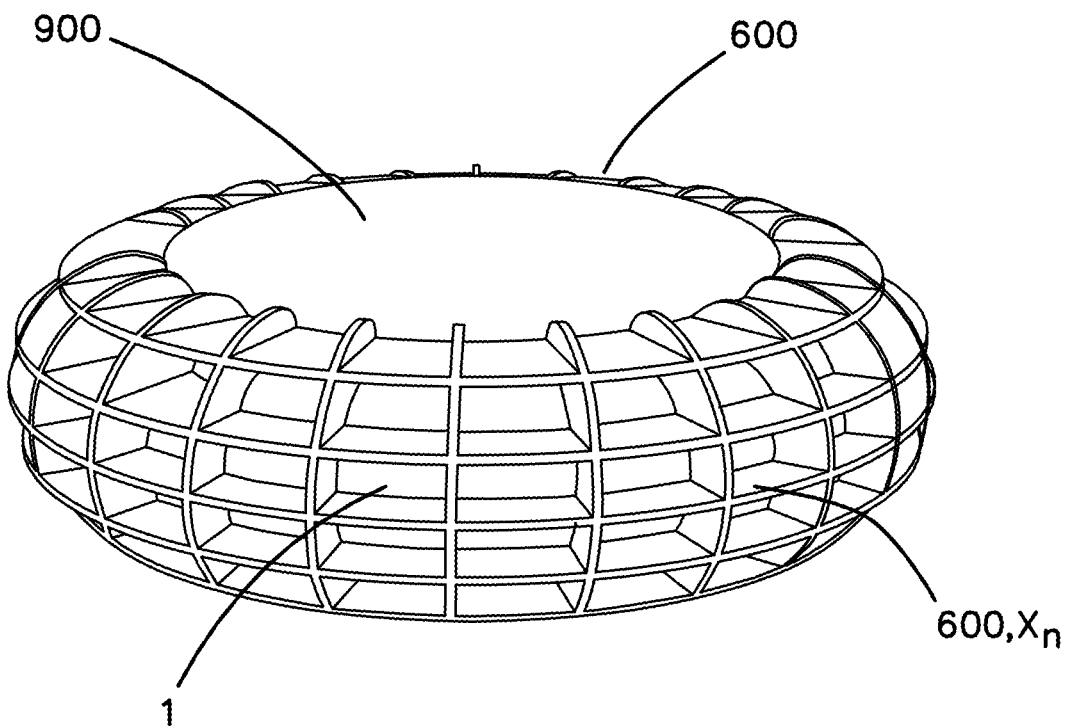
FIG. 4A is a perspective view of a scaffold for an array of cells in the form of a torus.

FIG. 4A is a geometrical representation an array of the SAW cells 1 configured in a toroidal shape 600 and arranged in indexed and addressable cells of the microfluidic chamber $600.x_1, 600.x_2 \ldots 600.x_n$. The geometry proposed is similar to a doughnut but rather than having an empty central "hole", the topology of a torus folds in upon itself and all points along its surface converge together into a zero-dimensional point at the center called the Vertex. This makes it the perfect environment within which to populate the SAW cell 34 and where the analyte flows through a toroidal manifold 600, which mimics the essence of an uninterrupted flow of the biological payloads of buffer and its constituents. Any input placed at the Vertex while the torus is "torsioned" (folded and rotated inward) is spread out and distributed over the entire surface of the toroid. This embodiment of flow characteristics provides for an improved use of the volumetric mass of the analyte; hence increases surface area exposure between the analyte and its antibodies, and increases the diffusion coefficient and hybridization rate.

FIG. 21 is a schematic representation of an array 600 of microfluidic chambers 139 and geometrical layout 600 of the SAW array. There are many variations of geometry associated with such device and where the considerations that define the boundary conditions for such design are subject to the intended use and flow-rate considerations of the devices. Since the SAW sensor array 261 and its apparatus 900 is intended for detection of antibody, an antigen, a protein, a receptor, an aptamer, a peptide, a DNA strand, or an enzyme, the metric designated as variable dimension (L) of array 600 and flow characteristics may vary depending on the sampled assay employed by the use of the apparatus 900. The principle parameters are the type of fluid used, the dimensions of the fluid channels and the fluid's velocity in these channels. The relationship between these parameters can be expressed as the Reynolds number (Re), $$\left[ Re = \frac{\text{inertial forces}}{\text{viscous forces}} = \frac{\rho v L}{\mu} = \frac{v L}{v} \right],$$

which is a dimensionless quantity useful for determining the dominant profile in a flow system. Parameters such as density of fluid $\rho$, the mean fluid velocity V, the hydraulic diameter of the channel and fluid's viscosity $\mu$ are general parameters for the microfluidic chambers. Typical parameter values for microfluidic chamber in an aqueous fluid are given to enable flow in a laminar fashion. FIG. 21 shows a network of micro-channels 611 included in the microfluidic chip (SAW 1) connected to the outlet port 615 by input port 614 pierced through the chip. An optional geometry layout is shown in FIG. 4A where the number of cells 1 as well as their layout is subject to the intended use of the apparatus 900 in combination with the target analyte, such as the detection of an antibody, an antigen, a protein, a receptor, an aptamer, a peptide, a DNA strand, or an enzyme.

Charging and Discharging the Cell Array

In one of the embodiments, defined by FIG. 21 the details of the charging and discharging circuits 602 are shown. The circuit is set to measure the RC time constant, (i), where the time constant (in seconds) of an RC circuit, is equal to the product of the circuit resistance (in ohms) and the circuit capacitance (in farads), i.e. $\tau = R*C$, which is the time required to charge the capacitor (dimensionally shown in FIG. 1A of the SAW 1), through the resistive load, by ≈63.2 percent of the difference between the initial value and final value or discharge the capacitor to ≈36.8 percent. This value is derived from the mathematical constant $(1-e^{-t/\tau})$ more specifically as voltage to charge the capacitor versus time, where the charging of the capacitive load is represented as $V(t)=V_0 (1-e^{-t/\tau})$, while the discharge obeys the function $V(t)=V_0 (1-e^{-t/\tau})$. The array is subject to a cycling of charging and discharging as discussed above. Circuit 602 has as its input a square wave 603 into an operational amplifier buffer 607, and includes a current to voltage amplifier 607, feedback resistor 605, an Op-amp integration circuit 608, with an input resistor 609, and a feedback capacitor 604. SAW cell 34 has the equivalent circuit noted by FIG. 19B, which demonstrates a circuit consisting of two double-layered capacitors (CDL) 221 connected in series with a resistor of medium solution (the buffer, RSol) 222, which, in turn, is connected in parallel with a dielectric capacitor (CCell) 223. The lead resistance (RLead) 224 is the sum of the series resistances of the connecting wires. The impedance signal output 225 is the same as the input square wave 603. The half period of the input square wave 603 should be significantly larger than the RC constant formed by resistor 222, and capacitor 221 of SAW 34, so that Op amp 607 has enough time to discharge the sharp transitions caused by the square wave 603. As the capacitance change due to hybridization between the analyte and the probe capture, the SAW sensor electronics reflect a change in amplitude of the output signal proportional to the mass accumulating on the sensing lane. The impedimetric change due to capacitive loading is measured simultaneously by the phase detector 97 to account for the relative differential output of the sensing 206 and reference lane 207.

In one of the preferred embodiments, the microfluidic chamber 139 and its SAW array is defined in a two-dimensional Euclidean space, like a grid. In one example, the chambers are organized as a parallel array 261 in a defined geometry. However, it is possible to arrange the cells into a three-dimensional space such as noted in FIG. 4A. However, the cells in an array can be defined in an arbitrary number of dimensions and geometrical configurations, such as square, triangle, hexagonal, or any other spatially arrangement. Topologically, the SAW cells 34 can be arranged on an infinite plane or on a toroidal space and the microfluidic chambers may assume varieties of hydro-dynamical topologies to improve fluid flow and obstruction-avoidance due to sedimentation of proteins on chambers walls. In other embodiments of this application the SAW cell 34 is interconnected with series or parallel interconnections suitable for measuring hybridization of e.g. antibody, an antigen, a protein, a receptor, an aptamer, a peptide, a DNA strand, or an enzyme.

Sensor and Reference SAW Cell Pairs

FIG. 5 is a diagram of the microfluidic chamber assembly 263 divided into a bottom section 201 of the fluid flow cell and the top section 202. The top section 202 acts as the cover to the microfluidic channel incorporating the waveguide 209, IDT output 68, the distance between the gate electrode 18 and the internal chamber active surface 14 is defined as the effective sensor geometry providing the unit measure of capacitive/impedance per unit of surface area of the SAW cell 34. The microfluidic chamber is fabricated from a polymer employing a three dimensional printer. It can also be fabricated on glass, ceramics and metal using etching, deposition and bonding, polydimethylsiloxane (PDMS) processing, thick-film and stereo lithography as well as fast replication methods via electroplating, injection molding and embossing. FIGS. 33a and 33b diagrammatically depicts a PDMS replica molding process using PDMS processing. As shown in FIG. 25a photoresist 78 is spin coated onto a silicon or glass substrate 76. The resist 78 is baked and a mask 80 is selectively disposed onto resist 78, which is, then exposed portions are UV cured, and removed to define microfluidic channels 82 therein to provide a master pattern 84. A PDMS replica mold is made by the steps illustrated in FIG. 25b wherein rods 86 are disposed on the master pattern 84 and a thick layer 88 of PDMS polymer resin poured over the master pattern 84 to the level of rods 86. The PDMS layer 88 is thermally cured and released from the master pattern 84 to result in the finished PDMS replica mold 88.

The microfluidic chamber contains the following features, which enable the flow of analyte and buffer in an aqueous form through the surface fluid channel inlet 203 and the fluid channel outlet 204, which passes through the device active area 210, which is sealed by an O-ring 205. Within the sealed chamber is the active area 210 set in the bottom section 201 containing the SAW sensing lane 206 and neutral reference SAW sensor cell 207, which provides output signal through the IDT output 211. Each sensor and reference cell 206 and 207 respectively, has the architecture shown in the schematic insert 212 or the cell 33 of FIG. 4. Sensor cell 206 and reference cell 207 are identical or substantially identical in all circuit, geometric, chemical and material parameters, except that sensor cell 206 has been functionalized with an active antibody 52 layer and reference cell 207 has been functionalized with a non-specific antibody 59 such as IgG, IgA, IgM, IgE and IgD. The output of the sensor and reference cells 206 and 207 respectively can be differenced in the circuitry of FIG. 6 to obtain an output indicative of only the specific bioeffect of the functionalized SAW or sensor cell 206.

Figure 6:
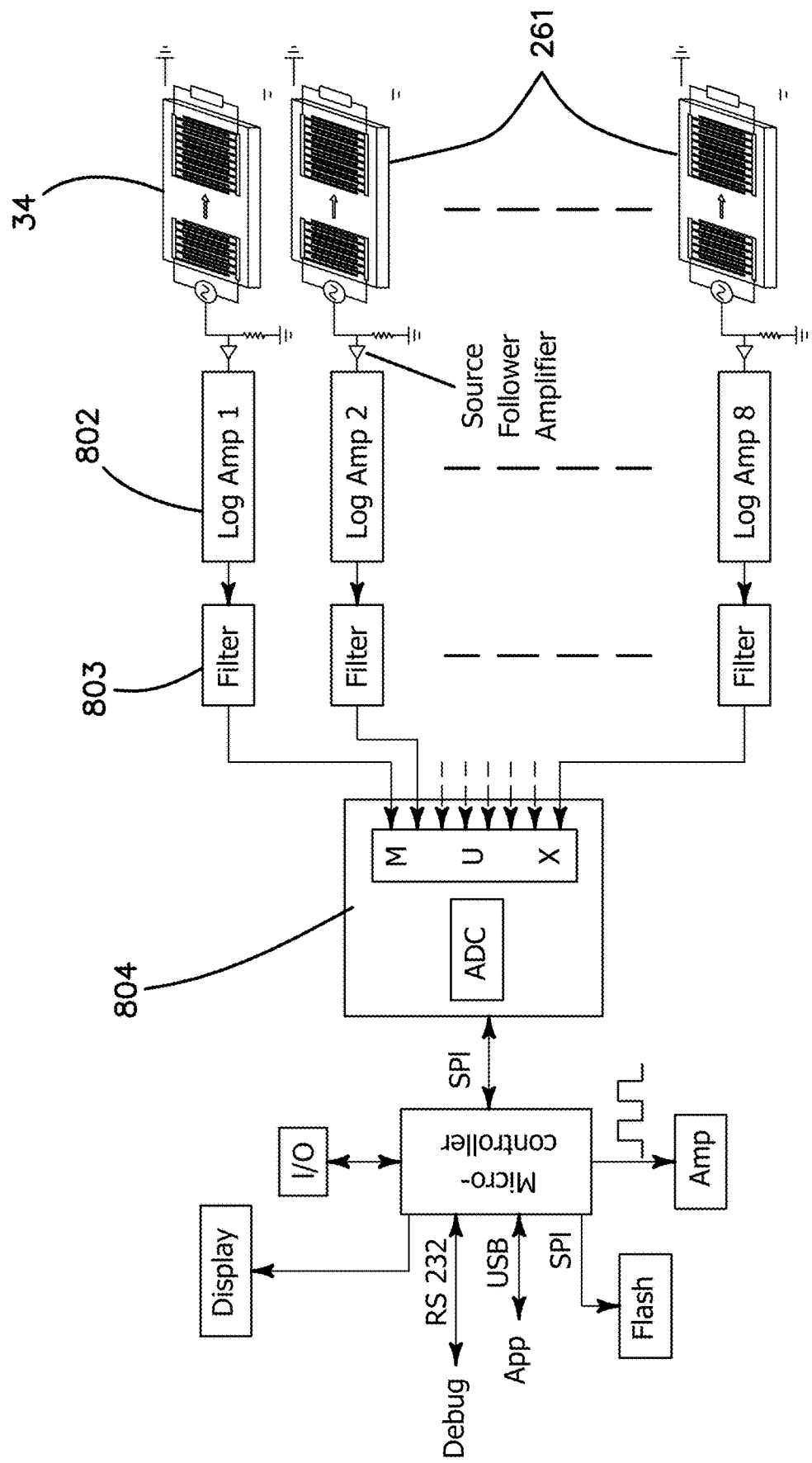
FIG. 6 is a block diagram of a pathfinder/reader describing the analog front end coupled to the array of cells that are multiplexed and digitized into its microcontroller.
Figure 7:
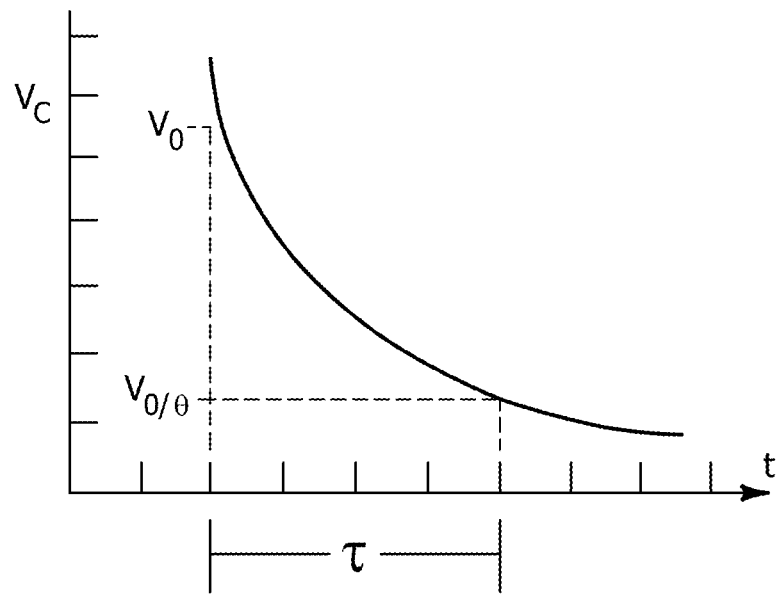
FIGS. 7 and 7A are graphs of an exponential decay of the RC network representing a typical hybridization of analyte with its antibody, where a circuit switches its output "off" and "on" as shown in FIG. 7A and where a saturation detection circuit measures the time constant as shown in FIG. 7.
Figure 7A:
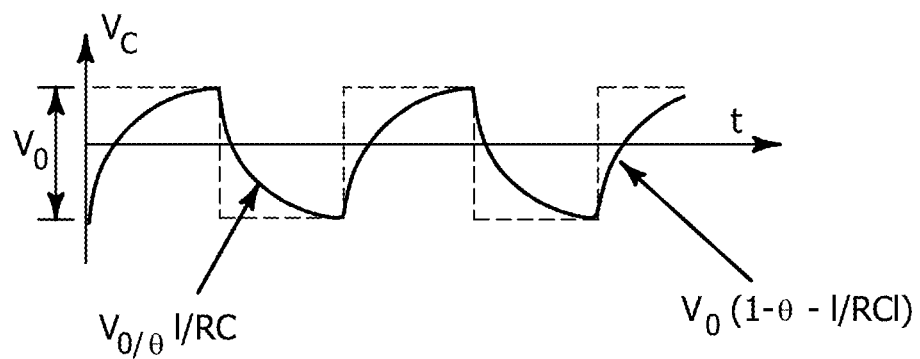

A plurality of cell pairs 206, 207 of the type shown in FIG. 5 in an array form similar to FIGS. 7 and 7A in a circuit architecture schematically depicted in FIG. 6, are each combined with analog interface 802 and digital processing unit 804 of apparatus 800, also called the pathfinder reader. The source follower amplifier 27 of each cell 34 (also referenced as cells 206 or 207) is coupled to a corresponding log amplifier 802. The use of logarithmic analog computational method is employed by the proposed circuit to widen the dynamic range of input operation of the SAW 1. Logarithmic transduction affords advantages such as constant-precision sensing at any intensity (Weber's law) and is a requirement in designing circuit 900 which operates with a sweep frequency of 50 Hz to 100 kHz, and where such use is explored in one of its embodiments where the sweep frequency is capable of going to lower than 50 Hz with impedance range of 50Ω to 10 MΩ (resistance value lower than 100Ω, and up to 10 MΩ are available as optional mode). If the concentration of a hybridization factor is fixed, and as the analyte conjugation increases in value, it is eventually binds all the available antibodies molecules and saturates the number of bound antibody/analyte complexes available. In addition, if the number of binding sites for a complex is limited (due to the finite cells of SAW 1 and its array 261 with their effective binding sites), these sites will eventually all be bound by complexes or optionally with a gene expression that saturates. These two sources of saturation limit the dynamic range of hybridization and recording available in apparatus 800. FIG. 6 shows a circuit approach that simultaneously alleviates both these saturation problems to widen the dynamic range. The log amplifier 802 has an output voltage $V_{out}$ is K times the natural log of the input voltage $V_{in}$, expressed as, $V_{out}=K_{In}Vin+V_{ref}$, where $V_{ref}$ is the normalization constant in volts and K is the scale factor. A filter 803 is then coupled to the output of each log amplifier 802 for the purpose of noise filtration. A multiplexer 804 multiplexes the analog outputs of the plurality of filtered log amplifiers and digitizes the analog signals in an included analog-to-digital converter. The data is then coupled to a computer 806 with a plurality of conventional input/output peripherals for data processing and display.

Performance Characteristics of Cells

In other embodiments, the SAW cell array 261 and apparatus 800 measure the "effective sensor geometry" which in this application, is the ability of the apparatus and proposed method to measure the physical landscape of the local hybridization (the equivalent captured area by the hybridization of the antibody with its analyte) to map or capture such biological activity relative to the spatial and temporal terms, (differentiating such data relative to time domain), while recording capacitive values, amplitude change and phase shift, by mapping such changes relative to spatiotemporal data reduction collected by the apparatus arithmetic logic unit 300 in FIG. 23 where multiplexer 804 enables the biosensor 1 to be processed by a selection of the mathematical operation(s) shown by example FIGS. 30A-30D. These electrical impedance values with their respective time stamps of saturation events enable tracking of biological sequences occurring on the SAW 1.

The change in capacitive loading on the SAW 1 and its impedance is directly related to its effective geometry, which is a term of art, identifying the surface or volume of the SAW 1 available to capture analyte in a process of hybridization and its equivalent electrical change. These and other embodiments of the invention relate to scaling of the geometry of the SAW array, relative to flow characteristics as well as obstruction of protein by sedimentation in the microfluidic chamber. The effective cross sectional area of the flow through the SAW cell 1 must be larger than the cross sectional area of the flow inlet and outlet so that the physical geometry of the sensor does not impede the flow characteristics of the entire system. The capacitance due to the sensor geometry is described in Equation (i) using the dielectric ($\varepsilon_r$) as a variable which correlates with target analyte 42 concentration in the test sample.

$$C_{geometry}=\varepsilon_r\varepsilon_0\frac{A}{D} \quad (i)$$

Where A is the sensing area 14 between the input and output IDTs, D is the distance 18 between the IDTs represented as the equivalent of capacitive plates, and $\varepsilon_r$ is the combined relative permittivity (dielectric constant) of the medium measured by the apparatus 800, consisting of the VEGF sample 43, a pH buffer 28, specific antibody 52 to capture a target analyte molecule 42, (such as Pegaptanib sodium, Macugen; mfg. by Eyetech/Pfizer) Amino hybridization substance, $SiO_2$ insulator, and p-Si substrate; $\varepsilon_0$ is the permittivity of the free space ($\varepsilon_0=8.8541878176\times10^{-12}$ F/m); A is the total area of electrode plates located between the input 66 and output 68 IDTs (shown in FIG. 2B) with width, and length shown for example on FIG. 2E, and where D is effective geometry term, indicating the open space available for the biological conjugation of antibody, an antigen, a protein, a receptor, an aptamer, a peptide, a DNA strand, or an enzyme to occur between input and output IDTs. The values of A and D are chosen so that the electrical change in capacitance/impedance, phase shift or amplitude, due to hybridization, is effectively measured with the limitations associated with the circulation flow of the analyte through the SAW sensor unit.

An exemplary expansion of the geometry of the SAW array 261 is realized by reducing the geometrical terms to its metrics. Considering the fact that the thickness of the surface of VEGF165 bound to its antibody is approx. 200 nm, the separation between the IDT fingers can be as small as a few micrometers without the risk of restricting the flow due to VEGF molecule-hybridization and sedimentation of residual nonspecific proteins. However, because the cross sectional area formed by $d_{cap}$, and $W_{cap}$, it must account for the molecular dimension in molecular weight value. Hence, the effective geometry cross sectional area of the corresponding flow inlet 203 and outlet 204 in FIG. 21 must follow the Reynolds (Re) fluid flow characteristics through the SAW-chamber during the measured event, otherwise sedimentations bound to cause flow's obstruction.

Using an example for possible layout of the SAW sensor array 261 within a microfluidic chamber 139, and given the dimension of 3 French (0.039 of an inch) inlet diameters 614, the aggregate minimum cross sectional area of fluid flow through the entire parallel array 261 of biosensors 1 is approximately 100 mm×8000 mm. The only free variable in Equation (i) is the combined dielectric constant $\varepsilon_r$ that is the changes with VEGF molecule hybridization and the surface antibody chemical chain. In order to maximize the effective sensing area in a small volume, the SAW 1 spacing between the IDT input 66 and IDT output 68 (see FIG. 1E) and arranged in e.g. interdigitated fingers pattern, to yield the desired results.

Using the example described above, a method for calculating the LOD minimum threshold for generating an electrical signal (phase shift) is subject to the minimum capacitive change (in microfarad) within the effective surface area of the SAW cell plate 64. Assuming a surface area of 102.02 µm, with d (the distance between the IDT input 66, and IDT output 68, and the effective sensing area 64 is 100 µm, so it follows the total space required for each IDT pair. Because the plate area of 1 cm² provides sufficient capacitance of around 10 pF, A is chosen as 1 cm² and $W_{cap}$ (the width of the plates which is the distance between IDT input 66 and IDT output 68 on one side and the waveguide 62 (structured as top of the SAW cover), shown in FIGS. 1A and 1B, chosen as 0.8 cm, this exemplary geometry results in a total length of plates of 12500 µm. With $L_{cap}$ (the length of the plates) chosen as 625 µm, and where there are 20 SAW cell pairs arranged in interdigitated finger pattern, Thus, the total internal volume of the array module is 8000 µm (D)×725 µm (H)×4040.4 µm (L). With the dimensions noted above the applicant, performed a study to confirm the process and validate the working assumptions used by the proposed application.

The measurement technique employed in computing the total output of the electrochemical cell, as noted by FIGS. 1 and 1A, is simply the SAW 1 change of dielectric value associated the hybridization of the analyte/antibody and where $\varepsilon_r$ is the combined relative permittivity and dielectric of the medium relative to the sweep frequency $\varepsilon_r(\omega)$ attenuating the capacitive load/impedance while changing the device characteristics (DC) of SAW output ($Vds-I_{ds}$).

In one embodiment, the invention teaches of an analog front end circuit 904 (shown in FIG. 21) which enables charging and discharging of the "effective space" between the IDT input 66 and the IDT output 68, to enhance polarity's kinetics between the analyte the electrochemical SAW cell, at the appropriate frequency, and measure its equivalent capacitance from the average current in half-period, as is noted in Equation (ii), $$I_{avg} = \frac{\Delta Q}{T/2} = \frac{C\Delta V}{T/2} = 2C\Delta Vf \qquad (ii)$$

Where ΔV and f, are known and $I_{avg}$ can be measured. This measurement technique is illustrated in circuit 602 in FIG. 21, which consists of two separate circuits. The op amp source follower 27, which increases the input impedance of the electrochemical SAW cell 34 so that the cell can be driven by a near perfect square wave by a digital output signal line from a microcontroller 901. The frequency (f) of the square wave 603 is chosen as the maximum frequency that completely charges and discharges the capacitor in the electrochemical SAW cell in the half period. The charging of the capacitor creates a charge field, which allows the binding of the desired molecule and the discharging of the capacitor to free the molecules, which bind due to ionic or electrical polarity. This allows the device 1 to bind and unbind nonspecific ionic molecules so that there is not a permanent build up or binding of nonspecific proteins due to ionic members within the buffer solution 28. The second part of square wave 603, converts $I_{avg}$, into voltage value with a known resistor value of resistor 605 and amplified with a pre Op-Amp 607. $V_1$ at the output of the Op Amp 607 is calculated as shown in Equation (iii).

$$V_1 = C_{cell} R_1 \frac{DV_{in}}{dt} \qquad (iii)$$

An op amp integration circuit as a source follower arrangement converts the transient voltage values 606, into a square wave 603, as shown in Equation (iv).

$$V_{out} = -\frac{1}{C_2} \int \frac{V_1}{R_2} dt \qquad (iv)$$

Substituting Equation (ii) into (iii), the output of circuit 602, as a function of its input can be calculated as shown in Equation (v) leading to Equation (vi).

$$V_{out} = \frac{1}{C_2 R_2} \int C_{cell} R_1 \frac{dV_{in}}{dt} dt \qquad (v)$$

$$V_{out} = \frac{C_{cell} R_1}{C_2 R_2} V_{in} \qquad (vi)$$

The output voltage of circuit 602 sampled by an ADC 804, (shown in FIG. 6) is proportional to the value of $C_{cell}$. The multiplication of this principle as it is applied to a matrix of SAW cells 261 in an array format and its selected optimal geometry terms, is provided to achieve the desired results of parallel detection and computing apparatus 300 suitable for the specificity of the measurement, or for mimicking of such dynamics, using multiple parallel geometrical arrangements as contemplated by the invention and its embodiments.

Proof of Concept Performance

Figure 8:
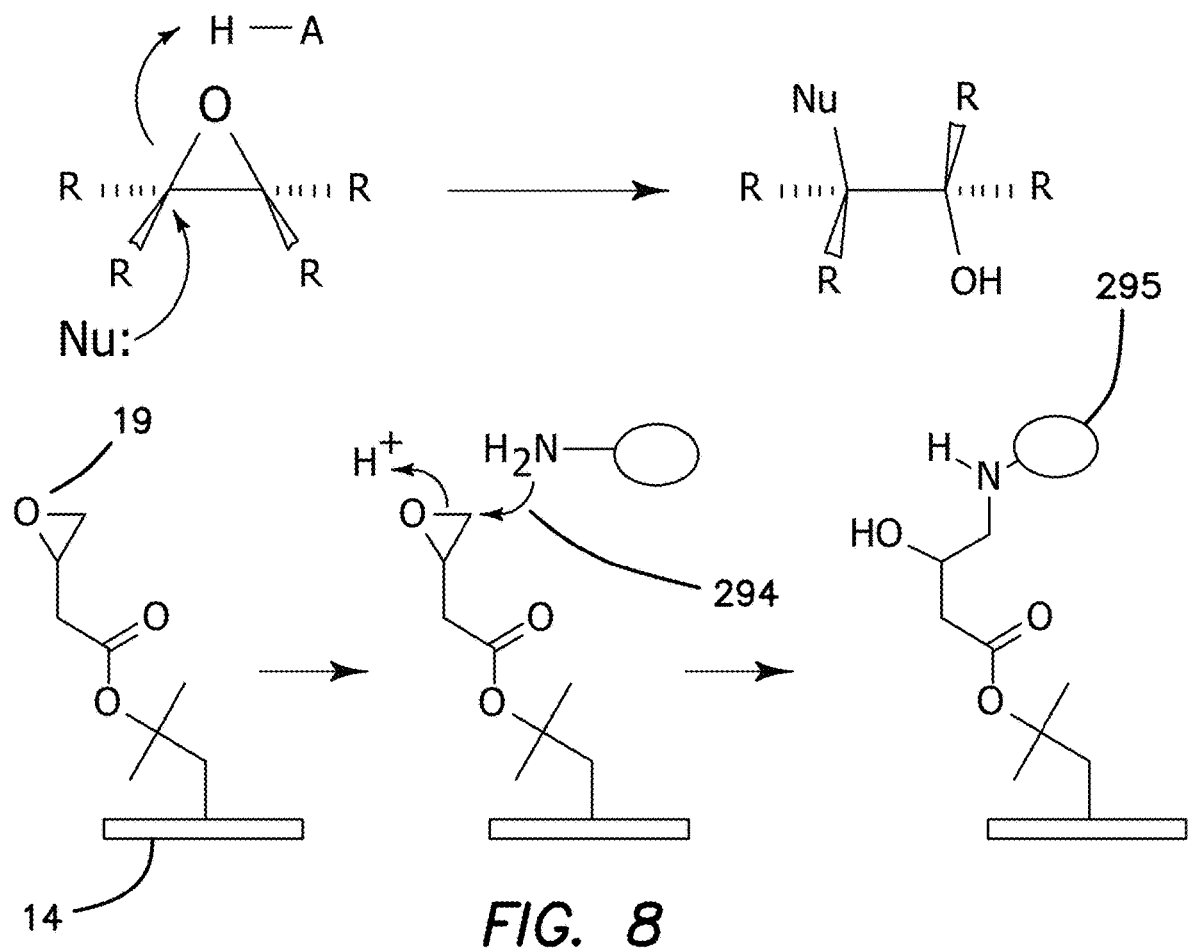
FIG. 8 is a molecular diagram of the functionalization of the active surface using epoxide nucleophilic substitution chemistry.

FIG. 8 is a molecular diagram of the functionalization of active surface 14 using epoxide nucleophilic substitution chemistry. The description provided below is an example of the chemical bonding of the sensing area 206 and its functionalized group while forming the SAW effective geometry, resulting in the attenuation of the SAW to generate the desired signal while hybridizing the analyte with its specific antigen. An antibody 295 or amino-modified aptamer can be covalently linked to the poly (glycidyl methacrylate) (PGMA) 19 coated active surface 14 through a nucleophilic substitution reaction. The nucleophiles on the antibody (e.g. lysine residues and the amine-terminus) will attack the electrophilic carbon of the c-o bond, forcing the ring opening of the highly strained epoxide group 294. The nucleophilic ring opening of the epoxide by amines results in the formation of a β-amino alcohol group on the PGMA polymer, with the antibody or amino-aptamer 295 covalently attached to the PGMA 19. This nucleophilic substitution reaction between the epoxide groups on the PGMA and nucleophiles on the antibody allows for any antibodies and amino-modified aptamers to be covalently linked to the active surface 14.

Molecular Modeling of Binding

Figure 9:
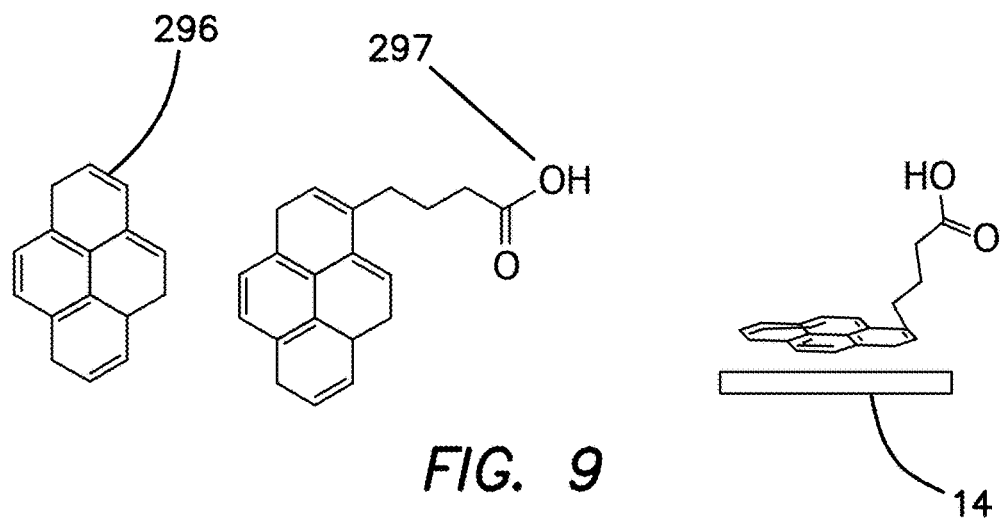
FIG. 9 is a molecular diagram of the process of functionalization of the active surface using pyrene through π-π interactions.

FIG. 9 is molecular diagram of an alternate process of functionalization of the active surface 14 using pyrene through π-π interactions. Non-covalent functionalization of the active surface 14 can be achieved using pyrene 296 and pyrene derivatives 297. The aromatic groups on the pyrene and pyrene derivatives are bound to the surface of the active surface 14 through non-covalent π-π interactions. The strong π-π interactions between the aromatic pyrene is a combination of electrostatic and van der Waals interactions. The geometry of interactions is determined by the electrostatic effects, while the van der Waals interactions contribute to the magnitude of the π-π interactions.

Figure 10:
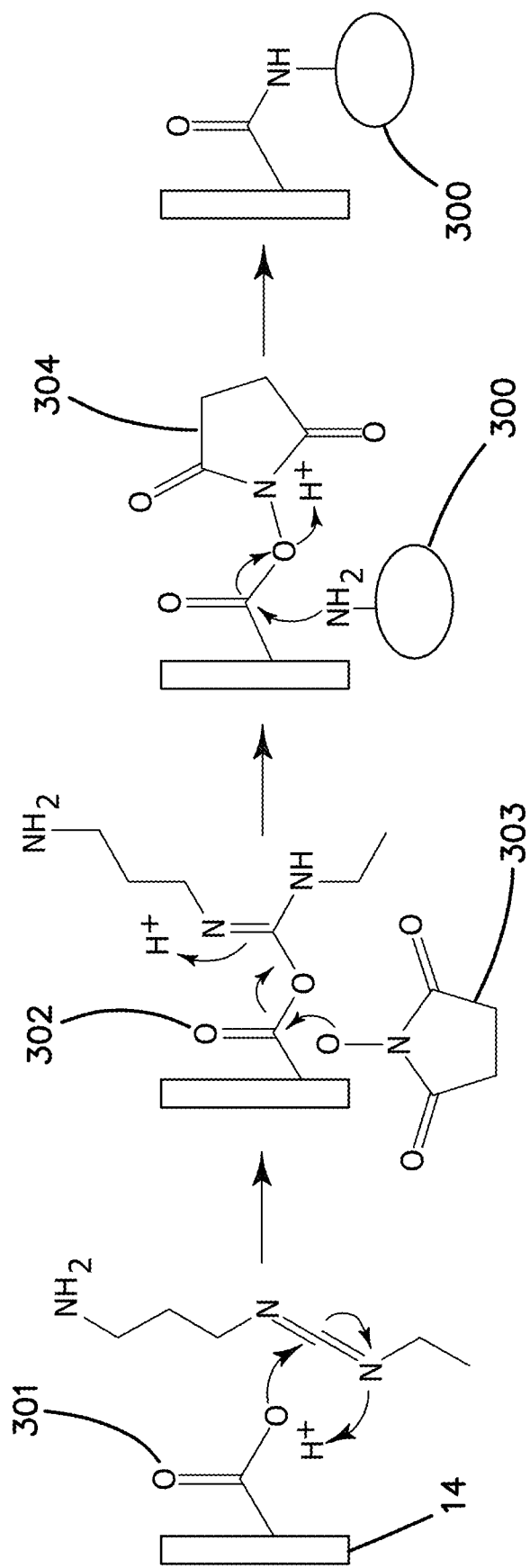
FIG. 10 is a molecular diagram of the covalent immobilization of antibodies to carboxyl groups through amide linkage.

FIG. 10 is a molecular diagram of the covalent immobilization of antibodies 40 to carboxyl groups through amide linkage. Surface carboxyls on the active surface 14 or the carboxyls on the pyrene 301, is activated using 1-ethyl-3-(3-dimethylaminopropyl) carbodiimide (EDC) 302 for direct conjugation with primary amines via amide bond linkage. The EDC-activated carboxylic acid forms an active O-acylisourea ester intermediate that can be displaced through nucleophilic substitution from the amines. To prevent rapid hydrolysis of the O-acylisourea ester intermediate, N-hydroxysuccinimide (NHS) 304 is added to the reaction, forming an amine-reactive NHS-ester that has improved the stability. The antibody 40 will be linked to the carboxyls through covalent amide linkage by displacing the NHS. This EDC/NHS immobilization process allow for any antibody or protein to be immobilized on the active surface 14 through the covalent amide linkage between the amines on the antibody and carboxylic acid groups on the pyrene or on the active surface.

FIGS. 17A and 17B are molecular diagrams of the interaction between the aptamer 295 and single-strand oligonucleotides. FIG. 11A shows the interaction between the aptamer 295 and single-strand oligonucleotides and FIG. 11B shows a schematic of how aptamer 295 binds antigen 307. Aptamers are single stranded oligonucleotides (DNA or RNA) selected against a target molecule using systemic evolution of ligands by exponential enrichment (SELEX). Aptamers provide several advantages over antibodies including improved stability and site-specific modification of the aptamers to allow conjugation of a reporter molecule (dye) or a functional linker for immobilization, long selflife, and storage temperature, i.e., can be stored at room temperature for several months. The unique sequences of the oligonucleotides allow each aptamer to fold and adopt specific secondary and tertiary structure. The affinity and avidity an aptamer has for its target depends on how well the aptamer will fit into a cavity of the protein or target molecule. In other words, the binding between an aptamer and a target molecule is dependent on the surface residues of the antigen 307 and the structure of the aptamer 295.

FIGS. 18A-C are molecular diagrams of the capture of analyte with the SAW sensor. The active surface 14 functionalized with PGMA can be used to covalently attach antibody 40 or amino-modified aptamer 295; while pyrene derivatives 297 can be directly tethered to the pristine active surface through π-π interactions. The SAW sensor functionalized with the aforementioned modification process can then be used to capture any target analyte 42 of interest ranging from small molecules such as glucose, nucleic acids in FIG. 12A, peptides/proteins 311 in FIG. 12B and microorganism including bacteria and viruses 314 in FIG. 12C.

Instrumentation Circuits for Analytic Processing in Cell Arrays

Figure 13:
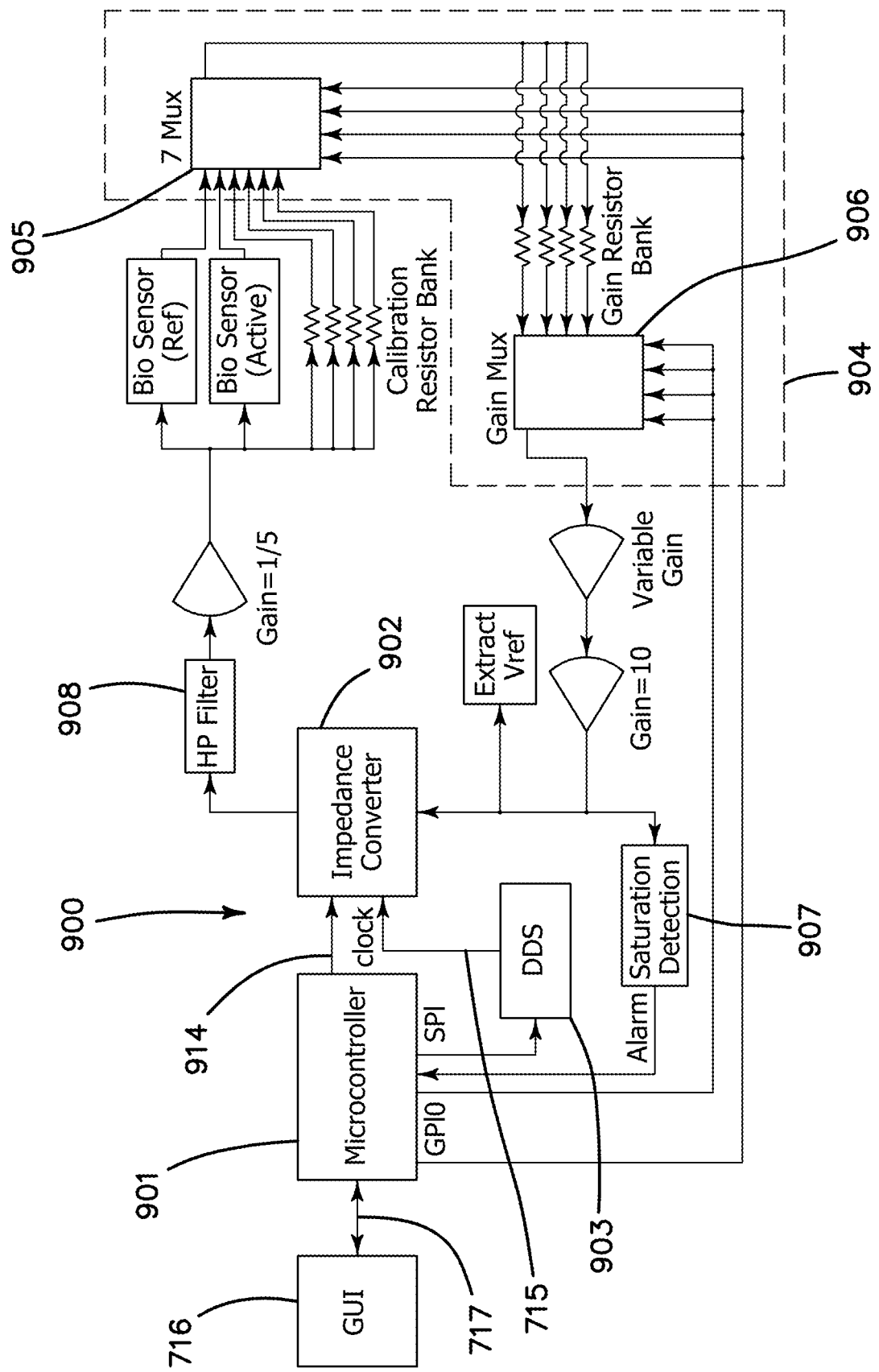
FIG. 13 is a block diagram of the electronic circuit, for the detection, analysis and data processing of the SAW biosensor.

FIG. 13 is a block diagram of the electronic circuit 900, which detects specific biomarker antigen(s) e.g., in serum, CSF, and bacteria in food employing the SAW sensor 1 after appropriate surface modification on the basis of application on hand. In the embodiment of FIG. 13 is a description of a time dependent measurement of the saturation of the sensor cell 34 is used as the data point. Circuit 900 includes a microcontroller 901, impedance converter 902, a direct digital synthesizer (DDS) 903, an analog front end (AFE) 904, a Z multiplexer (MUX) 905, a gain multiplexer (MUX) 906, and a saturation detection circuit 907. The circuit 900 operates with a sweep frequency of 50 Hz to 100 kHz. In one embodiment, the sweep frequency is capable of going to lower than 50 Hz with impedance range of 50Ω to 10 MΩ, providing for example 16 sweep points to define the linear response curve. It is within the spirit and scope of the invention to increase the number of sweep points to augment the number of data points and to further improve the statistics to represent a smoother linear curve. The apparatus 900 also includes additional mathematical signal processing tools within the microprocessor e.g. using a least squares or the polynomial curve-fitting algorithm by the Newton-Raphson method.

The apparatus 900 is a multiplexed data acquisition and analysis platform for measuring and recording of hybridization and flow cytometric analysis of analyte-antibodies in assays that performs simultaneous measurement of multiple different analytes. The system consists of an array of SAW cells 261 with a distinct sets of specific probes and the resultant output of the hybridization are addressable by the resident microcontroller 901 interfaced with a digital signal processing board and software. In one embodiment, we employ individual sets of microspheres such as gold nanoparticles (GNPs) 29 that can be modified with reactive components such as antigens, antibodies, or oligonucleotides, and then mixed to form a multiplexed assay set. The digital signal-processing hardware and software provide complete control of the flow cytometer and perform real-time data processing, allowing multiple independent reactions to be analyzed simultaneously. The system 900 performs qualitative and quantitative immunoassays for multiple serum proteins in both captures. The system can be used to perform DNA sequence analysis by multiplexed competitive hybridization with different sequence-specific oligonucleotide probes.

Figure 14:
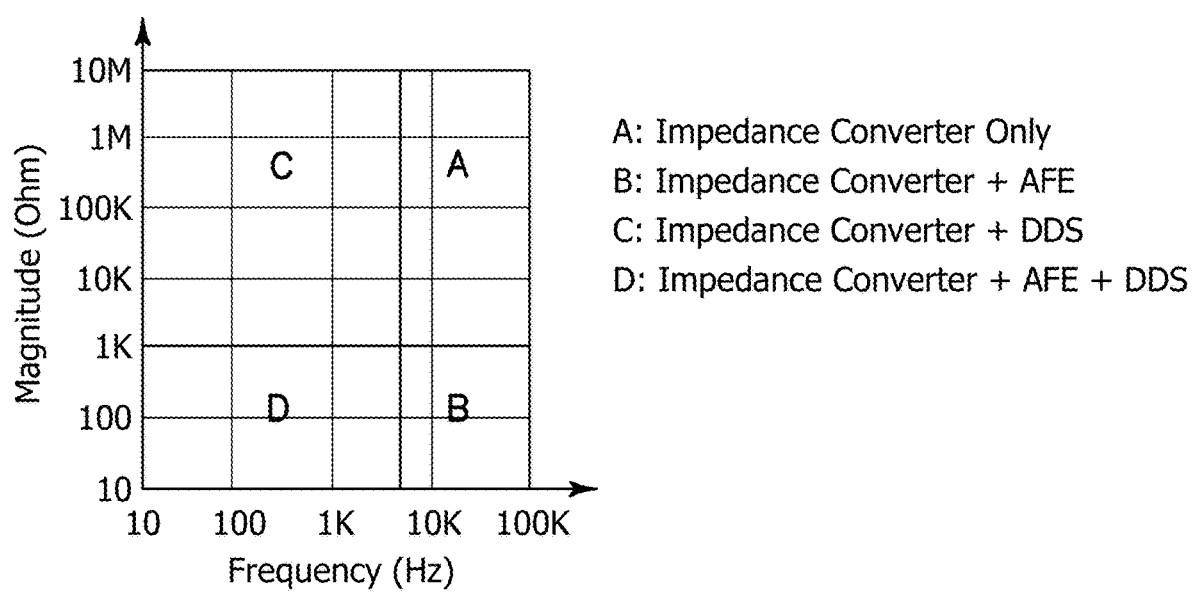
FIG. 14 is a graph representing the phase shift coverage range, with and without employing the analog front end (AFE) and direct digital synthesizer (DDS).
Figure 15:
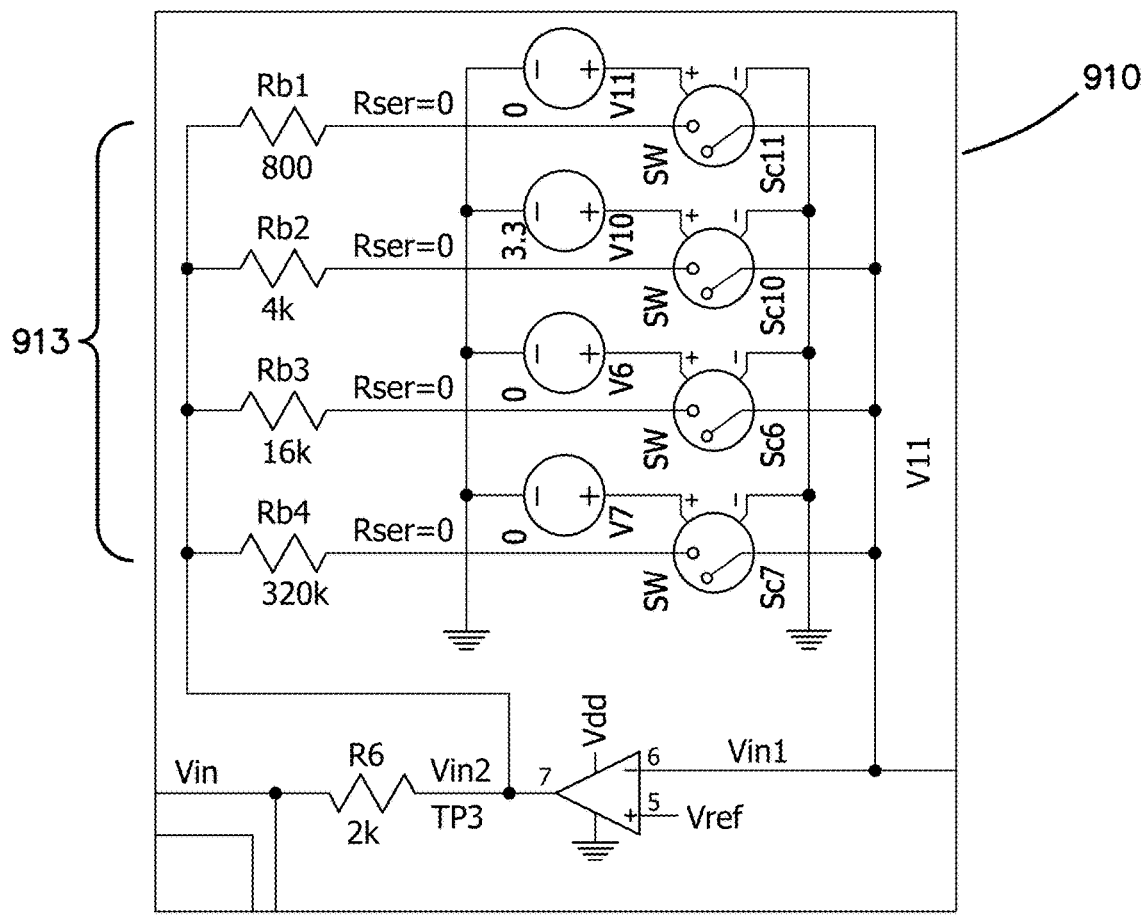
FIG. 15 is a schematic of a partial multi-gain stage post amplifier circuit that increases the range of impedance.

FIG. 14 is a diagram representing the phase shift coverage range 909 as a function of frequency with and without the use of the analog front end (AFE) 904 and direct digital synthesizer (DDS) 903. The impedance converter 902 has limited coverage in terms of frequency range and impedance range, as shown by region A, while region B indicates the expanded lower impedance measurement range provided by the inclusion of the DDS circuit 903, region C indicates the expanded lower frequency range afforded by the incorporation of the AFE circuit 904, and region D represents the fully expanded test frequency range and widened impedance measurement range employing the AFE 904 and DDS 903 together.

Further elaboration of the system 900 operation is noted by following FIG. 13 signal flow, where microcontroller 901 (such as PIC32MX380F512L) is used to direct traffic, CPU (MC) 901 further fetches instructions, decodes each instruction, fetches source operands, executes each instruction and writes the results of instruction execution to the proper destinations. The microcontroller 901 selects via gain multiplexer 906 a cell and compares the outputs of the SAW sensors 34 (or array 261) with impedance converter 902 (such as AD5933). The AD5933 is a high precision impedance converter system solution that combines an on-board frequency generator with a 12-bit, 1 MSPS, analog-to-digital converter (ADC). The frequency generator allows an external complex impedance to be excited with a known frequency. The response signal from the impedance cell is sampled by the on-board ADC and a discrete Fourier transform (DFT) is processed by an on-board DSP engine. The DFT algorithm returns a real (R) and imaginary (I) dataword at each output frequency. Once calibrated signal is achieved by comparing between biosensor signal cell and biosensor reference cell, the magnitude of the impedance and relative phase of the impedance at each frequency point along the sweep is easily calculated by the arithmetical unit (AU). The DDS 903 unit (such as AD9834) defines the clock traffic within the apparatus 900 with its other functional blocks of the analog front end 904. The SAW sensor outputs is constantly compared by the saturation detector 907 and enables a selection of the appropriate gain necessary for linearization as shown and described by FIG. 14 with its direct digital synthesizer (DDS), FIG. 15 where the signal undergoes a multi gain stage which increases the impedance range, and FIG. 16 where saturation detection circuit determines the appropriate value to be selected from the gain bank resistor 906.

The benefit of using the external AFE circuit 904 is that it provides reduced output impedance of the signal source, where the impedance converter 902 has output resistance associated with each programmable output voltage (200Ω to 2.4 kΩ), while employing a low-output impedance (<1Ω) source follower amplifier 27 with sufficient bandwidth as a buffer to eliminate the effect of noise on the impedance measurement sampled by the apparatus 900.

To re-bias the excitation signal, each programmable output voltage in impedance converter 902 has a different bias associated with it, and adding high pass filter 908 to remove the DC bias from the transmit stage and re-biasing the AC signal allows the DC bias to be re-centered at midpoint, $V_{dd/2}$. Since the amplifier 910 in FIG. 15 on the receiving path is also DC biased at $V_{dd/2}$, there is zero DC bias applied to the biosensor. This avoids possible thermal damage to the fluid sample (antibody and analyte) due to an applied voltage over a long measurement time.

Since the smallest excitation signal $V_{pp}$=198 mV and $V_{dc}$=173 mV from impedance converter 902 is greater than what the biosensor 1 requires, in one embodiment, op-amps are employed to further attenuate the excitation signal to 40 mV, and to apply proper gain before feeding the signal back to the impedance converter 902. Due to the complex nature of biosensor impedance over wide sweep frequency, the impedance value may be as small as few may dozen ohm, and as large as several Mega ohm. The active circuit 900 is designed to measure impedance from 100Ω to 10 MΩ namely a ratio=10 MΩ/1000=100000.

FIG. 21 is a schematic of partial multi-gain stage post amplifier circuit 910 included in gain multiplexer 906, which is incorporated to solve the wide impedance range problem expressed in FIG. 14, where the impedance range spans from 10 MΩ to 100Ω. This order of magnitude range is achieved by placing a multiple resistor bank 913 as the gain feedback resistor of the post-amplifier 910, using in this example four switched resistors to cover the entire sampling range. The calibration resistor bank 913 is included to provide individual calibration at each gain stage.

Figure 16:
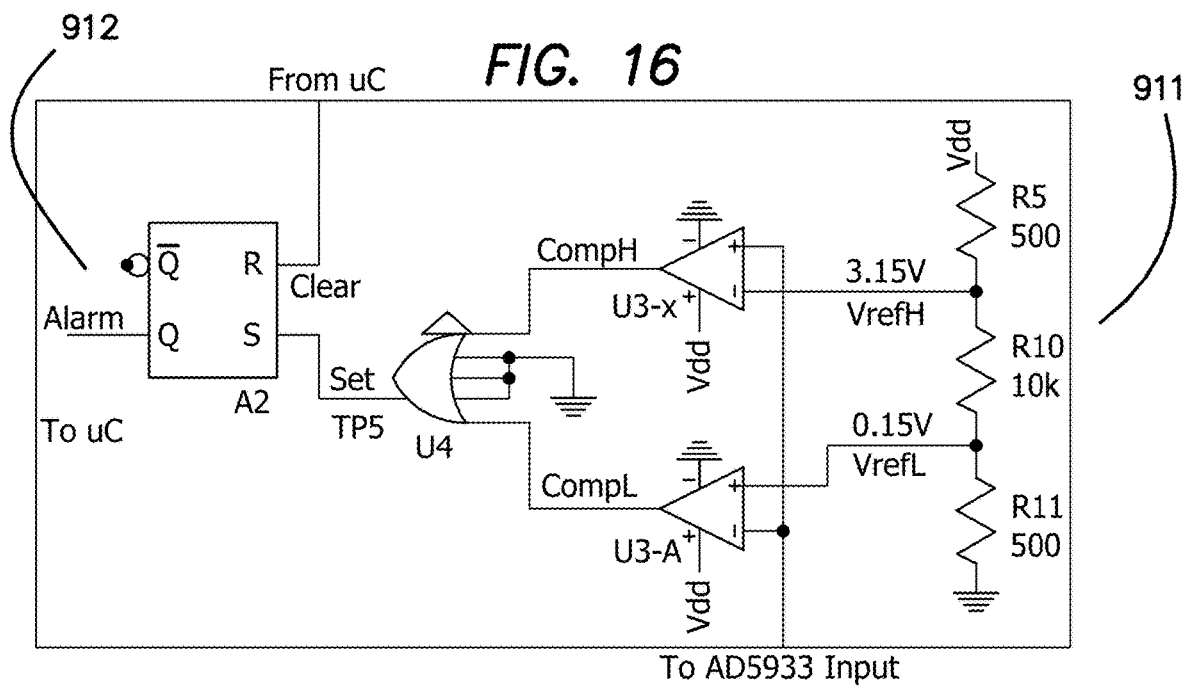
FIG. 16 is a schematic of a partial saturation detection circuit, which takes the post amplified signal (0 to 3.3 V) provided to the AD5933 impedance converter, and compares it with the high (VrefH=3.15 V) and low (VrefL=0.15 V) thresholds.

FIG. 16 is a schematic of a partial saturation detection circuit 911 included within saturation detection circuit 907, samples the post amplified signal (0 to 3.3 V) provided to the impedance converter 902, and compares it with the high (VrefH=3.15 V) and low (VrefL=0.15 V) thresholds. If the signal is out of the range, the comparator outputs CompH and/or CompL will be high, causing the alarm to be set by the flip-flop 912. The alarm is monitored by the microcontroller 901, and triggers the auto gain selection software module to lower the input amplifier gain in gain multiplexer 906 by selection of an appropriate resistor value in circuit 910 in FIG. 15, which is included in gain multiplexer 906. The microcontroller 901 then clears the alarm by setting the reset pin, CLEAR, high in the flip-flop 912 of circuit 911 in FIG. 16.

Figure 17:
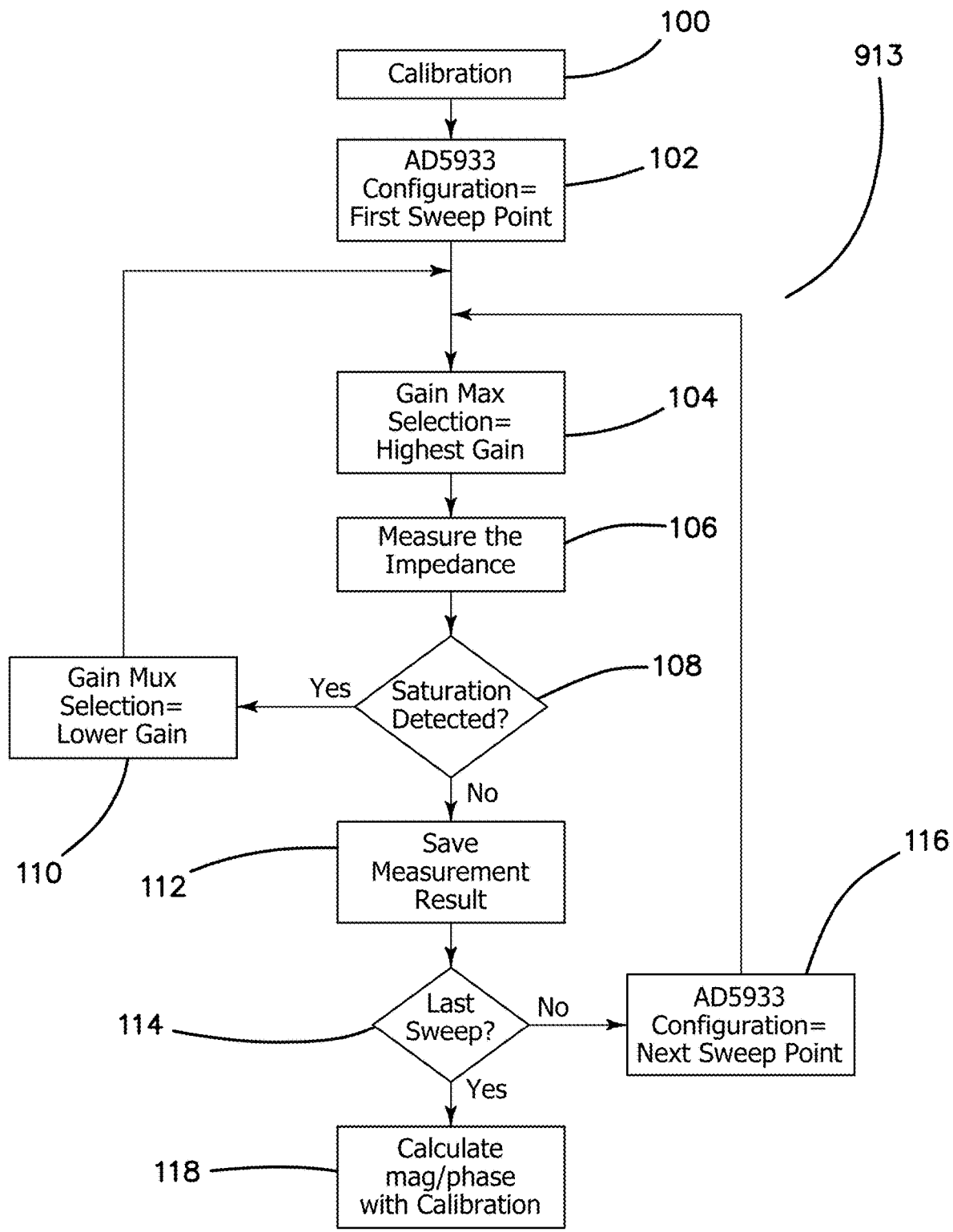
FIG. 17 is a flowchart detailing the auto gain selection software logic designed to select the proper post-amplifier gain based on the saturation detection circuit output to insure the impedance signal within the AD5933 impedance converter line.

FIG. 17 is a flowchart 995 detailing the auto gain selection software logic in microcontroller 901 designed to select the proper post-amplifier gain based on the output of saturation detection circuit 907 to insure the impedance signal within impedance converter 902 is within its linear range. In one embodiment, the embedded software is designed to function as a state machine to control the impedance measurement sequence of impedance converter 902 over output 714, and to further provide control of DDS 903 over output 912.

FIG. 17 further illustrates the methodology of the impedance measurement sequence of circuit detail defining the impedance converter. Calibration begins at step 100 followed by configuration of the circuit 902 (impedance converter using e.g. a device such as AD5933) at the first frequency sweep point at step 102. The gain of gain multiplexer 906 is set at its highest gain at step 104. The impedance at the first sweep is then measured at step 106. A determination is made at step 108 whether or not saturation has been achieved. If saturation has been achieved, then the gain of gain multiplexer 906 is set to a lower level at step 110 and the process returns to step 104 for the next series of sweeps. If saturation has not been achieved, then a measurement result is saved by microprocessor 901 at step 112. A determination is then made at step 114 whether or not the frequency sweep just made is the last one to be made in the series or not. If not, then the next frequency sweep point is selected at step 116 and the process returns to step 104. If the frequency sweep made is the last one of the programmed series, then the calibrated magnitude and phase of the impedance is calculated at step 118.

In another embodiment, the software provides the communication protocol with the graphic user interface (GUI) 918 over universal serial bus (USB) 919. In another embodiment, the software provides general-purpose input/output (GPIO) control of gain and Z multiplexing. In another embodiment, the software provides an alarm in the event of saturation detection.

In another embodiment, the software provides variable gain selection, and automatic calibration of the system. The flow diagram depicts an impedance converter 903, which is a high precision impedance converter system solution that combines an on-board frequency generator such as for example Analog Devices AD5933 with a 12-bit, 1 MSPS, analog-to-digital converter (ADC). The frequency generator allows an external complex impedance to be excited with a known frequency. The response signal from the impedance measurement is sampled by the on-board ADC and a discrete Fourier transform (DFT) is processed by an on-board digital signal processor DSP engine in converter 903. The DFT algorithm returns a real (R) and imaginary (I) dataword at each output frequency for impedance. Once calibrated, the magnitude of the impedance and relative phase of the impedance at each frequency point along the sweep is calculated. This is done by microcontroller 901 using the real and imaginary register contents, which can be read from the serial I²C interface. The microcontroller 901 commands the gain multiplexer 906 to select the proper resistance value as indicated and described by FIG. 14, if saturation is detected by the circuit 912 defined by FIG. 16 then the microcontroller 901 commands the multi-gain circuit 910 described in FIG. 15 to select the appropriate value, and the measurement is taken and stored. The process is reinitiated upon command from the microcontroller 901.

Figure 18:
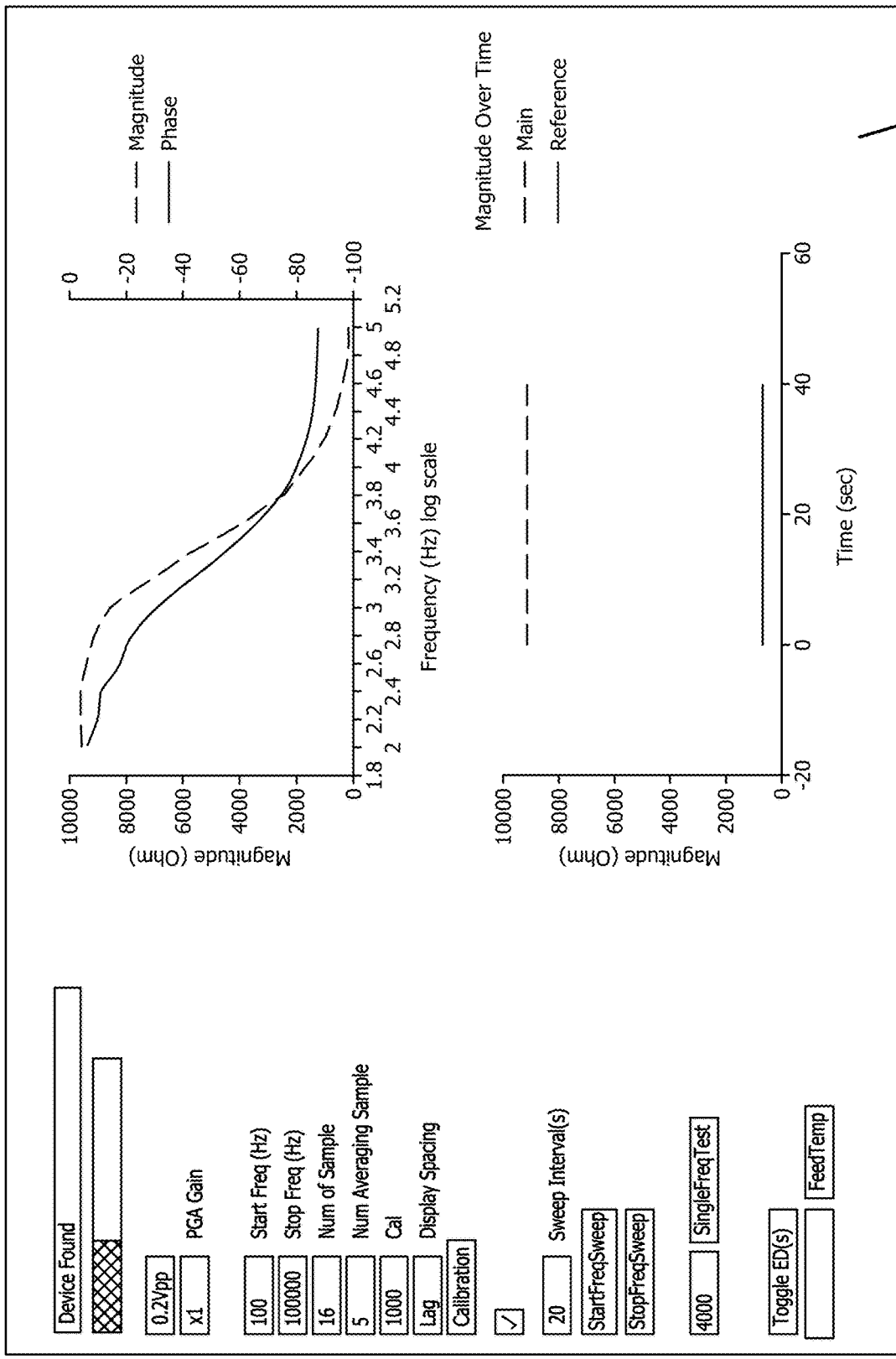
FIG. 18 is a screenshot of a graphic user interface (GUI) used in the apparatus of the illustrated embodiments.

FIG. 18 depicts a display screen 918 of the graphic user interface (GUI), indicating the various parameters needed to enable the user interface to perform the tasks and display the relevant data and analysis of the SAW sensor 1. The data mining as well as data reduction and display are noted in examples using MATLAB for a finite state machine, to control and model the SAW sensor array, can configure and modify the visual and fields of interest on demand. Using finite state machines to model control logic of a reactive system displays a finite set of states and behaviors and how the system transitions from one state to another when certain conditions are true. Examples of operations containing complex impedance measurements, includes scheduling a sequence of tasks or steps for a system defining fault detection, isolation, and recovery logic supervising how to switch between different modes of display and analysis options.

Circuit Modeling of the SAW Cell

Figure 19:
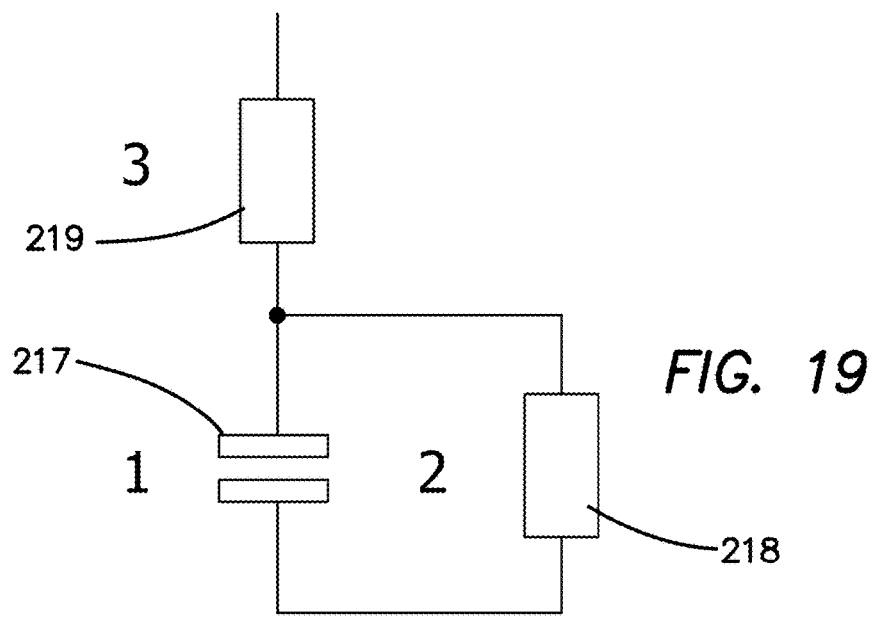
FIG. 19 is an equivalent circuit of the sensor and/or reference cell.
Figure 20:
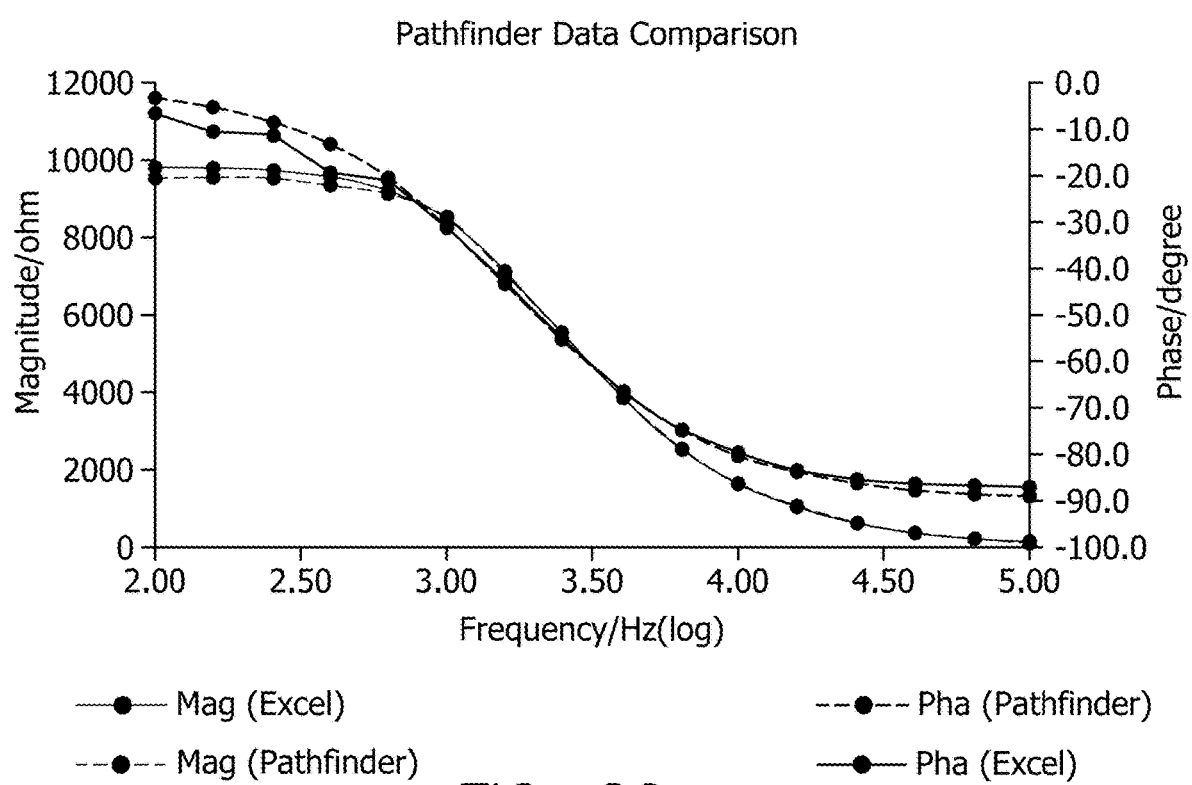
FIG. 20 is a graph of the impedance and corresponding phase change as a function of the applied frequency. Pathfinder observed the data. Two sets of data were plotted together.

FIG. 19 shows an R/C equivalent circuit of sensor 34 where R 218 and C 221 are in parallel. Where R 218=10 kΩ (9.86 kΩ measured) and the value of C 221=10 nF (9.5 nF measured). Using this equivalent circuit of sensor 34 as exemplified by a prototype fabricated at our laboratory, a set of experiments were conducted in order to validate the modeling of the novel biosensor 1 and it's analog-front-end. The device-measured impedance against the sweep frequency from 50 Hz to 100 kHz indicated a close correlation between data obtained vs. theoretical prediction of the SAW sensor 1. The data were collected using the developed impedance measurement device, i.e., Pathfinder or Reader of FIG. 6, and the plotted data indicate the observed impedance value against the applied frequency using excel via MATLAB, employing the general expression for impedance of 50 Hz to 100 kHz CPE is as follows:

$$Z_{CPE} = \frac{1}{\omega_0 \cdot V} \cdot \left(\frac{j\omega}{\omega_0}\right)^{-a}$$

Where V is the voltage across the sensor 1, ω is frequency applied to the sensor 1 and $\omega_0$ is the frequency of 50 Hz to 100 kHz. Here, α value is in between 0 (Zcpe becomes entirely resistive) and 1 (Zcpe becomes entirely capacitive). We have seen the alpha range from 0.5 to 0.9 depends on the data set and modeling configuration and the a value changes during the anti-body/antigen conjugating process. In the time domain, a simple exponential curve for the R/C equivalent circuit did not accurately describe the actual circuit equivalence of the sensor 1. The R/C network's impedance is calculated in an Excel spreadsheet using Matlab. The test data is collected using Pathfinder. The calculated and measured data are plotted against each other in FIG. 20. The graph of FIG. 20 shows the magnitude of the impedance and its corresponding phase change with the applied frequency.

A biosensor 1 was tested to compare the results observed by Pathfinder of FIG. 6 and a commercially available electrochemical impedance spectroscopy (EIS) (Zahner, Model #IM6). Both results are shown in the FIG. 27. The data observed at the frequency range from 3 kHz to 300 kHz. The impedance increases with the decreasing frequency for both cases, which is supported the theoretical model. FIG. 28 is a graph comparing the phase of the impedance as observed by Pathfinder in FIG. 6 and a commercially available electrochemical impedance spectroscopy (Zahner, Model #IM6). The same biosensors 1 were used for both cases.

Analog Computational Unit Included in the Analog Front End

FIG. 22A-30D are schematics of analog operational circuits that may be used in an analog computational analyzer used in the application incorporating the principles of cellular SAW array, where a parallel computing paradigm similar to neural networks is applied in order to solve the diffusion as well as the hybridization problem for a variety of proteins and DNA captured by the apparatus 900 in a manner in which the cellular biological process-dynamics is mimicked and the underlying protein sequences observed in the sensor 1 is counted and certain arithmetical procedures are applied. It is to be understood that many other analog operational circuits in addition to those shown in FIG. 22A-30D could be included.

Following Shannon, C E. 1941. "Mathematical Theory of the Differential Analyzer." We employ an analog computation method with an exemplary rendition of such circuit, as it is a better analytical tool-modeling for capturing analyzing and reporting of biological process, as its structure as well as its operation, where Diffusion, Hybridization, Bio-Kinetics, are process which its continues/non-discrete nature is better represented and accurately resemble the physical laws and where computation is realized as an analogue function. One essential property of analog circuits is the ability to use fewer devices than corresponding digital circuits, for example, a four-quadrant adder (capable of adding two signed numbers) can be fabricated from four transistors, and where two transistors are sufficient to compute the logarithm or exponential, five for the hyperbolic tangent (which is very useful in neural computation), and three for the square root. As discussed herein, an analog computation unit is incorporated to enable the apparatus 900 with its SAW 1 in a sensor array configuration 261 to generate data stream manipulated by the arithmetical operators such as described by FIG. 22A-30D.

FIG. 22A shows a summing amplifier, FIG. 22B shows a difference amplifier, FIG. 22C shows an integrator and FIG. 22D shows a differentiator. The analog computation devices of FIG. 22A-D employing the SAW cell unit 1 in an array matrix-configuration are combined and arranged to perform algebraic and integro-differential operations acting upon continuous or analog signals. The high gain D.C. source follower amplifier 27 as exhibited by the configuration of SAW cell 1, forms the basic operational element of detection. If the passive components in both feedback and input arms are entirely resistive, the circuits of FIG. 22A add the applied voltages in proportion to the ratios of the individual resistors. If the feedback impedance is capacitive, the circuits integrate the sum of the applied voltages, as shown in FIG. 22C. The simplest input and feedback impedances are replaced with complex networks, either passive or active, the amplifier circuit develops more complicated transfer functions than those shown in FIG. 22A-30D, but a general propose analog computer employing a multiplier may be used to form the product of two or more variables. In addition, a fixed and variable diode function generators are available to perform various non-linear operations, and a comparator may make elementary decisions based on the value of a particular variable.

The circuit architecture shown in FIG. 32 includes the analog front end 904 coupled between the sensor array 261 of a plurality of sensor and reference cell pairs 34(n), each pair coupled to a corresponding log amp 8 and filter 908 and through multiplexer 804 to the digital back end including microprocessor 901. The output signal from filter 908 is a continuous analog signal. The apparatus mimics the underlying biological processes employing discrete state spaces. This data is then manipulated by the arithmetical modules (AU) 300 which mathematically describe the physical process operating on time-varying quantities. The analog computational unit 300 and the digital peripherals shown in FIG. 23, record, store and analyze the hybridization as well as the diffusion processes, which underlay the biology investigated by the apparatus 900.

FIGS. 31A-31D are schematic diagrams of the arithmetical units (AU) 300 that forms the analog computational apparatus of the SAW cells 261. The use of the SAW sensor as configured in this application is an electronic device for low-power low-voltage digital or analog circuit application. In one of its embodiments, we teach a low-power, low-voltage SAW's construction with its operational amplifier (OPAMP), forming an analog arithmetic computing circuit, acting as operators in an analog calculator, where the basic building block are: an inverting amplifier, non-inverting amplifier, adder, substractor, differentiator, and integrator. Example of such an operator acting on the data generated by hybridization is described in FIG. 23B.

FIG. 23A is a schematic block diagram describing the interconnection between the sensor array signal outputs from filters 908 into a universal analog multiplexer 955 including in analog front end 904 in FIG. 23. The multiplexer 955 further enables the selection of the arithmetical operator 914, 915, 916, 917 forming the AU 300. On command from microcontroller 901 the multiplexer 955 enables the command via analog computational unit 953 to select the desired arithmetical operation within AU 300.

FIG. 23B is a schematic representation of one of optional configurations of connectivity of SAW 1 (sensor S1 and S2) with the analog arithmetical module (AU) 300. The circuitry is an exemplary demonstration of the multiple configurations by which the SAW sensor unit 1 can be interfaced with the AU 300. In one embodiment, two SAW sensors 1 are used and are connected to the AU 300 as two inputs. In addition, the AU 300 circuit is fitted with variable gain in the form of the extra FET transistor Q5, where the control transistor bias Q5 changes the gain of the section.

The circuit of FIG. 23B is an illustration of the use of the arithmetical analog calculator in use with the SAW sensor, comprising of two SAW sensors are shown as S1 and S2. Both are connected to a voltage amplifier, A1 and A2 respectively. The sensor(s) output two voltages, which are proportional to the chemical/biological activity (the hybridization rate of analyte/antibody). These are shown as V1 and V2. These two signals are taken to the inputs of the arithmetical module 300, configured by four FET transistors and are marked as Q1, Q2, Q3 and Q4. The FET Q5 serves as a bias transistor. The four transistors together compute (in this exemplary case) the tanh (hyperbolic tangent) function of the difference between the two input signals, V1 and V2. In addition, the AU 300 also computes the derivative of the same function (d/dt of tanh). A simple difference between the two signals is also present. The (AU) 904 outputs are represented as currents, marked as I1, I2 and I3. These currents are proportional to the functions described above. It is necessary to convert these current signals to voltages, hence the addition of the three resistors, R1, R2 and R3. An additional stage of amplification is added to each of the signals after conversion to voltage; indicated as A3, A4 and A5. While considering the energy used in the detection as well as the resulted arithmetical operation, the circuit in FIG. 23B exhibited the substantial saving while performing such operation. The energy budget is in the range of a few femto-amps and it is much more efficient then a digital mathematical computation circuit, when performing similar operation.

In the illustrated embodiment, however, the analog computation unit 300 may provide familiar operations that use differential equations. These include basic arithmetic operations in FIG. 22A-30D, such as algebraic sum 914 and difference 915 ($u(t)=v(t)\pm w(t)$), constant multiplication or scaling ($u(t)=cv(t)$), variable multiplication and division ($u(t)=v(t)w(t)$, $u(t)=v(t)/w(t)$), and inversion ($u(t)=-v(t)$). Transcendental functions may be provided, such as the exponential ($u(t)=\exp v(t)$), logarithm ($u(t)=\ln v(t)$), trigonometric functions ($u(t)=\sin v(t)$, etc.), and further option is the use of a re-solvers for converting between polar and rectangular coordinates. In addition, the arithmetical unit 300 perform a definite integration 916 ($u(t)=v_0+\int_{t_0} v(\tau)d\tau$), but differentiation may also be provided 917 ($u(t)=v(t)$).

Reaction-diffusion computation is an important example of continuous-time analog computing within the framework of the apparatus 900, which could be computed in AU 300. In one example, the state of the system apparatus 900 with the analyte is represented by a set of time-varying chemical concentration fields, $c_1, \ldots, c_n$. These fields are distributed across a one-, two-, or three-dimensional space $\Omega$, so that, for $x \in \Omega$, $c_k(x, t)$ represents the concentration of chemical (k) at location x and time t. Computation proceeds in continuous time according to reaction-diffusion equations, which have the form: $\partial c/\partial t = D\nabla^2 c + F(c)$, where $c=(c_1, \ldots, c_n)^T$ is the vector of concentrations, $D=\text{diag}(d_1, \ldots, d_n)$ is a diagonal matrix of positive diffusion rates, and F is nonlinear vector function that describes how the chemical reactions affect the concentrations.

There are many variations as well as configurations of interfacing the arithmetical unit with the SAW sensor array 261 and the analog-front-end 904, in one preferred embodiment the analog arithmetic unit 300 and the analog front end 904, function as one integral signal path, to maintain the continuous nature of the signal fidelity, mimicking the underlying cellular biological process in which hybridization and its diffusion coefficient, including its native time constant as well as its impedance value as measured in array 261 are preserved, prior to any digital filtering or smoothing (curve fitting algorithm) the resulting analog signal with its amplified gain and its arithmetical manipulation, is one of the essential embodiments of the proposed apparatus.

If the simple input and feedback impedances are replaced with complex networks, either passive or active, the amplifier circuit will develop more complicated transfer functions than those shown. In addition to the basic amplifiers, the general purpose analog computational unit contains a variety of special purpose units; for example, multipliers to form the product of two or more variables, fixed and variable-diode function generators to perform various nonlinear operations on the variables, switches to start and modify the operations, and comparators to make elementary decisions based on the value of a particular variable. It is the compatibility and simplicity of interconnection of these various components that give the analog computation its flexibility and versatility. An analog computer interface (ACI) is useful in a variety of applications although a digital electronic computer is used in the back-end to process the data. The analog interface is well suited for the solving differential equations (PDE), specifically non-linear differential equations and systems of equations required in mimicking the biological processes. The analog computation unit is comprised of circuits that can perform addition 914, subtraction 915, multiplication, division, integration 916, and differentiation 917, which enable the proposed apparatus 900 to reliably mimic the stochastic-statistical nature of the underlying electrochemical processes which ultimately provide a realistic ground for the biological sequences investigations, as well as the ability to capture and mimic biological processes.

In one of the preferred embodiments of this application, the apparatus and its method solve specific mathematical operations needed in resolving the diffusion equation as well as hybridization of the antibody-analyte conjugate. The mimicking of such biological processes is performed by connecting SAW cells 34 with analog circuits to record continuous biological processes, in which the hybridization sequencing order in cellular process is replicated in apparatus 900, by employing a suitable memory bank 813. The data recorded and or analyzed by the resident microcontroller 901 and its associated memory bank can be used as part of the underlying information necessary to understand stochastic hybridization of such biological processes, hence provide a window to the resulting vectorial trends which ultimately contribute to the resulting protein product at the end of the chain in the mimicked cellular process. Inputs to the circuit are voltages which usually vary with time in a prescribed manner and measurement of the output voltage yields the equation's solution as a continuous representation of the effective capacitive loading and its inverse impedance equivalent value.

The method and apparatus proposed by the invention enable the measurement of such process by its ability to capture and analyze the data in the time domain as well as its frequency domain, hence providing for a realistic representation of the underlying biology and its equivalent circuit.

In one embodiment the layout of the circuit and the SAW cell's position are configured in a manner, which enables a measurement of sequence and timing of the hybridization process. Such data of sequencing and time further enable statistical mapping of biological processes.

In other embodiments, data sampling can also be time delayed to allow for sequence processing in the temporal domain. The definition of a system is a collection of independent, interacting entities forming an integrated whole, whose behavior is distinct and qualitatively greater than its parts. Although data samples are specific to individual cells, global patterns in the data can emerge through application of a diffusion algorithm to the data residing in microcontroller 901. In this sense, the analog front interface with its digital processor enables multiple parallel systems of hybridization to be traced, due to their dynamics, and data patterns are derived from the correlation or relationship of data sequences between the different SAW cell's units in the array 261 by using different antibodies located in different SAW cell units.

An example for such use is the flow of an analyte sample containing multiple biomarkers (antibodies) 28 and where different SAW sensors 1 measure and record the hybridizations of two or more of such biomarkers antigens 29 simultaneously. A typical diagnostic procedure, which enables the correlation of such, is noted by measuring the presence and densities of multiple biomarker and their respective values such as VEGF165, C-ERBb-2 AND P53 from a patient's sample by obtaining the density matrices of the three biomarkers in one continues dataset, by the use of apparatus 900. The simultaneous hybridization of multiple biomarker is here analyzed as a phase space of multidimensional vectors to enable the resultant data to lead to a statistical correlation of possible causal connection between multiple biomarkers such as VEGF165, c-ERBb-2 AND p53. A density matrix for a biomarker is thus a matrix that describes a system where different parameters are available at the same time, such as impedance, time and geometrical location of the cell, which enables a recordation of the physical density, location and type of antibody/antigen. This is to be contrasted with a single state vector that describes an assay where multiple analytes are measured. The density matrix is the analogue to probability measure (probability distribution of position and time of hybridization). The classical parameterization of phase space statistics can be used as a tool to represent the hybridization of multiple biomarker simultaneously to enable the resultant data to lead to a statistical correlation of possible causal connection between multiple biomarkers such as: VEGF165, C-ERBb-2 AND P53 as clinically an augmentation of the three biomarkers with a positive vectorial change is statistically significant in determining the presence of e.g. breath cancer.

A density matrix is a matrix that describes a system in a state where different parameters are available at the same time, a measure of several elements within that state (time and geometrical location) within a state enable a recordation of density, location and type of antibody/antigen This should be contrasted with a single state vector that describes an assay where multiple analytes are measured The density matrix is the analogue to probability mea sure (probability distribution of position and time stamps of hybridization) and it is assumed as the measure of phase space in classical statistical mechanics.

To emulate and represent a biological sequencing as state-by-state hybridization, an analog computing device of the kind described by the application is needed to enable direct solution of polynomial differential equations (PDEs). In general a PDE solver depends on an analogous physical process, that is, on a process obeying the same class of PDEs that it is intended to solve. For example, in Mills, J. W. (2008). "The nature of the extended analog computer." Physica D: Nonlinear Phenomena 237 (9) (Elsevier). pp. 1235-1256, and following Lee A. Rubel, describe use of analog circuit in mimicking the diffusion of electrons in conductive sheets or solids to solve the diffusion equations. In mimicking "reaction-diffusion" biology, a continuous-time analog computing, is a necessary step in preserving the fidelity of the process. The state is represented by a set of time-varying chemical concentration fields, c1 ... cn. These fields are distributed across a one-, two-, or three-dimensional space $\Omega$, so that, for x $\Omega$, ck(x, t) which represents the concentration of analyte k at location x and time t. Computation proceeds continuously in time according to reaction-diffusion equations, which have the form: $\partial c/\partial t = D\ 2c + F(c)$, where $c = (c1 \ldots cn)T$ is the vector of concentrations, $D = diag(d1, \ldots, dn)$, is a diagonal matrix of positive diffusion rates, and F is nonlinear vector function that describes how the chemical reactions affect the concentrations. The use of the analog module (AU) 904 enable such procedure and realization of the Lee A. Ruble's architecture in addressing the effective solution of PDE and their accuracy (precision), by preserving the actual and realistic underlying biology in a continues form and without the customary digital discrete and filtered data reduction. The embodiment noted is used by the apparatus to solve the time varying changes occurring due to hybridization kinetics and solve the problem of how to measure continuously the conjugation between the probe on the sensing lane and the analyte concentration. The data set generated provide an additional measure of reliability to the apparatus and enable the system to correlate concentration value of the analyte and its hybridization rate.

A careful review of the embodiments of the invention, demonstrate the ability of the cellular array of SAW 1 sensors to capture, measure, count and analyze the entire biological process of molecular conjugation, in an analog continuous and reliable fashion to enable the tasks of mimicking computational biology in a novel, effective and were results are consistent with scientific standards.

A Clinical Example for the Use of the Apparatus as a Prognostic Tool.

One of the preferred embodiments for the effective use of the apparatus is to assess the prognostic significance of molecular biomarkers, particularly c-erbB-2 and p53 and VEGF165. Defining molecular abnormalities in breast cancer is an important strategy for early detection, assessment of prognosis, and treatment selection. Evidence is strong that selective biomarkers, including c-erbB-2 and p53, have prognostic significance in breast cancer. Study conducted by Beenken S W, et al "Molecular biomarkers for breast cancer prognosis: co expression of c-erbB-2 and p53. (PubMed 2001 May; 233(5):630-8) support the application of the novel apparatus 900 as the author conclude that." Three hundred eleven patients were accrued to the Alabama Breast Cancer Project, and paraffin-embedded breast cancer tissues for 90 patients were available for immunohistochemical analysis of molecular biomarkers. Univariate analysis showed nodal status, c-erbB-2 expression, and p53 expression to have prognostic significance. Co expression of c-erbB-2 and p53 was also found to have prognostic significance by the log-rank test. Multivariate analysis showed T stage, nodal status, c-erbB-2 expression, and p53 expression to have independent prognostic significance. These data suggest that c-erbB-2 and p53 expression in breast cancer have prognostic significance. After median follow-up of 16 years, co expression of c-erbB-2 and p53 may have more prognostic significance than traditional prognostic factors such as T stage and nodal status". The use of the apparatus 900 with its ability to enable a label-free detection by hybridizing multiple biomarkers simultaneously without the preparation and technical knowhow of laboratory immunostained sections and immunohistochemical determination after sectioning can be achieved by the use of the proposed apparatus and the method we teach in this application. The example of such use is obvious to a man familiar with the art, as a possible layout of the apparatus 900 can be set to contain an array 261 of SAW 1 with a biomarker such as: c-erbB-2-rabbit antihuman c-erbB-2 oncoprotein and second biomarker: p53-mouse monoclonal antihuman p53 (Both antibodies are produced by DAKO, Carpentaria, Calif.), and where SAW array for both biomarkers are prepared with its specific antigen (as noted above), and where a serum of a patient is introduced to the microfluidic chamber 139 to enable measurement of the hybridization process while setting the normal histological reference within the apparatus lookup tables for comparison or alternatively the reference data point can be set as resistor bank within the apparatus. The application as noted can be expended with variations relating to the number of SAW 34 cells in the array 261 and with different geometrical lay outs as shown in FIGS. 22 and 7A respectively.

FIG. 23 is a schematic representation of analog front end (AFE) 904 with its analog computational unit 300 (arithmetical module). The analysis and selection of the analog computational module is based on the fundamental laws of noise in gene and protein expression, which set limits on the energy, time, space, molecular count and part-count resources needed to compute at a given level of precision (a biological process of hybridization) including the fact that such process invariably take into accounts the diffusion coefficients of such activity, such as hybridization. The literature and comparative studies conclude that analog computation is significantly more efficient in its use of resources than deterministic digital computation modeling, even at relatively high levels of precision in the cell. Based on this analysis, we conclude that synthetic biology must employ an analog, collective analog, probabilistic and hybrid analog-digital computational approaches. Otherwise, even relatively simple synthetic computations in hybridizing protein, such as addition, (as is it demonstrated by example below), will exceed energy and molecular-count budgets. The application further introduces a method and an exemplary apparatus for efficiently representing analog protein-to-protein computation in vitro. As noted by the prior art of Synthetic Biology: analog electronic circuits operating with sub-threshold transistors and analog molecular flux in chemical reactions, both obey Boltzmann exponential laws of thermodynamics and are described by similar logarithmic electrochemical potentials. It is to be noted that the basic modeling and verification of the preferred embodiments for this application is the ability of the computational unit (AU) 300 of its apparatus 900 to mimic the underlying biological diffusion and hybridization modeling. This application uses recent work, which was conducted in our laboratory and confirmed the use of the invention employing *Escherichia coli* and VEGF molecule by further demonstrating the effective realization of the proposed method and its embodiments.

There are striking similarities between chemical-reaction dynamics and electronic current flow in the sub-threshold regime of transistor operation: electron concentration at the source is analogous to reactant concentration; electron concentration at the drain is analogous to product concentration; forward and reverse current flows in the SAW transistor are analogous to forward and reverse reaction rates in a chemical reaction; the forward and reverse currents in a SAW transistor 1 is exponential in voltage differences at its terminals analogous to reaction rates being exponential in the free-energy differences within a chemical reaction; increases in gate voltage lower energy barriers in a transistor increasing current flow analogous to the effects of enzymes or catalysts in chemical reactions that increase reaction rates; and the stochastic of the Poisson shot noise in sub-threshold transistors are analogous to the stochastic of molecular shot noise in reactions.

As shown by FIGS. 1A and 1B and system diagram noted by FIG. 13, where the basic cell unit 1 forming in array configuration 261 and where the SAW cell 34 is a hybrid of semiconductive substrate and a biological element (antibody) the bio-electronic circuit functions as an analog device. The array of cellular elements form a matrix which enables the matrix to perform as a statistical engine to solve partial differential equations of a kind necessary to address two fundamental problems presented by computational biology: mimicking the diffusion process of the underlying biological activities and the statistical counting of hybridization of protein and analyte in near real time.

The disclosed method for detecting the biological process of protein to protein conjugation while counting and recording it using SAW cells 34 in an array 261 enables continuous analysis by employing the analog front end (AFE) 904, using its analog computational unit (AU) 300, to measure the density matrix with its time-stamps and location of events with one step.

This process is defined by the embodiments of this application as each of the SAW cells 1 and its array shown in FIG. 6 with its addressable register via the multiplexer (the universal switch 908) and the general purpose MUX 804. The integration of micro-fluidics chamber 139 combined with its electrical impedance spectroscopy-analog-front-end 904, mimicking the underlying biological processes through its equivalent circuit. The ability of apparatus 900 to account for diffusion rate as well as the hybridization is a feature of the illustrated embodiments.

The definitions of the words or elements of the following claims are, therefore, defined in this specification to include not only the combination of elements which are literally set forth, but all equivalent structure, material or acts for performing substantially the same function in substantially the same way to obtain substantially the same result. In this sense, it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a sub combination or variation of a sub combination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is concep-

What we claim:

1. A shear horizontal surface acoustic wave (SH SAW) biosensor with an improved limit of detection (LOD), increased bandwidth, improved accuracy and resolution comprising:
a crystal resonator with electro-acoustic characteristic formed out of a 36°, Y-cut, X-propagation LiTaO₃ substrate;
a microfluidic chamber integrated with interdigitated input/output frequency matched electrodes in which the crystal resonator is disposed in combination with a paired sensing lane and reference lane;
a microcontroller;
an electronic analog front end interface (AFE) with a computational module for algorithmic data analysis and reporting coupled with the microcontroller; and
a biochemical probe formed in a surface array, each biochemical probe having a sensing lane for detection with a LOD of at least clinical threshold values,
where the sensing lane comprises a layering of antibodies, fragmented Ab, and the use of spacer-molecules to eliminate a false positive or a false negative, where the biochemical probe is a protein engineered probe using phage display combinatorial antibody library to utilize in the sensing lane a specific antibody with an affinity exceeding monoclonal antibody (mAbs) capture statistics,
where the combinatorial antibody library provides antibodies that bind targets with an affinity and specificity, where the antibodies are derived from cloned antibody genes in single-chain Fv (scFv) or Fab format for convenient manipulation and with DNA encoding that sequences and permits a functional linkage between target recognition and sequence replication to facilitate screening and identification of polypeptides.

2. The SH SAW biosensor of claim 1 where the crystal resonator comprises a SAW biosensor to generate a label free, nucleic acids output signal, the SAW biosensor having a sensor platform with selected boundary conditions which lower limits of detection (LOD) of the sensor platform, LOD increasing the bandwidth of the SAW sensor, its accuracy and resolution.

3. The SH SAW biosensor of claim 2 where the microcontroller and electronic analog front end interface (AFE) are combined and coupled to the SAW biosensor to convert the generated nucleic acids output signal into a digital signal, which is interpreted to provide real-time or near real-time analysis.

4. The SH SAW biosensor of claim 2 further comprising a handheld disposable instrument for use in the fields of food safety or monitoring food quality for food items prior to consumption, where the LOD, bandwidth, accuracy and resolution of the SAW biosensor are selected to detect a whole microbial pathogen, a protein biomarker and/or a nucleic acid in a biological matrix to provide preventative information with respect to, point-of-care detection of biological contaminations or infection.

5. The SH SAW biosensor of claim 1 where the microfluidic chamber integrated with interdigitated input/output frequency matched electrodes comprises an integrated microfluidic chamber, a waveguide layer and a sensing area incorporated into the waveguide layer by means of the integrated microfluidic chamber.

6. The SH SAW biosensor of claim 2 further comprising a plurality of SAW biosensors corresponding to a plurality of sensor and reference cell pairs in an array, which pairs are coupled through the analog front end circuit (AFE) for signal processing and computational preconditioning, and where the microcontroller controls a frequency sweep cycling of the array, data storage and data processing of cell phase shift magnitudes detected by the plurality of SAW biosensors to form a phase space density matrix in the microcontroller of a plurality of biomarkers from which a diffusion equation of a predetermined underlying cellular biological activity of the corresponding plurality of biomarkers is solved and from which statistical counting of hybridization of protein and analyte in real time is achieved.

7. The SH SAW biosensor of claim 2 further comprising a plurality of SAW biosensors corresponding to a plurality of sensor and reference cell pairs in an array, which pairs are coupled through the analog front end circuit (AFE) for signal processing and computational preconditioning, where the microcontroller controls a frequency sweep cycling of the array, data storage and data processing of cell phase shift magnitudes detected by the plurality of SAW biosensors to reliably measure a degree and time sequencing of a plurality of biomarkers in an aqueous media in real time, where the degree and time sequencing of a plurality of biomarkers in a live cell is mimicked and resolved, and where the sensor cells have functionalized sensing lanes provided with corresponding specific probes, including an antibody, an antigen, a protein, a receptor, an aptamer, a peptide, a DNA strand, or an enzyme, the array of sensor cells incorporate multiple probes for cross validation and increased reliability of resultant sensor outputs.

8. The SH SAW biosensor of claim 1 where the analog front end circuit measures a plurality of sensory outputs continuously over a time domain and a frequency domain and measures a quantified rate of change of an analyte or a molecule in vitro, providing real time-mimicry of at least one cellular biomarker and biological analyte.

9. The SH SAW biosensor of claim 1 where the microcontroller identifies sequencing of stochastic biological events, identifies timing, location, and statistical measures of hybridization to uncover nature and specificity of cascading effects of protein sequences including uncovering of apparent statistical causal correlations.

10. The SH SAW biosensor of claim 2 further comprising a source follower amplifier coupled to the SAW biosensor to capture biological signals for determining physical hybridization counts for each analyte specimen to account for the time constant, $$\frac{d\tau}{\tau} = \sum_{i=1}^{n} \gamma_{yi} d\gamma_i,$$

computed oy the analog front end circuit (AFE).

11. The SH SAW biosensor of claim 2 where the microcontroller provides continuous sampling of a hybridization timestamp and phase shift to record the kinetics of mass accumulation over the SAW biosensor to compute a curve of mass accumulation prior to saturation of the SAW biosensor and to provide an indication of the mass loading rate of change, which is estimated using an algorithmic technique of prediction based on hybridization time constant (T), so that in cases of a large analyte quantity, saturation of the sensing lane due to the amount of antibodies packed over the surface is avoided.

12. The SH SAW biosensor of claim 2 where the SAW biosensor is disposed in the microfluidic chamber, which is provided with flowing biological fluids in a buffer solution and where the SAW biosensor is characterized by an electrical polarity of the sensing lane, where the electrical polarity is modulated to attract and then release a plurality of VEGF molecules to prevent a buildup of ionic molecules on the sensor lane by layering of spacer molecules and by concentrating antibody fragments on the sensing lane, thereby avoiding false negative or false positive results due to contamination of nonspecific attraction to the sensing lane altering the mass loading of the SAW biosensor, while preventing sedimentation and nonspecific binding of ionic residue within the buffer solution, and thereby enabling a continuous flow of the biological fluids flowing through the microfluidic chamber.

13. The SH SAW biosensor of claim 1 further comprising an alarm circuit coupled to a computing device, where a plurality of SAW biosensors are combined in an array of microfluidic cells, which are individually addressable with respect to measurement of timing and density of processes occurring within the microfluidic cells to permit the measure of sequencing order of selected modes of biological cascading effects of multiple proteins within a sample, and to enable simultaneous actuation of the alarm circuit in response to detected interdependence of causal statistics in a predetermined relation between different biological species simultaneously available in the sample.

14. The SH SAW biosensor of claim 2 where the SAW biosensor has a sensing surface functionalized by an IgG antibody selectively constructed from a phage display library.

15. The SH SAW biosensor of claim 2 where the SAW biosensor has a sensing surface functionalized by a fragment antigen binding (Fab) fragment, single chain variable fragment (scFv) or single-domain antibody fragment.

16. The SH SAW biosensor of claim 15 where the F(ab) fragment is an antibody structure that binds to an antigen but that is monovalent with no Fc portion.

17. The SH SAW biosensor of claim 14 where the SAW biosensor sensing surface functionalized by an IgG antibody includes a F(ab')2 fragment antibody is generated by pepsin digestion of the whole IgG antibody to remove most of the Fc region while leaving intact some of a hinge region with two antigen-binding F(ab) portions linked together by disulfide bonds.

* * * * *